US012570710B2

(12) United States Patent
Zhang et al.

(10) Patent No.: US 12,570,710 B2
(45) Date of Patent: Mar. 10, 2026

(54) TARGETING LILRB4 WITH CAR-T OR CAR-NK CELLS IN THE TREATMENT OF CANCER

(71) Applicant: THE BOARD OF REGENTS OF THE UNIVERSITY OF TEXAS SYSTEM, Austin, TX (US)

(72) Inventors: Chengcheng Zhang, Dallas, TX (US); Samuel John, Dallas, TX (US); Heyu Chen, Dallas, TX (US); Mi Deng, Plano, TX (US); Xun Gui, Houston, TX (US); Ningyan Zhang, Houston, TX (US); Zhiqiang An, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 1469 days.

(21) Appl. No.: 16/762,273

(22) PCT Filed: Nov. 6, 2018

(86) PCT No.: PCT/US2018/059362
§ 371 (c)(1),
(2) Date: May 7, 2020

(87) PCT Pub. No.: WO2019/094360
PCT Pub. Date: May 16, 2019

(65) Prior Publication Data
US 2021/0179687 A1 Jun. 17, 2021

Related U.S. Application Data

(60) Provisional application No. 62/584,770, filed on Nov. 11, 2017, provisional application No. 62/583,825, filed on Nov. 9, 2017, provisional application No. 62/582,769, filed on Nov. 7, 2017.

(51) Int. Cl.
| | |
|---|---|
| *C07K 14/705* | (2006.01) |
| *A61K 38/00* | (2006.01) |
| *A61K 40/11* | (2025.01) |
| *A61K 40/15* | (2025.01) |
| *A61K 40/31* | (2025.01) |
| *A61K 40/42* | (2025.01) |
| *A61K 40/50* | (2025.01) |
| *A61K 45/06* | (2006.01) |
| *A61P 35/02* | (2006.01) |
| *C12N 5/0783* | (2010.01) |
| *C12N 15/00* | (2006.01) |

(52) U.S. Cl.
CPC ........ *C07K 14/70503* (2013.01); *A61K 40/11* (2025.01); *A61K 40/15* (2025.01); *A61K 40/31* (2025.01); *A61K 40/421* (2025.01); *A61K 45/06* (2013.01); *A61P 35/02* (2018.01); *C12N 5/0636* (2013.01); *C12N 5/0646* (2013.01); *C12N 15/00* (2013.01); *A61K 38/00* (2013.01); *A61K 40/50* (2025.01); *A61K 2239/31* (2023.05); *A61K 2239/38* (2023.05); *C12Y 207/07* (2013.01)

(58) Field of Classification Search
CPC .. A61K 35/17; A61K 40/31; C07K 14/70503; C07K 14/7051
See application file for complete search history.

(56) References Cited

U.S. PATENT DOCUMENTS

| | | | |
|---|---|---|---|
| 2014/0271582 | A1 | 9/2014 | Forman et al. |
| 2017/0095531 | A1 | 4/2017 | Schreiber et al. |

FOREIGN PATENT DOCUMENTS

| | | |
|---|---|---|
| CN | 106999585 A | 8/2017 |
| JP | 2014-507118 | 3/2014 |
| JP | 2016-514457 | 5/2016 |
| JP | 2016-525881 | 9/2016 |
| KR | 10-2016-0145802 | 12/2016 |
| WO | WO 2009/155723 | 12/2009 |
| WO | WO 2012/079000 | 6/2012 |
| WO | WO 2014/144622 | 9/2014 |
| WO | WO 2014/186469 | 11/2014 |
| WO | WO 2015/164594 | 10/2015 |
| WO | WO 2016/049641 | 3/2016 |
| WO | WO 2016/123333 | 8/2016 |
| WO | WO 2016/130726 | 8/2016 |
| WO | WO 2016/144728 | 9/2016 |
| WO | WO 2016/207240 | 12/2016 |
| WO | WO 2017/095531 | 6/2017 |

OTHER PUBLICATIONS

Deng et al. (Nature. Oct. 2018; 562 (7728): 605-9; author manuscript; pp. 1-45).*
Bridgeman et al. (J.Immunol. Jun. 15, 2010; 184 (12): 6938-49).*
Ma et al. (Prostate. Sep. 15, 2004; 61 (1): 12-25).*
Hudecek et al. (Clin. Cancer Res. Jun. 1, 20135; 19 (12): 3153-64).*
Lu et al. (J. Biol. Chem. Dec. 11, 2009; 284 (50): 34839-48).*
John et al. (Mol. Ther. Oct. 3, 2017; 26 (10): 2487-2495).*
Perna et al. (Cancer Cell. Oct. 9, 2017; 32 (4): 506-519).*
Park et al. (Sci. Rep. 2017; 7: 14366; pp. 1-15).*
Kebriaei et al. (J. Clin. Invest. Sep. 1, 2016; 126 (9): 3363-76).*
Winkler et al. (J. Immunol. Oct. 15, 2000; 165 (8): 4505-4514).*
Barrett et al., "Interleukin 6 is not Made By Chimeric Antigen Receptor T Cells and Does not Impact Their Function" *Blood*, 128, 654, 2016.
Chen et al., "Signalling thresholds and negative B-cell selection in acute lymphoblastic leukaemia" *Nature*, 521: 357-361, 2015.
Extended European Search Report issued in European Patent Application No. 18876416.1, dated Aug. 6, 2021.

(Continued)

*Primary Examiner* — Gregory S Emch
(74) *Attorney, Agent, or Firm* — pH IP Law

(57) ABSTRACT

The present disclosure provides methods and compositions for immunotherapy employing a modified T cell or NK cell comprising a chimeric LILRB4 antigen receptor (CAR) that can be administered to patients for disease (e.g., cancer) treatment.

16 Claims, 19 Drawing Sheets

Specification includes a Sequence Listing.

(56)            References Cited

OTHER PUBLICATIONS

International Preliminary Report on Patentability issued in corresponding PCT Application No. PCT/US2018/059362, mailed on May 22, 2020.

International Search Report and Written Opinion issued in corresponding PCT Application No. PCT/US2018/059362, mailed on Mar. 29, 2019.

John et al., "A Novel Anti-LILRB4 CAR-T Cell for the Treatment of Monocytic AML." *Mol Ther.* 26(10):2487-2495, 2018.

Kang et al., "The ITIM-containing receptor LAIRI is essential for acute myeloid leukaemia development" *Nat Cell Biol*, 17: 665-677, 2015.

Kang et al., "Inhibitory leukocyte immunoglobulin-like receptors: Immune checkpoint proteins and tumor sustaining factors." *Cell Cycle.* 2016;15(1):25-40, 2016.

Rotiroti et al., "Acute Myeloid Leukemia Targeting by Chimeric Antigen Receptor T Cells: Bridging the Gap from Preclinical Modeling to Human Studies." *Hum Gene Ther.* 28(3):231-241, 2017.

Tashiro et al., "Treatment of Acute Myeloid Leukemia with T Cells Expressing Chimeric Antigen Receptors Directed to C-type Lectin-like Molecule 1." *Mol Ther*. 25(9):2202-2213, 2017.

Zhang et al., "Leukocyte immunoglobulin-like receptors in human diseases: an overview of their distribution, function, and potential application for immunotherapies." *J Leukoc Biol*. 102(2):351-360, 2017.

Zheng et al., "Inhibitory receptors bind ANGPTLs and support blood stem cells and leukaemia development" *Nature*, 485, 656-660, 2012.

Office Communication Issued in corresponding Japanese Application No. 2020-524547, dated Jul. 28, 2022. English Translation.

Office Communication Issued in corresponding Chinese Application No. 201880085571.6, dated Nov. 2, 2022. English Translation.

Orentas, Rimas J., et al. "Identification of cell surface proteins as potential immunotherapy targets in 12 pediatric cancers." *Frontiers in oncology* 2 (2012): 194.

Office Communication Issued in corresponding European Application No. 18876416.1, dated May 17, 2024.

Office Communication Issued in corresponding Korean Application No. 10-2020-7014347, dated Apr. 11, 2024. English Translation.

* cited by examiner

A

B

[1]GeneAtlas (GSE1133): LILRB4 [210152_at]

[2]Human Proteome Map: LILRB4

| Mean (SD): | 50.16 (18.25) | 111.35 (82.52) |

H
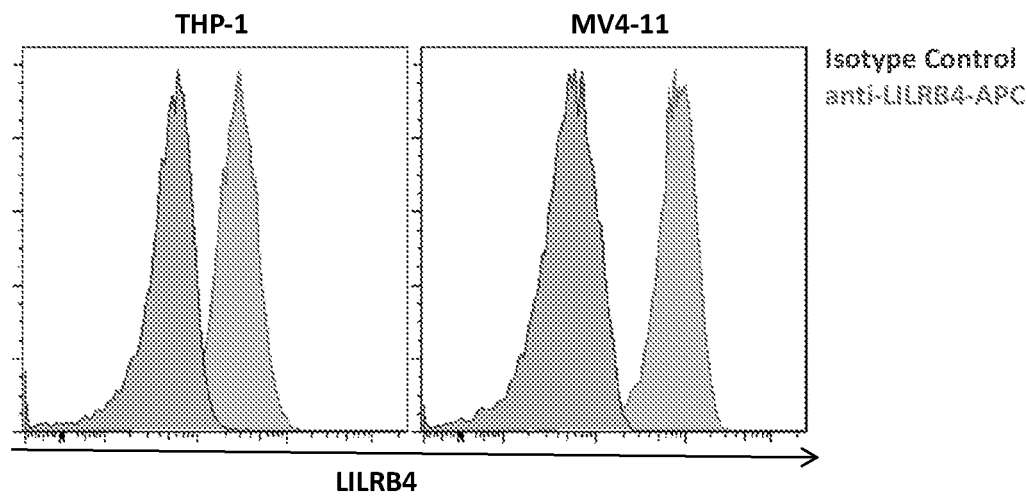
FIG. 1H
Anti-LILRB4 scFv-CD28-CD3z (w/CD28 TM)
Anti-LILRB4 scFv-CD28-CD3z (w/CD8 TM)
Anti-LILRB4 scFv-41BB-CD3z
Anti-LILRB4 scFv-CD28-41BB-CD3z
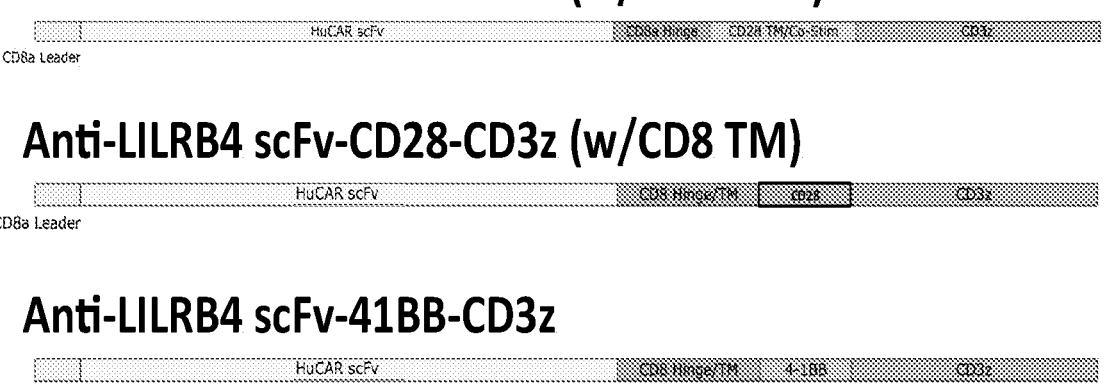
FIG. 2

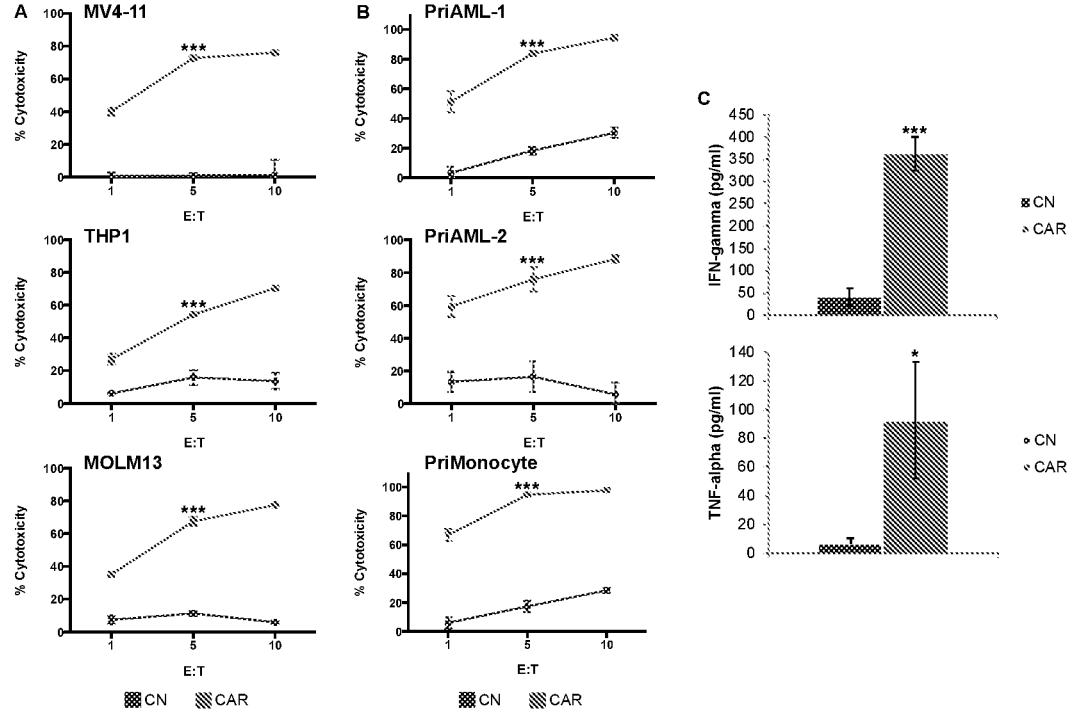
FIGS. 4A-C

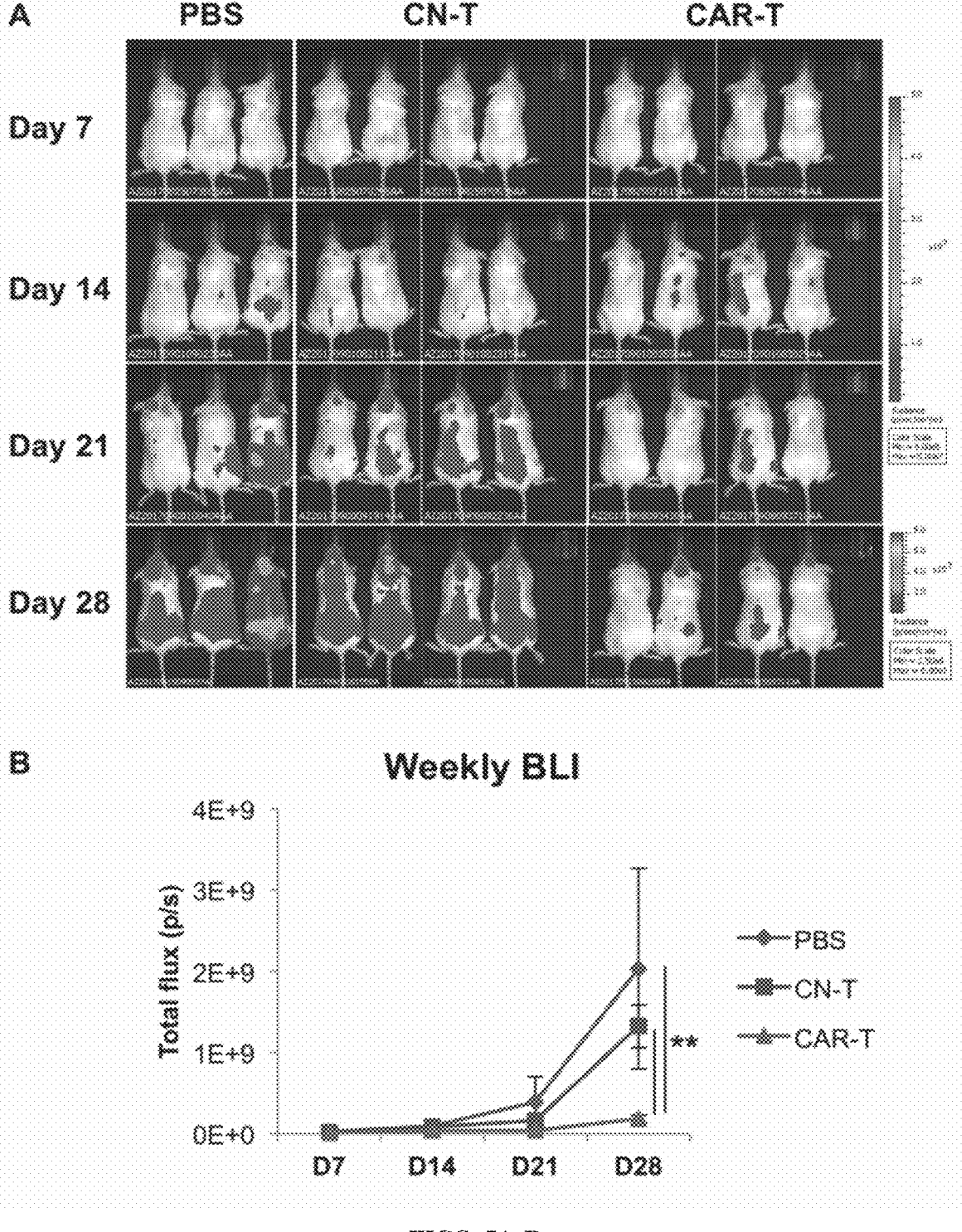
FIGS. 5A-B

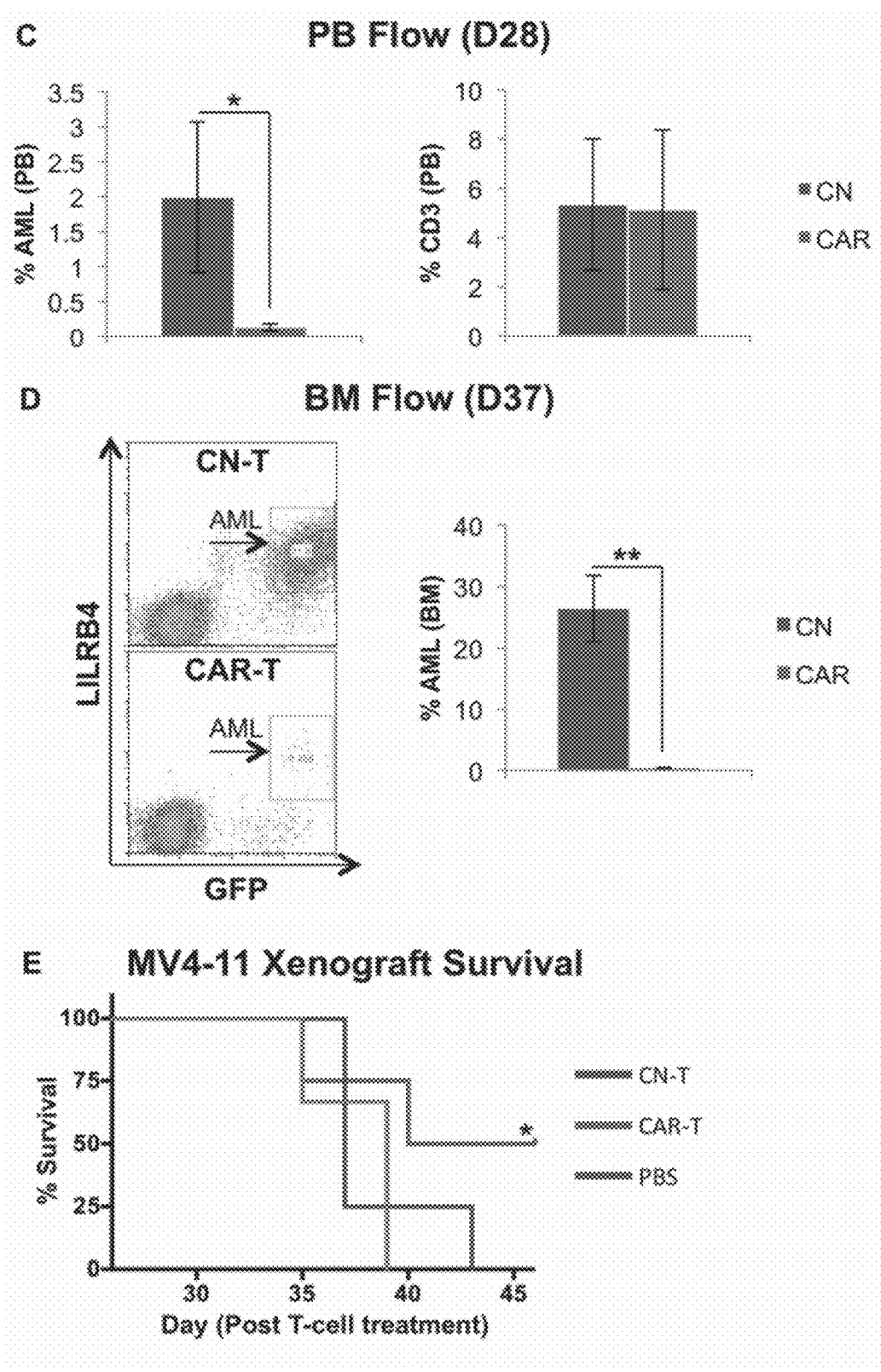
FIGS. 5C-E

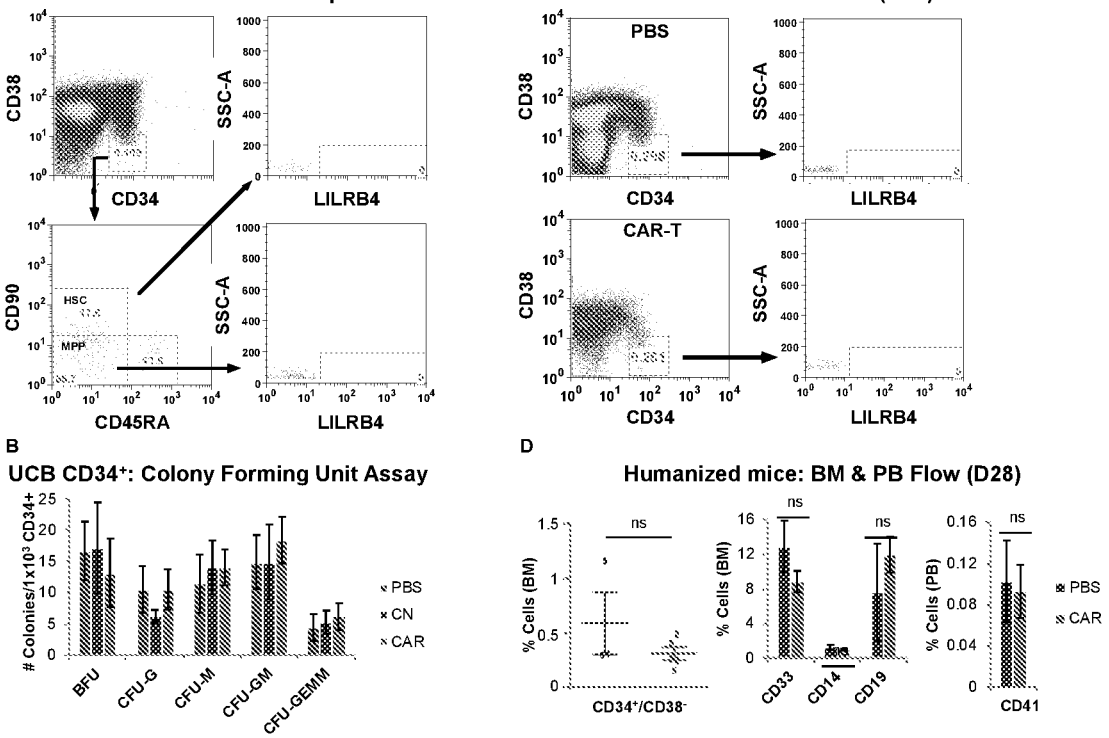
FIGS. 6A-D

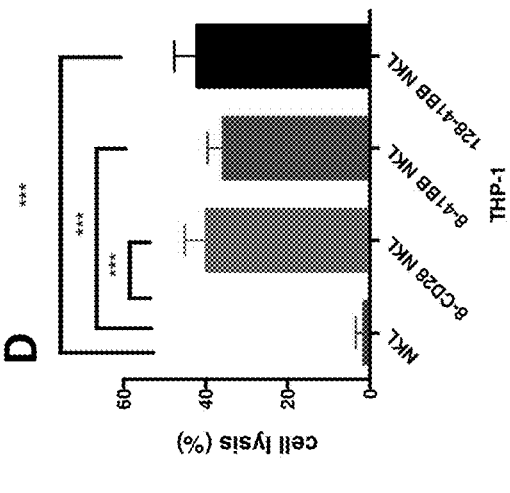
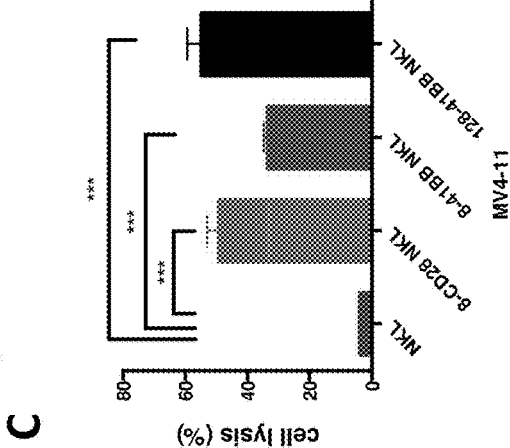
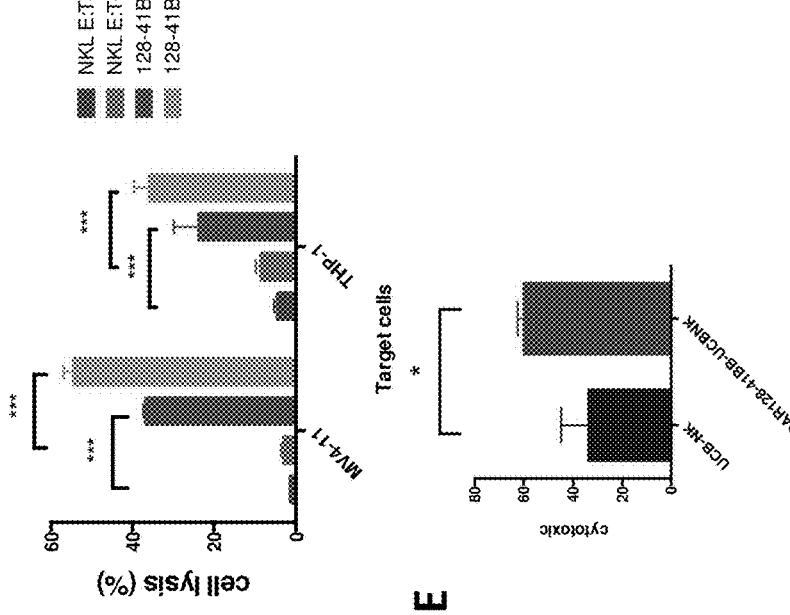
FIGS. 7B-E

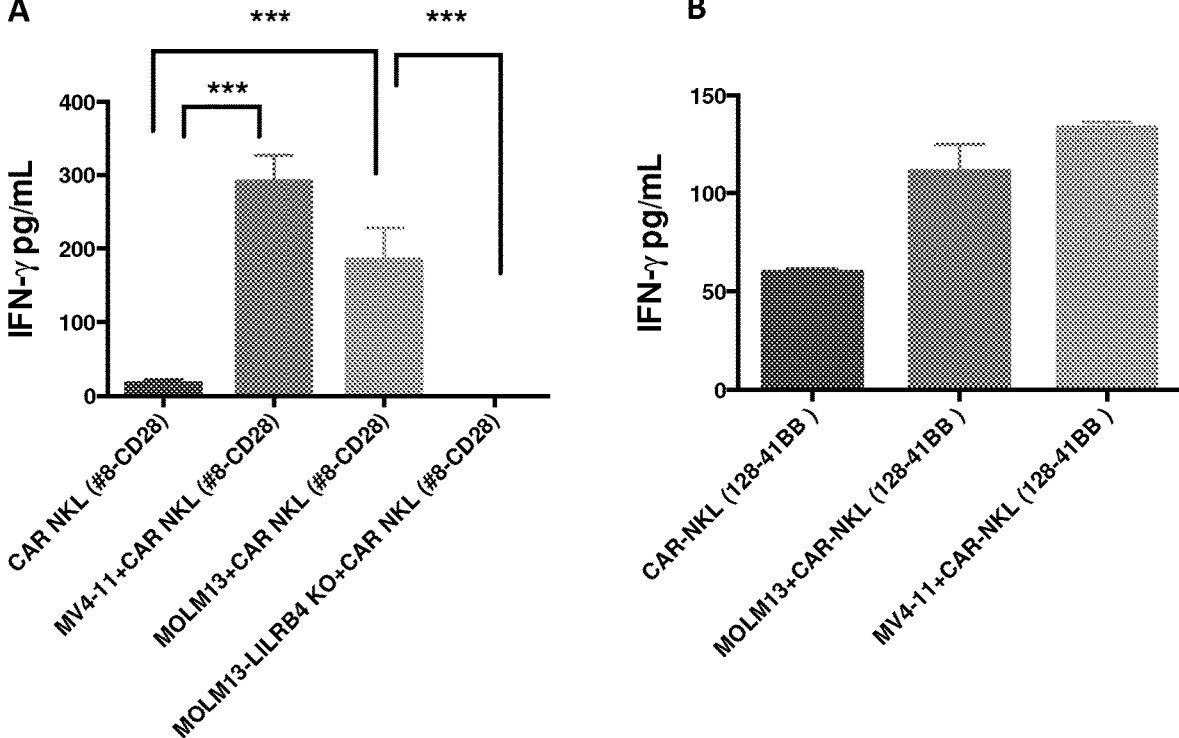
FIGS. 8A-B

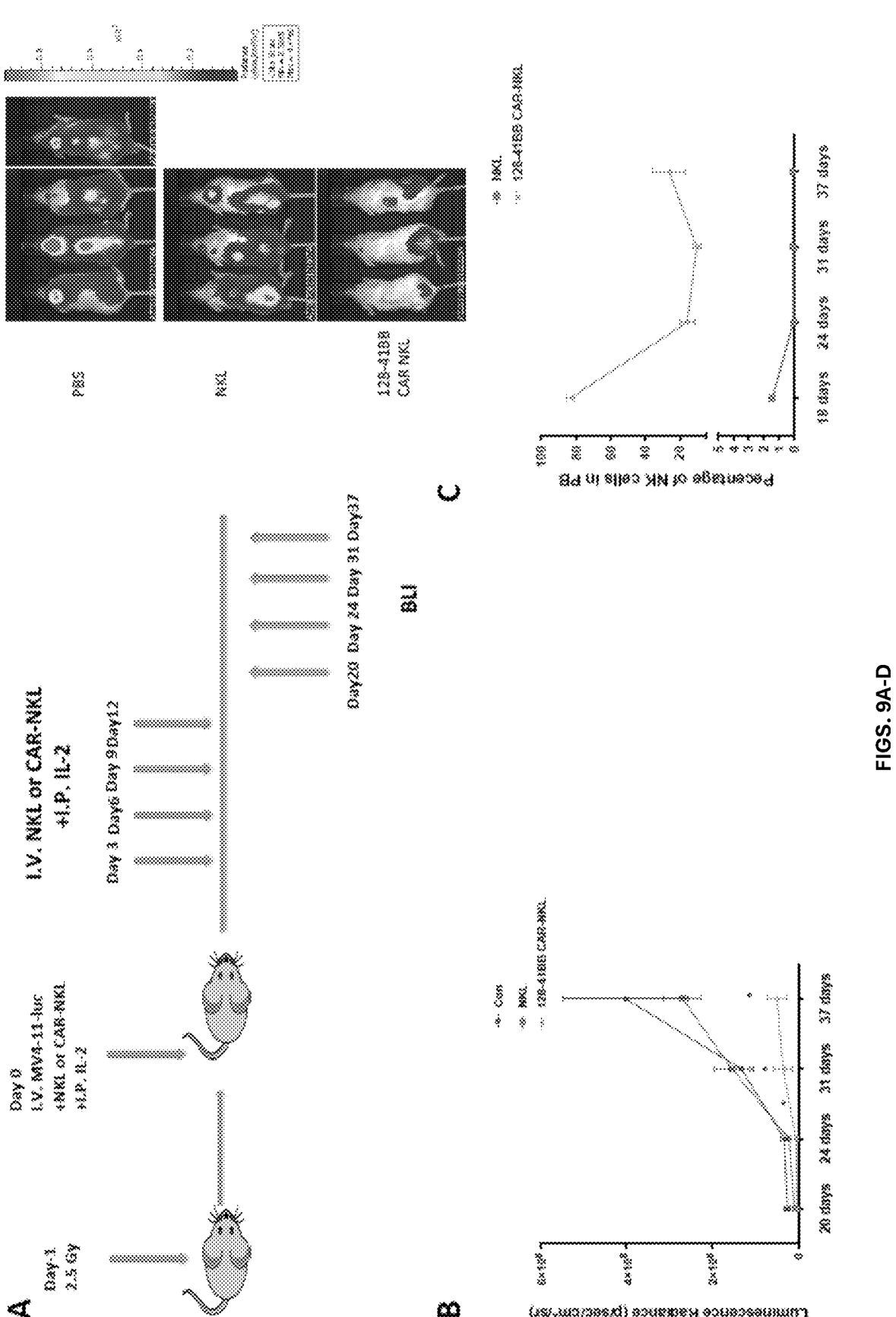
FIGS. 9A-D

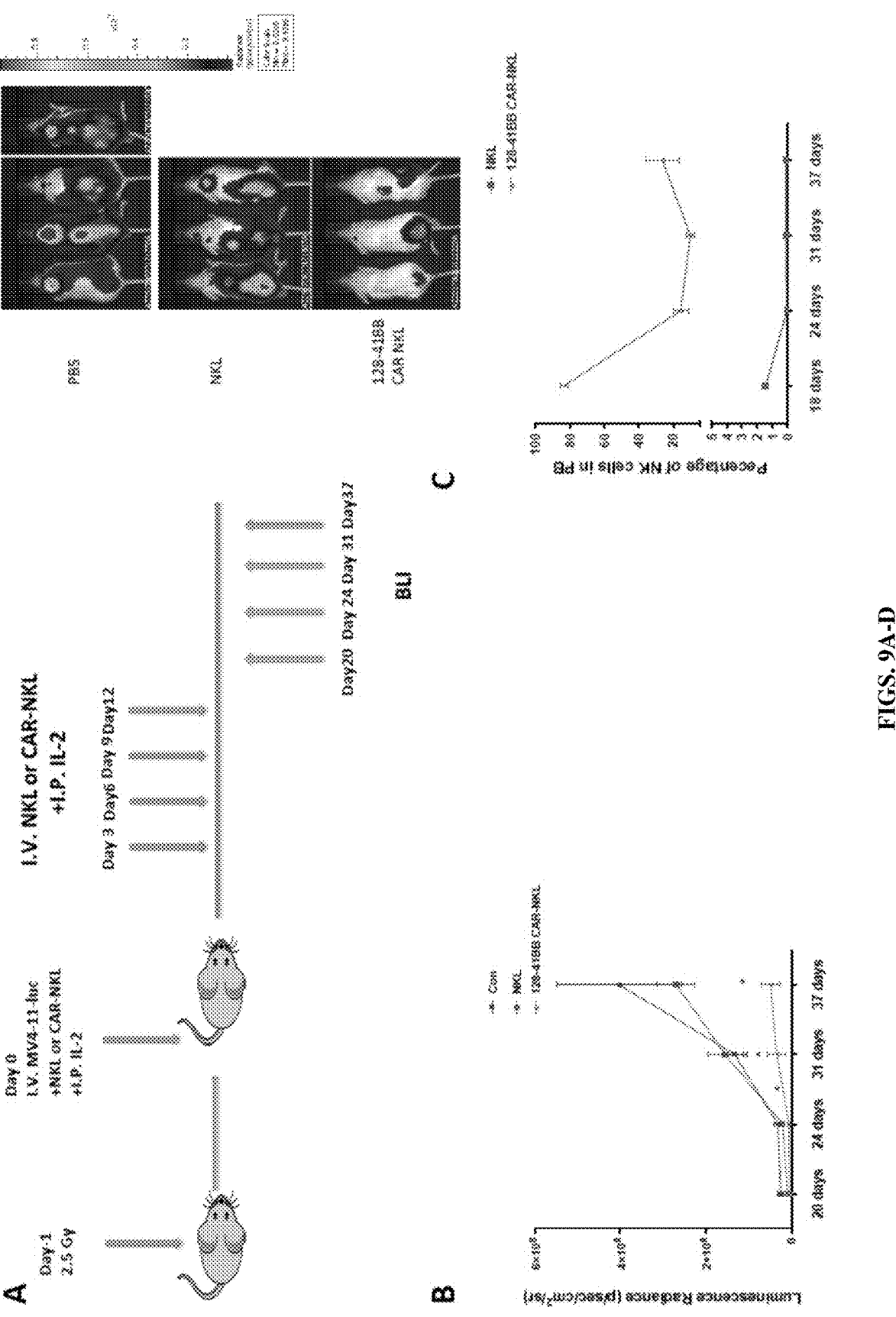
FIGS. 9A-D

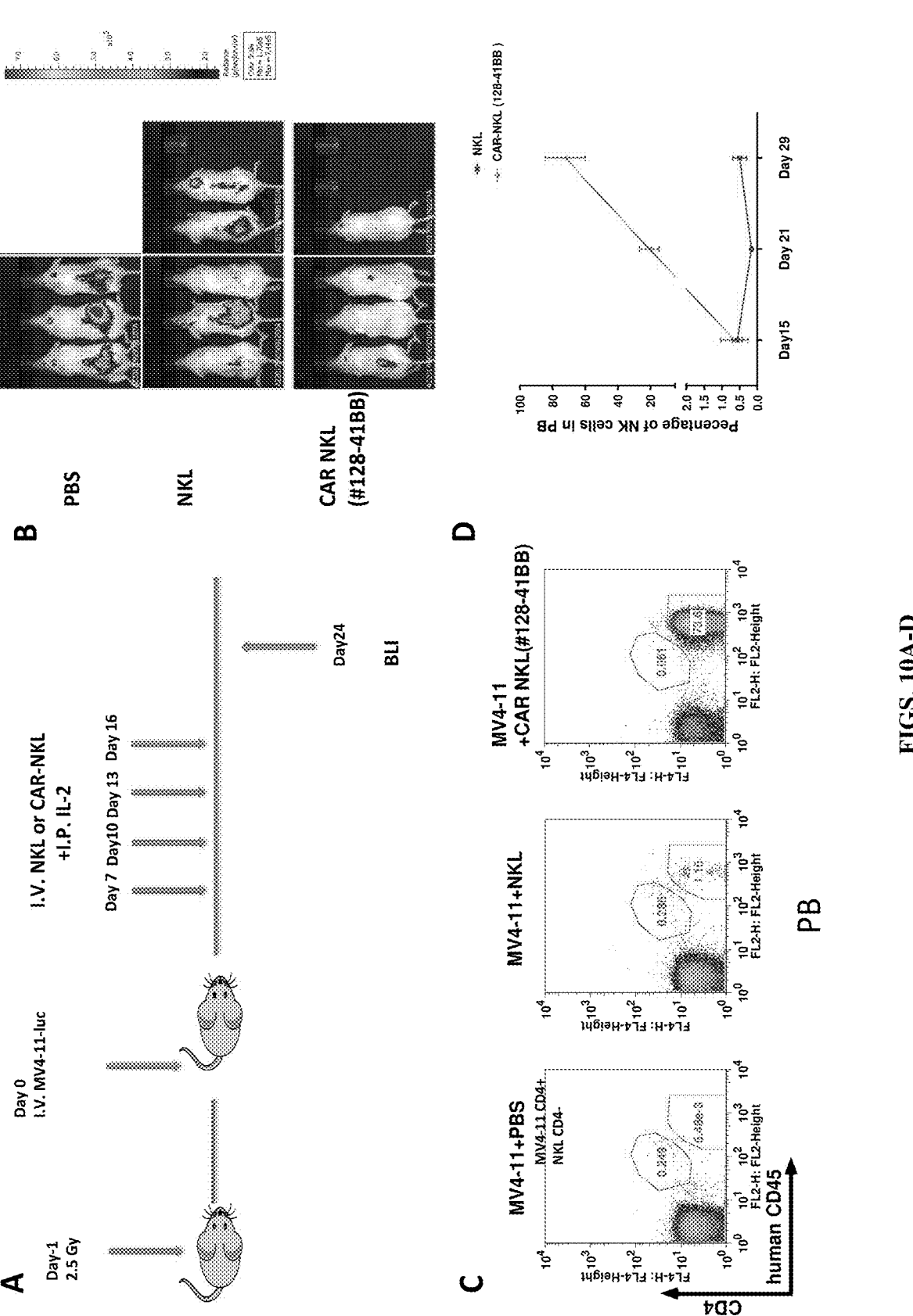
FIGS. 10A-D

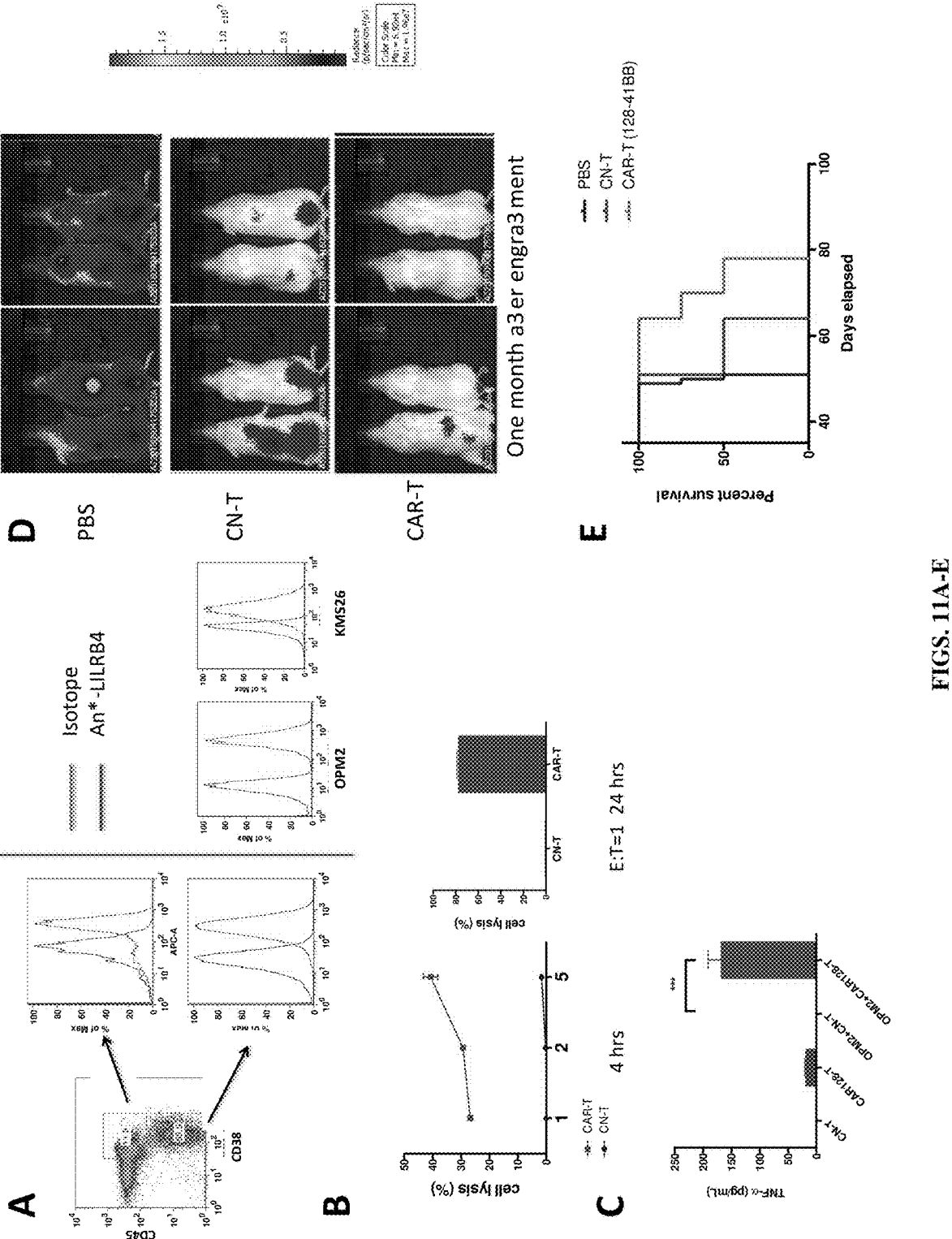
FIGS. 11A-E

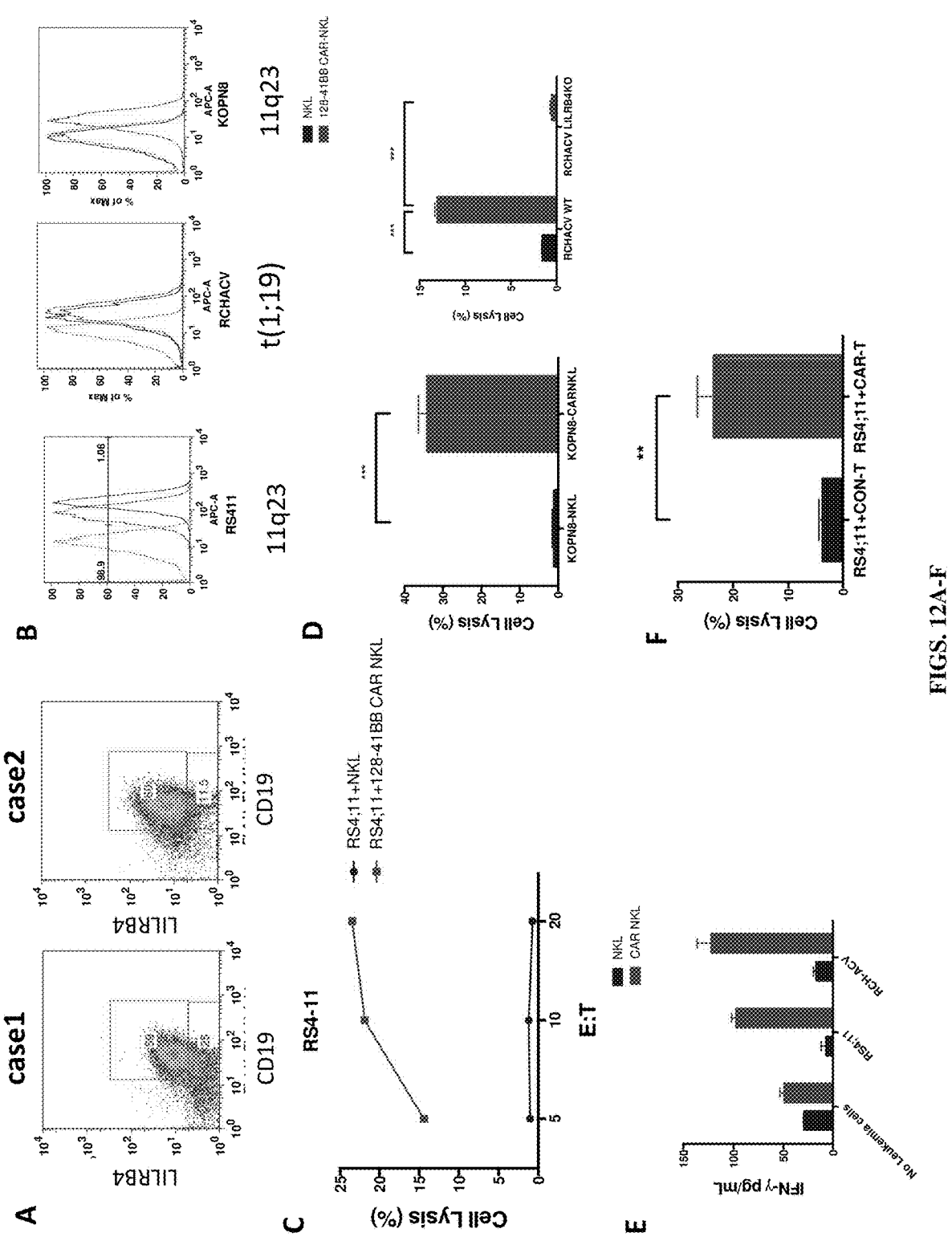
FIGS. 12A-F

SEQUENCE LISTING

<160> NUMBER OF SEQ ID NOS: 43

<210> SEQ ID NO 1

-continued

```
<211> LENGTH: 9
<212> TYPE: PRT
<213> ORGANISM: Artificial sequence
<220> FEATURE:
<223> OTHER INFORMATION: Synthetic construct

<400> SEQUENCE: 1

Gly Ile Asp Phe Ser Asn His Tyr Tyr
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic construct

<400> SEQUENCE: 2

Ile Phe Ser Gly Asp Ser Ala Ser Thr
1               5

<210> SEQ ID NO 3
<211> LENGTH: 13
<212> TYPE: PRT
<213> ORGANISM: Artificial sequence
<220> FEATURE:
<223> OTHER INFORMATION: Synthetic construct

<400> SEQUENCE: 3

Ala Arg Gly Met Ser Thr Asn Asp Trp Ala Ser Asp Leu
1               5                   10

<210> SEQ ID NO 4
<211> LENGTH: 7
<212> TYPE: PRT
<213> ORGANISM: Artificial sequence
<220> FEATURE:
<223> OTHER INFORMATION: Synthetic construct

<400> SEQUENCE: 4

Glu Ser Ile Asn Ser Ile Tyr
1               5

<210> SEQ ID NO 5
<211> LENGTH: 3
<212> TYPE: PRT
<213> ORGANISM: Artificial sequence
<220> FEATURE:
<223> OTHER INFORMATION: Synthetic construct

<400> SEQUENCE: 5

Arg Ala Ser
1

<210> SEQ ID NO 6
<211> LENGTH: 12
<212> TYPE: PRT
<213> ORGANISM: Artificial sequence
<220> FEATURE:
<223> OTHER INFORMATION: Synthetic construct

<400> SEQUENCE: 6

Gln Gln Ser Tyr Asp Trp Gly Asp Val Glu Asn Thr
1               5                   10

<210> SEQ ID NO 7
<211> LENGTH: 122
```

```
<212> TYPE: PRT
<213> ORGANISM: Artificial sequence
<220> FEATURE:
<223> OTHER INFORMATION: Synthetic construct

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Asn His
            20                  25                  30

Tyr Tyr Ile Tyr Trp Val Arg Gln Ala Pro Gly Lys Gly Leu Glu Trp
        35                  40                  45

Ile Gly Cys Ile Phe Ser Gly Asp Ser Ala Ser Thr Tyr Tyr Ala Ser
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Met Ser Thr Asn Asp Trp Ala Ser Asp Leu Trp
            100                 105                 110

Gly Gln Gly Thr Leu Val Thr Val Ser Ser
        115                 120

<210> SEQ ID NO 8
<211> LENGTH: 366
<212> TYPE: DNA
<213> ORGANISM: Artificial sequence
<220> FEATURE:
<223> OTHER INFORMATION: Synthetic construct

<400> SEQUENCE: 8
gaggtgcagc tgctggagag cggaggaggc ctggtgcagc ctggaggatc cctgaggctg     60
tcctgtgccg cctccggcat cgacttctcc aaccactact acatctactg ggtgaggcag    120
gctcccggca agggactgga gtggatcggc tgtatcttct ccggcgactc cgcctccacc    180
tactacgcct cctgggccaa gggcaggttt accatctccc gggacaactc caagaacacc    240
ctgtacctgc agatgaactc cctgagggcc gaggacaccg ctgtgtacta ctgcgccagg    300
ggcatgtcca ccaacgactg ggcttccgat ctgtggggcc agggcacact ggtgaccgtg    360
tccagc                                                              366

<210> SEQ ID NO 9
<211> LENGTH: 111
<212> TYPE: PRT
<213> ORGANISM: Artificial sequence
<220> FEATURE:
<223> OTHER INFORMATION: Synthetic construct

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Ser Ile Asn Ser Ile
            20                  25                  30

Tyr Leu Ala Trp Tyr Gln Gln Lys Pro Gly Lys Ala Pro Lys Leu Leu
        35                  40                  45

Ile Tyr Arg Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80
```

-continued

```
Pro Glu Asp Phe Ala Thr Tyr Tyr Cys Gln Gln Ser Tyr Asp Trp Gly
            85                  90                  95

Asp Val Glu Asn Thr Phe Gly Gly Gly Thr Lys Val Glu Ile Lys
            100                 105                 110

<210> SEQ ID NO 10
<211> LENGTH: 333
<212> TYPE: DNA
<213> ORGANISM: Artificial sequence
<220> FEATURE:
<223> OTHER INFORMATION: Synthetic construct

<400> SEQUENCE: 10
gacatccaga tgacccagtc cccttcctcc ctgtccgctt ccgtgggcga tagggtgacc      60
atcacctgcc aggcctccga gtccatcaac agcatctacc tggcctggta ccagcagaag     120
cccggcaagg cccccaagct gctgatctat cgggcttcca cactggcctc cggagtgcct     180
tccaggtttt ccggctccgg ctccggcacc gacttcaccc tgaccatctc cagcctgcag     240
cccgaggact tcgccaccta ctactgccag cagtcctacg actggggcga cgtggagaac     300
acctttggcg gcggcaccaa ggtggagatc aag                                  333

<210> SEQ ID NO 11
<211> LENGTH: 8
<212> TYPE: PRT
<213> ORGANISM: Artificial sequence
<220> FEATURE:
<223> OTHER INFORMATION: Synthetic construct

<400> SEQUENCE: 11

Gly Phe Ser Leu Ile Ser Tyr Asp
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic construct

<400> SEQUENCE: 12

Ile Tyr Ser Asp Gly Tyr Thr
1               5

<210> SEQ ID NO 13
<211> LENGTH: 7
<212> TYPE: PRT
<213> ORGANISM: Artificial sequence
<220> FEATURE:
<223> OTHER INFORMATION: Synthetic construct

<400> SEQUENCE: 13

Ala Thr Asn Ala Phe Ala Leu
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic construct

<400> SEQUENCE: 14

Gln Asn Val Tyr Asn Asn Asn Trp
```

-continued

```
1               5
```

```
<210> SEQ ID NO 15
<211> LENGTH: 3
<212> TYPE: PRT
<213> ORGANISM: Artificial sequence
<220> FEATURE:
<223> OTHER INFORMATION: Synthetic construct

<400> SEQUENCE: 15

Thr Ala Ser
1

<210> SEQ ID NO 16
<211> LENGTH: 10
<212> TYPE: PRT
<213> ORGANISM: Artificial sequence
<220> FEATURE:
<223> OTHER INFORMATION: Synthetic construct

<400> SEQUENCE: 16

Ala Gly Gly Tyr Ser Gly Pro Ile Tyr Thr
1               5                   10

<210> SEQ ID NO 17
<211> LENGTH: 113
<212> TYPE: PRT
<213> ORGANISM: Artificial sequence
<220> FEATURE:
<223> OTHER INFORMATION: Synthetic construct

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Ile Ser Tyr
            20                  25                  30

Asp Met Tyr Trp Val Arg Gln Ala Pro Gly Lys Gly Leu Glu Tyr Ile
        35                  40                  45

Gly Ile Ile Tyr Ser Asp Gly Tyr Thr Phe Tyr Ala Thr Gly Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr Asn Ala Phe Ala Leu Trp Gly Arg Gly Thr Leu Val Thr Val Ser
            100                 105                 110

Ser

<210> SEQ ID NO 18
<211> LENGTH: 339
<212> TYPE: DNA
<213> ORGANISM: Artificial sequence
<220> FEATURE:
<223> OTHER INFORMATION: Synthetic construct

<400> SEQUENCE: 18
gaggtgcagc tgctggaatc cggaggagga ctggtgcagc ctggcggatc cctgaggctg      60
tcctgcgctg cttccggctt ctccctgatc agctacgaca tgtactgggt gaggcaggct     120
cctggcaagg gcctggagta catcggcatc atctactccg acggctacac cttctacgcc     180
accggcgcca agggcaggtt caccatctcc agggacaact ccaagaacac cctgtacctg     240
```

-continued

```
cagatgaact ccctgagggc cgaggacacc gccgtgtact actgcgccac caacgccttc        300
gctctgtggg gcaggggcac actggtgacc gtctcctcc                               339
```

```
<210> SEQ ID NO 19
<211> LENGTH: 110
<212> TYPE: PRT
<213> ORGANISM: Artificial sequence
<220> FEATURE:
<223> OTHER INFORMATION: Synthetic construct

<400> SEQUENCE: 19

Ala Ile Gln Leu Thr Gln Ser Pro Ser Ser Leu Ser Ala Ser Val Gly
1               5                   10                  15

Asp Arg Val Thr Ile Thr Cys Gln Ser Ser Gln Asn Val Tyr Asn Asn
                20                  25                  30

Asn Trp Leu Val Trp Leu Gln Gln Lys Pro Gly Lys Ala Pro Lys Arg
            35                  40                  45

Leu Ile Tyr Thr Ala Ser Ser Leu Ala Ser Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Tyr Ser Gly
                85                  90                  95

Pro Ile Tyr Thr Phe Gly Gly Gly Thr Lys Val Glu Ile Lys
            100                 105                 110
```

```
<210> SEQ ID NO 20
<211> LENGTH: 330
<212> TYPE: DNA
<213> ORGANISM: Artificial sequence
<220> FEATURE:
<223> OTHER INFORMATION: Synthetic construct

<400> SEQUENCE: 20
gccatccagc tgacccagtc cccttcctcc ctgtccgctt ccgtgggcga cagggtgacc         60
atcacctgcc agtcctccca gaacgtgtac aacaacaact ggctggtctg gctgcagcag        120
aagcccggca aggcccctaa gaggctgatc tacaccgctt cctccctggc ttccggagtg        180
ccctccaggt tttccggctc cggctccggc accgatttca ccctgaccat ctcctccctg        240
cagcccgagg acttcgccac ctactactgc gccggcggct actccggccc tatctacacc        300
ttcggcggcg gcaccaaggt ggagatcaag                                          330
```

```
<210> SEQ ID NO 21
<211> LENGTH: 489
<212> TYPE: PRT
<213> ORGANISM: Artificial sequence
<220> FEATURE:
<223> OTHER INFORMATION: Synthetic construct

<400> SEQUENCE: 21

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Ile
            35                  40                  45

Asp Phe Ser Asn His Tyr Tyr Ile Tyr Trp Val Arg Gln Ala Pro Gly
        50                  55                  60
```

```
Lys Gly Leu Glu Trp Ile Gly Cys Ile Phe Ser Gly Asp Ser Ala Ser
65                  70                  75                  80

Thr Tyr Tyr Ala Ser Trp Ala Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Val Tyr Tyr Cys Ala Arg Gly Met Ser Thr Asn Asp Trp
            115                 120                 125

Ala Ser Asp Leu Trp Gly Gln Gly Thr Leu Val Thr Val Ser Ser Gly
            130                 135                 140

Gly Gly Gly Ser Gly Gly Gly Ser Gly Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Gln Ala Ser Glu Ser Ile Asn Ser Ile Tyr Leu
            180                 185                 190

Ala Trp Tyr Gln Gln Lys Pro Gly Lys Ala Pro Lys Leu Leu Ile Tyr
            195                 200                 205

Arg Ala Ser Thr Leu Ala Ser Gly Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ser Tyr Asp Trp Gly Asp Val
                245                 250                 255

Glu Asn Thr Phe Gly Gly Gly Thr Lys Val Glu Ile Lys Thr Thr Thr
            260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Arg
                325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
            355                 360                 365

Arg Asp Phe Ala Ala Tyr Arg Ser Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
            405                 410                 415

Arg Asp Pro Glu Met Gly Gly Lys Pro Gln Arg Arg Lys Asn Pro Gln
            420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
            450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
```

485

```
<210> SEQ ID NO 22
<211> LENGTH: 490
<212> TYPE: PRT
<213> ORGANISM: Artificial sequence
<220> FEATURE:
<223> OTHER INFORMATION: Synthetic construct

<400> SEQUENCE: 22

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Ile
        35                  40                  45

Asp Phe Ser Asn His Tyr Tyr Ile Tyr Trp Val Arg Gln Ala Pro Gly
    50                  55                  60

Lys Gly Leu Glu Trp Ile Gly Cys Ile Phe Ser Gly Asp Ser Ala Ser
65                  70                  75                  80

Thr Tyr Tyr Ala Ser Trp Ala Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Val Tyr Tyr Cys Ala Arg Gly Met Ser Thr Asn Asp Trp
            115                 120                 125

Ala Ser Asp Leu Trp Gly Gln Gly Thr Leu Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Gln Ala Ser Glu Ser Ile Asn Ser Ile Tyr Leu
            180                 185                 190

Ala Trp Tyr Gln Gln Lys Pro Gly Lys Ala Pro Lys Leu Leu Ile Tyr
            195                 200                 205

Arg Ala Ser Thr Leu Ala Ser Gly Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ser Tyr Asp Trp Gly Asp Val
                245                 250                 255

Glu Asn Thr Phe Gly Gly Gly Thr Lys Val Glu Ile Lys Thr Thr Thr
            260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
```

```
             355              360              365

Glu Glu Glu Glu Gly Gly Cys Glu Leu Arg Val Lys Phe Ser Arg Ser
    370              375              380

Ala Asp Ala Pro Ala Tyr Gln Gln Gly Gln Asn Gln Leu Tyr Asn Glu
385              390              395              400

Leu Asn Leu Gly Arg Arg Glu Glu Tyr Asp Val Leu Asp Lys Arg Arg
             405              410              415

Gly Arg Asp Pro Glu Met Gly Gly Lys Pro Gln Arg Arg Lys Asn Pro
             420              425              430

Gln Glu Gly Leu Tyr Asn Glu Leu Gln Lys Asp Lys Met Ala Glu Ala
             435              440              445

Tyr Ser Glu Ile Gly Met Lys Gly Glu Arg Arg Arg Gly Lys Gly His
    450              455              460

Asp Gly Leu Tyr Gln Gly Leu Ser Thr Ala Thr Lys Asp Thr Tyr Asp
465              470              475              480

Ala Leu His Met Gln Ala Leu Pro Pro Arg
             485              490
```

```
<210> SEQ ID NO 23
<211> LENGTH: 479
<212> TYPE: PRT
<213> ORGANISM: Artificial sequence
<220> FEATURE:
<223> OTHER INFORMATION: Synthetic construct

<400> SEQUENCE: 23

Met Ala Leu Pro Val Thr Ala Leu Leu Leu Pro Leu Ala Leu Leu Leu
1               5               10              15

His Ala Ala Arg Pro Glu Val Gln Leu Leu Glu Ser Gly Gly Gly Leu
             20              25              30

Val Gln Pro Gly Gly Ser Leu Arg Leu Ser Cys Ala Ala Ser Gly Phe
          35              40              45

Ser Leu Ile Ser Tyr Asp Met Tyr Trp Val Arg Gln Ala Pro Gly Lys
    50              55              60

Gly Leu Glu Tyr Ile Gly Ile Ile Tyr Ser Asp Gly Tyr Thr Phe Tyr
65              70              75              80

Ala Thr Gly Ala Lys Gly Arg Phe Thr Ile Ser Arg Asp Asn Ser Lys
             85              90              95

Asn Thr Leu Tyr Leu Gln Met Asn Ser Leu Arg Ala Glu Asp Thr Ala
          100             105             110

Val Tyr Tyr Cys Ala Thr Asn Ala Phe Ala Leu Trp Gly Arg Gly Thr
          115             120             125

Leu Val Thr Val Ser Ser Gly Gly Gly Ser Gly Gly Gly Gly Ser
    130             135             140

Gly Gly Gly Gly Ser Ala Ile Gln Leu Thr Gln Ser Pro Ser Ser Leu
145             150             155             160

Ser Ala Ser Val Gly Asp Arg Val Thr Ile Thr Cys Gln Ser Ser Gln
             165             170             175

Asn Val Tyr Asn Asn Asn Trp Leu Val Trp Leu Gln Gln Lys Pro Gly
          180             185             190

Lys Ala Pro Lys Arg Leu Ile Tyr Thr Ala Ser Ser Leu Ala Ser Gly
          195             200             205

Val Pro Ser Arg Phe Ser Gly Ser Gly Ser Gly Thr Asp Phe Thr Leu
    210             215             220

Thr Ile Ser Ser Leu Gln Pro Glu Asp Phe Ala Thr Tyr Tyr Cys Ala
```

```
225             230             235             240

Gly Gly Tyr Ser Gly Pro Ile Tyr Thr Phe Gly Gly Gly Thr Lys Val
            245             250             255

Glu Ile Lys Thr Thr Thr Pro Ala Pro Arg Pro Pro Thr Pro Ala Pro
            260             265             270

Thr Ile Ala Ser Gln Pro Leu Ser Leu Arg Pro Glu Ala Cys Arg Pro
            275             280             285

Ala Ala Gly Gly Ala Val His Thr Arg Gly Leu Asp Phe Ala Cys Asp
    290             295             300

Ile Tyr Ile Trp Ala Pro Leu Ala Gly Thr Cys Gly Val Leu Leu Leu
305             310             315             320

Ser Leu Val Ile Thr Arg Ser Lys Arg Ser Arg Leu Leu His Ser Asp
            325             330             335

Tyr Met Asn Met Thr Pro Arg Arg Pro Gly Pro Thr Arg Lys His Tyr
            340             345             350

Gln Pro Tyr Ala Pro Pro Arg Asp Phe Ala Ala Tyr Arg Ser Arg Val
            355             360             365

Lys Phe Ser Arg Ser Ala Asp Ala Pro Ala Tyr Gln Gln Gly Gln Asn
    370             375             380

Gln Leu Tyr Asn Glu Leu Asn Leu Gly Arg Arg Glu Glu Tyr Asp Val
385             390             395             400

Leu Asp Lys Arg Arg Gly Arg Asp Pro Glu Met Gly Gly Lys Pro Gln
            405             410             415

Arg Arg Lys Asn Pro Gln Glu Gly Leu Tyr Asn Glu Leu Gln Lys Asp
            420             425             430

Lys Met Ala Glu Ala Tyr Ser Glu Ile Gly Met Lys Gly Glu Arg Arg
            435             440             445

Arg Gly Lys Gly His Asp Gly Leu Tyr Gln Gly Leu Ser Thr Ala Thr
    450             455             460

Lys Asp Thr Tyr Asp Ala Leu His Met Gln Ala Leu Pro Pro Arg
465             470             475

<210> SEQ ID NO 24
<211> LENGTH: 63
<212> TYPE: DNA
<213> ORGANISM: Artificial sequence
<220> FEATURE:
<223> OTHER INFORMATION: Synthetic construct

<400> SEQUENCE: 24
atggccttac cagtgaccgc cttgctcctg ccgctggcct tgctgctcca cgccgccagg      60
ccg                                                                   63

<210> SEQ ID NO 25
<211> LENGTH: 15
<212> TYPE: PRT
<213> ORGANISM: Artificial sequence
<220> FEATURE:
<223> OTHER INFORMATION: Synthetic construct

<400> SEQUENCE: 25

Gly Gly Gly Gly Ser Gly Gly Gly Gly Ser Gly Gly Gly Gly Ser
1               5               10              15

<210> SEQ ID NO 26
<211> LENGTH: 135
<212> TYPE: DNA
<213> ORGANISM: Artificial sequence
```

```
<220> FEATURE:
<223> OTHER INFORMATION: Synthetic construct

<400> SEQUENCE: 26
accacgacgc cagcgccgcg accaccaaca ccggcgccca ccatcgcgtc gcagccctg      60 tccctgcgcc cagaggcgtg ccggccagcg gcgggggggcg cagtgcacac gaggggctg     120 gacttcgcct gtgat                                                     135

<210> SEQ ID NO 27
<211> LENGTH: 123
<212> TYPE: DNA
<213> ORGANISM: Artificial sequence
<220> FEATURE:
<223> OTHER INFORMATION: Synthetic construct

<400> SEQUENCE: 27
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                  123

<210> SEQ ID NO 28
<211> LENGTH: 126
<212> TYPE: DNA
<213> ORGANISM: Artificial sequence
<220> FEATURE:
<223> OTHER INFORMATION: Synthetic construct

<400> SEQUENCE: 28
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                               126

<210> SEQ ID NO 29
<211> LENGTH: 339
<212> TYPE: DNA
<213> ORGANISM: Artificial sequence
<220> FEATURE:
<223> OTHER INFORMATION: Synthetic construct

<400> SEQUENCE: 29
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc      240 cggagggggca aggggcacga tggcctttac caggtctca gtacagccac caaggacacc      300
tacgacgccc ttcacatgca ggccctgccc cctcgctaa                           339

<210> SEQ ID NO 30
<211> LENGTH: 45
<212> TYPE: DNA
<213> ORGANISM: Artificial sequence
<220> FEATURE:
<223> OTHER INFORMATION: Synthetic construct

<400> SEQUENCE: 30
ggtggaggcg gttcaggtgg cggcggttcg ggcggtggcg gctct                      45

<210> SEQ ID NO 31
```

```
<211> LENGTH: 480
<212> TYPE: PRT
<213> ORGANISM: Artificial sequence
<220> FEATURE:
<223> OTHER INFORMATION: Synthetic construct

<400> SEQUENCE: 31

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Ser Leu Ile Ser Tyr Asp Met Tyr Trp Val Arg Gln Ala Pro Gly Lys
    50                  55                  60

Gly Leu Glu Tyr Ile Gly Ile Ile Tyr Ser Asp Gly Tyr Thr Phe Tyr
65                  70                  75                  80

Ala Thr Gly Ala Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Thr Asn Ala Phe Ala Leu Trp Gly Arg Gly Thr
        115                 120                 125

Leu Val Thr Val Ser Ser Gly Gly Gly Ser Gly Gly Gly Gly Ser
    130                 135                 140

Gly Gly Gly Gly Ser Ala Ile Gln Leu Thr Gln Ser Pro Ser Ser Leu
145                 150                 155                 160

Ser Ala Ser Val Gly Asp Arg Val Thr Ile Thr Cys Gln Ser Ser Gln
                165                 170                 175

Asn Val Tyr Asn Asn Asn Trp Leu Val Trp Leu Gln Gln Lys Pro Gly
            180                 185                 190

Lys Ala Pro Lys Arg Leu Ile Tyr Thr Ala Ser Ser Leu Ala Ser Gly
            195                 200                 205

Val Pro Ser Arg Phe Ser Gly Ser Gly Ser Gly Thr Asp Phe Thr Leu
    210                 215                 220

Thr Ile Ser Ser Leu Gln Pro Glu Asp Phe Ala Thr Tyr Tyr Cys Ala
225                 230                 235                 240

Gly Gly Tyr Ser Gly Pro Ile Tyr Thr Phe Gly Gly Gly Thr Lys Val
                245                 250                 255

Glu Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
        290                 295                 300

Ile Tyr Ile Trp Ala Pro Leu Ala Gly Thr Cys Gly Val Leu Leu Leu
305                 310                 315                 320

Ser Leu Val Ile Thr Lys Arg Gly Arg Lys Lys Leu Leu Tyr Ile Phe
                325                 330                 335

Lys Gln Pro Phe Met Arg Pro Val Gln Thr Thr Gln Glu Glu Asp Gly
            340                 345                 350

Cys Ser Cys Arg Phe Pro Glu Glu Glu Glu Gly Gly Cys Glu Leu Arg
            355                 360                 365

Val Lys Phe Ser Arg Ser Ala Asp Ala Pro Ala Tyr Gln Gln Gly Gln
370                 375                 380
```

-continued

```
Asn Gln Leu Tyr Asn Glu Leu Asn Leu Gly Arg Arg Glu Glu Tyr Asp
385             390             395             400

Val Leu Asp Lys Arg Arg Gly Arg Asp Pro Glu Met Gly Gly Lys Pro
            405             410             415

Gln Arg Arg Lys Asn Pro Gln Glu Gly Leu Tyr Asn Glu Leu Gln Lys
            420             425             430

Asp Lys Met Ala Glu Ala Tyr Ser Glu Ile Gly Met Lys Gly Glu Arg
            435             440             445

Arg Arg Gly Lys Gly His Asp Gly Leu Tyr Gln Gly Leu Ser Thr Ala
        450             455             460

Thr Lys Asp Thr Tyr Asp Ala Leu His Met Gln Ala Leu Pro Pro Arg
465             470             475             480

<210> SEQ ID NO 32
<211> LENGTH: 531
<212> TYPE: PRT
<213> ORGANISM: Artificial sequence
<220> FEATURE:
<223> OTHER INFORMATION: Synthetic construct

<400> SEQUENCE: 32

Met Ala Leu Pro Val Thr Ala Leu Leu Leu Pro Leu Ala Leu Leu Leu
1               5               10              15

His Ala Ala Arg Pro Glu Val Gln Leu Leu Glu Ser Gly Gly Gly Leu
            20              25              30

Val Gln Pro Gly Gly Ser Leu Arg Leu Ser Cys Ala Ala Ser Gly Ile
        35              40              45

Asp Phe Ser Asn His Tyr Tyr Ile Tyr Trp Val Arg Gln Ala Pro Gly
        50              55              60

Lys Gly Leu Glu Trp Ile Gly Cys Ile Phe Ser Gly Asp Ser Ala Ser
65              70              75              80

Thr Tyr Tyr Ala Ser Trp Ala Lys Gly Arg Phe Thr Ile Ser Arg Asp
            85              90              95

Asn Ser Lys Asn Thr Leu Tyr Leu Gln Met Asn Ser Leu Arg Ala Glu
            100             105             110

Asp Thr Ala Val Tyr Tyr Cys Ala Arg Gly Met Ser Thr Asn Asp Trp
        115             120             125

Ala Ser Asp Leu Trp Gly Gln Gly Thr Leu Val Thr Val Ser Ser Gly
        130             135             140

Gly Gly Gly Ser Gly Gly Gly Gly Ser Gly Gly Gly Gly Ser Asp Ile
145             150             155             160

Gln Met Thr Gln Ser Pro Ser Ser Leu Ser Ala Ser Val Gly Asp Arg
            165             170             175

Val Thr Ile Thr Cys Gln Ala Ser Glu Ser Ile Asn Ser Ile Tyr Leu
        180             185             190

Ala Trp Tyr Gln Gln Lys Pro Gly Lys Ala Pro Lys Leu Leu Ile Tyr
        195             200             205

Arg Ala Ser Thr Leu Ala Ser Gly Val Pro Ser Arg Phe Ser Gly Ser
        210             215             220

Gly Ser Gly Thr Asp Phe Thr Leu Thr Ile Ser Ser Leu Gln Pro Glu
225             230             235             240

Asp Phe Ala Thr Tyr Tyr Cys Gln Gln Ser Tyr Asp Trp Gly Asp Val
            245             250             255

Glu Asn Thr Phe Gly Gly Gly Thr Lys Val Glu Ile Lys Thr Thr Thr
        260             265             270
```

-continued

```
Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Arg
                325                 330                 335

Ser Lys Arg Ser Arg Leu Leu His Ser Asp Tyr Met Asn Met Thr Pro
                340                 345                 350

Arg Arg Pro Gly Pro Thr Arg Lys His Tyr Gln Pro Tyr Ala Pro Pro
        355                 360                 365

Arg Asp Phe Ala Ala Tyr Arg Ser Lys Arg Gly Arg Lys Lys Leu Leu
    370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Ala Pro Ala Tyr Gln
        420                 425                 430

Gln Gly Gln Asn Gln Leu Tyr Asn Glu Leu Asn Leu Gly Arg Arg Glu
        435                 440                 445

Glu Tyr Asp Val Leu Asp Lys Arg Arg Gly Arg Asp Pro Glu Met Gly
    450                 455                 460

Gly Lys Pro Gln Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
                485                 490                 495

Gly Glu Arg Arg Arg Gly Lys Gly His Asp Gly Leu Tyr Gln Gly Leu
                500                 505                 510

Ser Thr Ala Thr Lys Asp Thr Tyr Asp Ala Leu His Met Gln Ala Leu
            515                 520                 525

Pro Pro Arg
    530
```

```
<210> SEQ ID NO 33
<211> LENGTH: 521
<212> TYPE: PRT
<213> ORGANISM: Artificial sequence
<220> FEATURE:
<223> OTHER INFORMATION: Synthetic construct

<400> SEQUENCE: 33
```

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Ser Leu Ile Ser Tyr Asp Met Tyr Trp Val Arg Gln Ala Pro Gly Lys
    50                  55                  60

Gly Leu Glu Tyr Ile Gly Ile Ile Tyr Ser Asp Gly Tyr Thr Phe Tyr
65                  70                  75                  80

Ala Thr Gly Ala Lys Gly Arg Phe Thr Ile Ser Arg Asp Asn Ser Lys
                85                  90                  95
```

-continued

```
Asn Thr Leu Tyr Leu Gln Met Asn Ser Leu Arg Ala Glu Asp Thr Ala
            100                 105                 110

Val Tyr Tyr Cys Ala Thr Asn Ala Phe Ala Leu Trp Gly Arg Gly Thr
            115                 120                 125

Leu Val Thr Val Ser Ser Gly Gly Gly Ser Gly Gly Gly Gly Ser
    130                 135                 140

Gly Gly Gly Gly Ser Ala Ile Gln Leu Thr Gln Ser Pro Ser Ser Leu
145                 150                 155                 160

Ser Ala Ser Val Gly Asp Arg Val Thr Ile Thr Cys Gln Ser Ser Gln
                165                 170                 175

Asn Val Tyr Asn Asn Asn Trp Leu Val Trp Leu Gln Gln Lys Pro Gly
            180                 185                 190

Lys Ala Pro Lys Arg Leu Ile Tyr Thr Ala Ser Ser Leu Ala Ser Gly
            195                 200                 205

Val Pro Ser Arg Phe Ser Gly Ser Gly Ser Gly Thr Asp Phe Thr Leu
    210                 215                 220

Thr Ile Ser Ser Leu Gln Pro Glu Asp Phe Ala Thr Tyr Tyr Cys Ala
225                 230                 235                 240

Gly Gly Tyr Ser Gly Pro Ile Tyr Thr Phe Gly Gly Gly Thr Lys Val
                245                 250                 255

Glu Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Lys Arg
            355                 360                 365

Gly Arg Lys Lys Leu Leu Tyr Ile Phe Lys Gln Pro Phe Met Arg Pro
    370                 375                 380

Val Gln Thr Thr Gln Glu Glu Asp Gly Cys Ser Cys Arg Phe Pro Glu
385                 390                 395                 400

Glu Glu Glu Gly Gly Cys Glu Leu Arg Val Lys Phe Ser Arg Ser Ala
                405                 410                 415

Asp Ala Pro Ala Tyr Gln Gln Gly Gln Asn Gln Leu Tyr Asn Glu Leu
            420                 425                 430

Asn Leu Gly Arg Arg Glu Glu Tyr Asp Val Leu Asp Lys Arg Arg Gly
            435                 440                 445

Arg Asp Pro Glu Met Gly Gly Lys Pro Gln Arg Arg Lys Asn Pro Gln
    450                 455                 460

Glu Gly Leu Tyr Asn Glu Leu Gln Lys Asp Lys Met Ala Glu Ala Tyr
465                 470                 475                 480

Ser Glu Ile Gly Met Lys Gly Glu Arg Arg Arg Gly Lys Gly His Asp
                485                 490                 495

Gly Leu Tyr Gln Gly Leu Ser Thr Ala Thr Lys Asp Thr Tyr Asp Ala
            500                 505                 510
```

Leu His Met Gln Ala Leu Pro Pro Arg
        515                 520

<210> SEQ ID NO 34
<211> LENGTH: 21
<212> TYPE: PRT
<213> ORGANISM: Artificial sequence
<220> FEATURE:
<223> OTHER INFORMATION: Synthetic construct

<400> SEQUENCE: 34

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 35
<211> LENGTH: 63
<212> TYPE: DNA
<213> ORGANISM: Artificial sequence
<220> FEATURE:
<223> OTHER INFORMATION: Synthetic construct

<400> SEQUENCE: 35
atctacatct gggctccact ggcaggaacc tgtggcgtgc tgctgctgtc cctggtcatc          60
aca                                                                        63

<210> SEQ ID NO 36
<211> LENGTH: 27
<212> TYPE: PRT
<213> ORGANISM: Artificial sequence
<220> FEATURE:
<223> OTHER INFORMATION: Synthetic construct

<400> SEQUENCE: 36

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 37
<211> LENGTH: 81
<212> TYPE: DNA
<213> ORGANISM: Artificial sequence
<220> FEATURE:
<223> OTHER INFORMATION: Synthetic construct

<400> SEQUENCE: 37
ttttgggtgc tggtggtggt tggtggagtc ctggcttgct atagcttgct agtaacagtg          60
gcctttatta ttttctgggt g                                                    81

<210> SEQ ID NO 38
<211> LENGTH: 41
<212> TYPE: PRT
<213> ORGANISM: Artificial sequence
<220> FEATURE:
<223> OTHER INFORMATION: Synthetic construct

<400> SEQUENCE: 38

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

-continued

```
Pro Arg Asp Phe Ala Ala Tyr Arg Ser
        35                  40

<210> SEQ ID NO 39
<211> LENGTH: 42
<212> TYPE: PRT
<213> ORGANISM: Artificial sequence
<220> FEATURE:
<223> OTHER INFORMATION: Synthetic construct

<400> SEQUENCE: 39

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 40
<211> LENGTH: 494
<212> TYPE: PRT
<213> ORGANISM: Artificial sequence
<220> FEATURE:
<223> OTHER INFORMATION: Synthetic construct

<400> SEQUENCE: 40

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Ile
        35                  40                  45

Asp Phe Ser Asn His Tyr Tyr Ile Tyr Trp Val Arg Gln Ala Pro Gly
        50                  55                  60

Lys Gly Leu Glu Trp Ile Gly Cys Ile Phe Ser Gly Asp Ser Ala Ser
65                  70                  75                  80

Thr Tyr Tyr Ala Ser Trp Ala Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Val Tyr Tyr Cys Ala Arg Gly Met Ser Thr Asn Asp Trp
            115                 120                 125

Ala Ser Asp Leu Trp Gly Gln Gly Thr Leu Val Thr Val Ser Ser Gly
        130                 135                 140

Gly Gly Gly Ser Gly Gly Gly Gly Ser Gly Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Gln Ala Ser Glu Ser Ile Asn Ser Ile Tyr Leu
            180                 185                 190

Ala Trp Tyr Gln Gln Lys Pro Gly Lys Ala Pro Lys Leu Leu Ile Tyr
            195                 200                 205

Arg Ala Ser Thr Leu Ala Ser Gly Val Pro Ser Arg Phe Ser Gly Ser
        210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ser Tyr Asp Trp Gly Asp Val
            245                 250                 255
```

-continued

```
Glu Asn Thr Phe Gly Gly Gly Thr Lys Val Glu Ile Lys Thr Thr Thr
            260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
            290                 295                 300

His Thr Arg Gly Leu Asp Phe Ala Cys Asp Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
                340                 345                 350

Tyr Met Asn Met Thr Pro Arg Arg Pro Gly Pro Thr Arg Lys His Tyr
                355                 360                 365

Gln Pro Tyr Ala Pro Pro Arg Asp Phe Ala Ala Tyr Arg Ser Arg Val
            370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
                420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
            450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

```
<210> SEQ ID NO 41
<211> LENGTH: 484
<212> TYPE: PRT
<213> ORGANISM: Artificial sequence
<220> FEATURE:
<223> OTHER INFORMATION: Synthetic construct

<400> SEQUENCE: 41

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Ser Leu Ile Ser Tyr Asp Met Tyr Trp Val Arg Gln Ala Pro Gly Lys
            50                  55                  60

Gly Leu Glu Tyr Ile Gly Ile Ile Tyr Ser Asp Gly Tyr Thr Phe Tyr
65                  70                  75                  80

Ala Thr Gly Ala Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
                100                 105                 110

Val Tyr Tyr Cys Ala Thr Asn Ala Phe Ala Leu Trp Gly Arg Gly Thr
                115                 120                 125
```

```
Leu Val Thr Val Ser Ser Gly Gly Gly Ser Gly Gly Gly Gly Ser
    130                 135                 140

Gly Gly Gly Gly Ser Ala Ile Gln Leu Thr Gln Ser Pro Ser Ser Leu
145                 150                 155                 160

Ser Ala Ser Val Gly Asp Arg Val Thr Ile Thr Cys Gln Ser Ser Gln
                165                 170                 175

Asn Val Tyr Asn Asn Asn Trp Leu Val Trp Leu Gln Gln Lys Pro Gly
                180                 185                 190

Lys Ala Pro Lys Arg Leu Ile Tyr Thr Ala Ser Ser Leu Ala Ser Gly
                195                 200                 205

Val Pro Ser Arg Phe Ser Gly Ser Gly Ser Gly Thr Asp Phe Thr Leu
    210                 215                 220

Thr Ile Ser Ser Leu Gln Pro Glu Asp Phe Ala Thr Tyr Tyr Cys Ala
225                 230                 235                 240

Gly Gly Tyr Ser Gly Pro Ile Tyr Thr Phe Gly Gly Gly Thr Lys Val
                245                 250                 255

Glu Ile Lys Thr Thr Thr Pro Ala Pro Arg Pro Pro Thr Pro Ala Pro
                260                 265                 270

Thr Ile Ala Ser Gln Pro Leu Ser Leu Arg Pro Glu Ala Cys Arg Pro
                275                 280                 285

Ala Ala Gly Gly Ala Val His Thr Arg Gly Leu Asp Phe Ala Cys Asp
    290                 295                 300

Phe Trp Val Leu Val Val Val Gly Gly Val Leu Ala Cys Tyr Ser Leu
305                 310                 315                 320

Leu Val Thr Val Ala Phe Ile Ile Phe Trp Val Arg Ser Lys Arg Ser
                325                 330                 335

Arg Leu Leu His Ser Asp Tyr Met Asn Met Thr Pro Arg Arg Pro Gly
                340                 345                 350

Pro Thr Arg Lys His Tyr Gln Pro Tyr Ala Pro Pro Arg Asp Phe Ala
                355                 360                 365

Ala Tyr Arg Ser Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
                420                 425                 430

Glu Leu Gln Lys Asp Lys Met Ala Glu Ala Tyr Ser Glu Ile Gly Met
    435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg
```

<210> SEQ ID NO 42
<211> LENGTH: 113
<212> TYPE: PRT
<213> ORGANISM: Artificial sequence
<220> FEATURE:
<223> OTHER INFORMATION: Synthetic construct

<400> SEQUENCE: 42

-continued

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
                100                 105                 110

Arg

<210> SEQ ID NO 43
<211> LENGTH: 112
<212> TYPE: PRT
<213> ORGANISM: Artificial sequence
<220> FEATURE:
<223> OTHER INFORMATION: Synthetic construct

<400> SEQUENCE: 43

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```

TARGETING LILRB4 WITH CAR-T OR CAR-NK CELLS IN THE TREATMENT OF CANCER

PRIORITY CLAIM

This application is a national phase application under 35 U.S.C. § 371 of International Application No. PCT/US2018/059362, filed Nov. 6, 2018, which claims the benefit of priority to U.S. Provisional Application Ser. Nos. 62/582,769, filed Nov. 7, 2017, 62/583,825, filed Nov. 9, 2017, and 62/584,770, filed Nov. 11, 2017, the contents of each of which are hereby incorporated by reference.

BACKGROUND

1. Technical Field

The present disclosure relates generally to the fields of medicine, immunology, cell biology, and molecular biology. In certain aspects, the field of the disclosure concerns immunotherapy. More particularly, it concerns chimeric antigen receptor (CAR) T cells and NK cells, and therapeutic methods of using such cells.

2. Background

T cells can be transduced with genetic material encoding a single chain variable fragment (scFv) of an antibody, fused to a transmembrane domain and intracellular domains containing signaling molecules or modules, to specifically recognize a cell surface antigen on a target cell type of choice in a non-MHC restricted manner. Such chimeric antigen receptor (CAR)-T cells targeting tumor-associated antigens have shown promise in the treatment of some malignancies, most notably Pre-B acute lymphoblastic leukemia. However, a major limitation to CAR-T cell therapy for the treatment of other tumors is the potential for on-target/off-tumor elimination of normal cells. To effectively utilize CAR-T cells against tumors, an antigen with high specificity for tumor cells or tumor microenvironment cells must be identified and targeted.

Natural killer (NK) cells represent an important part of innate immunity. Unlike T cells, NK cells can initiate anti-tumor cytotoxicity without prior sensitization and may potentially have fewer complications due to cytokine release syndrome, and on-target/off-tumor effects (Hermanson and Kaufman, 2015). Because of shared signaling activation mechanisms in T-cells and NK-cells, the CAR construct containing CD3-ζ activation domain can also activate NK cells (Schonfeld et al., 2015).

SUMMARY

In a first embodiment, there is provided a chimeric antigen receptor (CAR) protein, wherein the CAR protein binds LILRB4. The CAR protein may have a binding affinity to LILRB4 ($EC_{50}$ as measured by ELISA) below 1 nM, but greater than zero, such as 0.05-0.99 nM, 0.05-0.9 nM, 0.05-0.8 nM, 0.05-0.7 nM, 0.05-0.6 nM, 0.05-0.5 nM, 0.05-0.4 nM, 0.05-0.3 nM, 0.05-0.2 nM, or 0.05-0.1 nM. The CAR protein may comprise (i) VH CDRs 1-3 of SEQ ID NOS: 1-3 and VL CDRs 1-3 of SEQ ID NOS: 4-6, or (ii) VH CDRs 1-3 of SEQ ID NOS: 11-13 and VL CDRs 1-3 of SEQ ID NOS: 14-16. The CAR protein may comprise an VH amino acid sequence at least 90% identical to SEQ ID NO: 7 and a VL amino acid sequence at least 85%, 90%, 95% or 99% identical to SEQ ID NO: 9. The CAR protein may comprise an VH amino acid sequence at least 90% identical to SEQ ID NO: 7 and a VL amino acid sequence identical to SEQ ID NO: 9. The CAR protein may comprise an VH amino acid sequence at least 90% identical to SEQ ID NO: 17 and a VL amino acid sequence at least 85%, 90%, 95% or 99% identical to SEQ ID NO: 19. The CAR protein may comprise an VH amino acid sequence at least 90% identical to SEQ ID NO: 17 and a VL amino acid sequence identical to SEQ ID NO: 19. The CAR protein may comprise an amino acid sequence at least 85%, 90%, 95% or 99% identical to SEQ ID NOS: 21-23, 31-33, or 40-41. The CAR protein may comprise an amino acid sequence identical to SEQ ID NOS: 21-23, 31-33 or 40-41.

In another embodiment, there is provided a polynucleotide molecule encoding a CAR protein as described above. The polynucleotide molecule may further comprise a promoter active in eukaryotic cells. The polynucleotide may be further defined as an expression vector. Also provided is an engineered cell comprising a polynucleotide molecule encoding a chimeric antigen receptor (CAR) that binds LILRB4. The polynucleotide molecule may encode a CAR as defined above. The cell may be a T cell or an NK Cell. The cell may further comprise a transposase.

In yet another embodiment, there is provided a method of treating cancer in a human subject in need thereof comprising administering to the subject an effective amount of an engineered cell as defined above. The method may further comprise administering to said human subject a second cancer therapy, such as chemotherapy, immunotherapy, radiotherapy, hormone therapy or surgery. The second cancer therapy may be administered at the same time as the cell therapy, or administered before or after the cell therapy. The method may further comprise administering to said human subject a second administration of an effective amount of an engineered cell as defined above. The cancer may be a de novo, metastatic, recurrent, refractory or drug-resistant cancer. The cell therapy may be administered local to cancer site, region to a cancer site, or systemically. The cancer may be acute myeloid leukemia (AML). The cancer may be a hematologic malignancy such as Pre-B acute lymphoblastic leukemia (Pre-B ALL), chronic lympocytic leukemia (CLL), multiple myeloma (MM), and blastic plasmacytoid dendritic cell neoplasm (BPDCN). The cancer may be solid cancer including breast cancer, lung cancer, or prostate cancer.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-H. LILRB4 is a specific marker for monocytic AML, with normal expression restricted to cells of monocytic lineage and displays no expression on normal CD34+ hematopoietic stem cells. (FIG. 1A) Flow cytometry plot of representative patient samples for myelomonocytic AML (M4, Red) and monocytic AML (M5, Blue), demonstrates that LILRB4 is expressed by leukemia blasts in monocytic AML. (FIG. 1B) Quantified flow cytometry analysis of LILRB4 expression in 105 patients with AML demonstrates that LILRB4 is expressed on greater than 98% (SD 2.78%) of leukemia cells in patients with monocytic AML (M5). (FIGS. 1C-D) Expression of LILRB4 in normal tissue at the mRNA and protein level was assessed by gene expression analysis and mass-spectrometry proteomic analysis, respectively, showing that LILRB4 displays restricted expression on cells of the monocyte lineage. (FIGS. 1E-F) LILRB4 surface expression, evaluated by flow cytometry, is significantly increased on monocytic AML blasts (Red) as compared to paired normal monocytes (Blue). (FIG. 1G) Representative flow cytometry plot demonstrates LILRB4 is not co-expressed with CD34 on healthy human bone marrow cells. However, it does mark a sub-population of LILRB4⁺/CD34⁺ AML-M5 leukemia cells. (FIG. 1H) Flow cytometry analysis of LILRB4 expression (Red) on AML cell lines THP-1 and MV4-11 (Blue, Isotype control).

FIG. 2. Schematic representation of LILRB4 CAR constructs. $2^{nd}$ Generation CAR constructs containing CD28 or 4-1BB costimulatory domains with CD3-ζ activation domain. 3rd Generation CAR construct containing CD28 and 4-1BB co-stimulatory domains with CD3-ζ activation domain. scFv derived from anti-LILRB4 monoclonal antibody: Humanized #128-3 (scFv Hu128) and Humanized #8 (scFv Hu8).

(FIG. 3A) Following transduction, cells were selected by Puromycin treatment and expanded in culture for 2-3 weeks. LILRB4 CAR-T cells were identified by binding to LILBR4-Fc fusion protein. (FIG. 3B) Following transduction, GFP positive LILRB4 CAR-T cells display binding to LILRB4-Fc fusion protein. GFP positive cells were then sorted by flow cytometry and expanded in culture for 2-3 weeks.

FIGS. 4A-C Anti-LILRB4 CAR-T cells demonstrate potent in vitro cytotoxicity and specific cytokine release when stimulated by LILRB4⁺ AML cells. (A) Anti-LILRB4 CAR-T cells display efficient cytotoxicity against multiple LILRB4⁺ AML cell lines. AML cell lines were co-cultured with control-T cells (blue) or anti-LILRB4 CAR-T cells (red) for 4 hours at E:T ranging from 1:1 to 10:1. Cytotoxicity was determined using a flow cytometry-based assay. (B) Anti-LILRB4 CAR-T cells display efficient cytotoxicity against LILRB4⁺ primary AML samples and LILRB4⁺ normal monocytes. (C) Supernatant was collected after 24 hour co-culture of anti-LILRB4 CAR-T cells (red) or control-T cells (blue) with MV4-11 cells (E:T-1:1) and assayed for IFNγ and TNFα release by ELISA. Anti-LILRB4 CAR-T cells demonstrate significantly increased cytokine release when activated by MV4-11 AML cells, compared to control-T cells. For all panels: *p<0.05, ***p<0.001

FIGS. 5A-E. LILRB4 CAR-T cells significantly reduce leukemia burden in MV4-11 AML xenograft mouse model. Immunocompromised NSG mice were irradiated and injected with 1×10⁶ MV4-11 luciferase-expressing AML cells the following day (Day 0). Mice were treated on Day 4 with PBS, control-T cells (2×10⁶ cells/200 μl CN-T) or LILRB4 CAR-T cells (2×10⁶ cells/200 μl CAR-T). (FIG. 5A) Weekly bioluminescence imaging (BLI) of control-T cell and LILRB4 CAR-T cell treated mice. (FIG. 5B) Summary BLI data (Total flux (p/s)) demonstrates LILRB4 CAR-T cell treated mice show significantly decreased leukemia burden as compared to control-T cell treated mice. (FIG. 5C-D) Percent human leukemia blasts in peripheral blood (FIG. 5C) and bone marrow (FIG. 5D) at Day 28. LILRB4 CAR-T cell treated mice show significantly decreased circulating leukemia blasts in peripheral blood and bone marrow compared to PBS and control-T cell treated mice. (FIG. 5E) Survival analysis of MV4-11 mouse xenograft. LILRB4 CAR-T cell treated mice show significantly improved survival compared to PBS or control-T cell treated mice. *p<0.05, **p<0.01.

FIGS. 6A-D. LILRB4 is not expressed on human HSCs & anti-LILRB4 CAR-T cells have no toxicity against human HSPCs in vitro or in vivo. (FIG. 6A) Flow cytometry analysis of LILRB4 expression on human HSCs and MPPs obtained from normal-healthy adult bone marrow. Cells were gated from Low SSC/Low FSC/CD45-Dim. (FIG. 6B) UCB-CD34 cells were co-cultured with control T cells or anti-LILRB4 CAR-T cells at E:T 10:1 for 4 hours. Total cell culture was resuspended in Methocult Classic (Stemcell), plated, and colonies were counted after 10 days. No significant difference in erythroid burst forming units (BFU-E), granulocyte-colony forming unit (CFU-G), monocyte CFU-(M), CFU-GM or CFU-GEMM colony numbers, in cells treated with PBS, control (untransduced)-T cells, or anti-LILRB4 CAR-T cells. (FIGS. 6C-D) 8×10⁴ umbilical cord blood CD34⁺ (UCB-CD34) cells were transplanted into NSG mice to generate a humanized-hematopoietic reconstituted mouse model. Mice were treated with PBS (n=3) or anti-LILRB4 CAR-T cells (n=5) following engraftment and analyzed for human (FIG. 6C) CD34⁺/CD38⁻ HSC population in BM (representative mice flow cytometry plot) and (FIG. 6D) quantified for HSC (CD34⁻/CD38), myeloid (CD33), monocyte (CD14), and B-cell (CD19) populations in bone marrow, and platelet (CD41) population in peripheral blood. No difference was observed in any cell population between mice treated with anti-LILRB4 CAR-T cells and those in PBS treated conditions.

FIGS. 7A-E. LILRB4 CAR-NK shows specific cytotoxicity against AML cell lines in vitro. (FIG. 7A) LILRB4 CAR-NKL (128-41BB NKL) or control NKL (NKL) cells were co-cultured with MV4-11 cells (left panel) or THP-1 cells (right panel) at varying E:T ratio (3:1-6:1). Cytotoxicity was determined by flow cytometry as shown in representative flow plots. (FIG. 7B) Quantification of cytotoxicity of flow cytometry based assay. (FIG. 7C) Cytotoxicity assay against MV4-11, using LILRB4 CAR-NKL cells of varied constructs (8-CD28 NKL, 8-41BB NKL, 128-41BB NKL), E:T=3. (FIG. 7D) Cytotoxicity assay against THP-1, using LILRB4 CAR-NKL cells of varied constructs (8-CD28 NKL, 8-41BB NKL, 128-41BB NKL), E:T=6. (FIG. 7E) Primary LILRB4 CAR-NK (CAR128-41BB UCBNK) or control NK (UCB-NK) cells were co-cultured with THP-1 cells, E:T ratio=3. Cytotoxicity was determined by flow cytometry. * p<0.05, *** p<0.001.

FIGS. 8A-B. Cytokines release by LILRB4 CAR-NKL after stimulation with leukemia cells. (FIG. 8A) CAR-NKL (#8-CD28) cells were stimulated with MV4-11 cell, MOLM13 or MOLM13-LILRB4 KO cells at 1:1 E:T ratio for 10 h. Release of IFN-γ was detected in the culture supernatants by ELISA kit. (FIG. 8B) CAR-NKL (128-41BB) cells were stimulated with MV4-11 cell or MOLM13 at 1:1 E:T ratio for 10 h. Release of IFN-γ was detected in the culture supernatants by ELISA kit. *** p<0.001.

FIGS. 9A-D. LILRB4 CAR-NKL cells decreases leukemia engraftment in MV4-11 AML mouse xenograft model. (FIG. 9A) Schematic of in vivo xenograft experiment. (FIG. 9B) Summary BLI data, total flux (p/s). LILRB4 CAR-NKL (128-41BB CAR NKL) shows significantly decreased leukemia burden vs PBS and control NKL cell treated mice. (FIG. 9C) Percent NKL cells in peripheral blood. LILRB4 CAR NKL expanded more than control NKL cells in NSG mice engrafted with MV4-11 cells. * p<0.05. (FIG. 9D) Bioluminescence imaging of control NKL (NKL) vs LILRB4 CAR-NKL (CAR-NKL) cell treated mice at Day 37.

FIGS. 10A-D. LILRB4 CAR-NKL cells decreases leukemia burden in MV4-11 AML mouse xenograft model. (FIG. 10A) Schematic of in vivo xenograft experiment. (FIG. 10B) Bioluminescence imaging of CN-NKL vs LILRB4 CAR-NKL (#128-41BB) cell treated mice at Day 24. (FIG. 10C) Percent human leukemia blasts and NKL cells in peripheral blood at Day 29. LILRB4 CAR-NKL (#128-41BB) cell treated mice show significantly decreased circulating leukemia blasts (hCD45$^+$CD4$^+$ as the surface phenotype of MV4-11 cells) and increased NK cells (hCD45$^+$CD4$^-$ as the surface phenotype of NKL cells) in peripheral blood compared to CN-NKL cell treated mice. (FIG. 10D) LILRB4 CAR-NKL (128-41BB) cells showed significant more expansion than control NKL cells in PB in MV4-11 mouse xenograft model.

FIGS. 11 A-E. LILRB4 is a specific marker for multiple myeloma and recognized by CAR-T cells. (FIG. 11A) LILRB4 is expressed on primary multiple myeloma cells (CD38+, left panel) and myeloma cell line OPM2 and KMS26 (right panel). (FIG. 11B) LILRB4 CAR-T or control T cells were co-cultured with OPM2 cells 4 hrs (left panel) or 24 hrs (right panel). Cytotoxicity was determined by flow cytometry. (FIG. 11C) Supernatant was collected after 24-hour co-culture of LILRB4 CAR-T cells and OPM2 cells (at E:T ratio of 1:1) and assayed for tumor necrosis factor-alpha release by ELISA. LILRB4 CAR-T cells demonstrate significantly increased cytokine release when activated by OPM2 cells, compared to control T-cells (CN-T). *** p<0.001. (FIG. 11D) NSG mice were irradiated 2.5 Gy X-ray and injected with 1×10$^6$ OPM2 luciferase-expressing AML cells on the following day (Day 0). Mice were treated on Day 5 with PBS, control-T cells (1×10$^6$ cells, CN-T) or LILRB4 CAR-T cells (1×10$^6$ cells, CAR-T). Bioluminescence imaging (BLI) were conducted one month later. (FIG. 11E) Survival analysis of OPM2 mouse xenograft. LILRB4 CAR-T cell treated mice show significantly improved survival compared to PBS and control T cell treated mice.

FIGS. 12 A-F. LILRB4 is a specific marker for Pre-B ALL and recognized by CAR cells. LILRB4 is expressed on primary MLL Pre-B ALL patient samples (FIG. 12A), as well as B leukemia cell line RS4;11, KOPN8 and RCH-ACV (FIG. 12B). (FIG. 12C) LILRB4 CAR-NKL or NKL cells were co-cultured with RS4;11 cells for 4 hrs. Cytotoxicity was determined by flow cytometry. (FIG. 12D) LILRB4 CAR-NKL or NKL cells were co-cultured with KOPN8 cells (left panel) and RCH-ACV WT or RCH-ACV LILRB4 KO cells (right panel). Cytotoxicity was determined by flow cytometry 4 hrs after co-culture. (FIG. 12E) Supernatant was collected after 24-hour co-culture of LILRB4 CAR-NKL or NKL cells with pre-B ALL cells (at E:T ratio of 1:1) and assayed for IFN-γ release by ELISA. (FIG. 12F) LILRB4 CAR-T or control T cells were co-cultured with RS4;11 cells for 4 hrs. Cytotoxicity was determined by flow cytometry.  p<0.01, * p<0.001.

DESCRIPTION OF ILLUSTRATIVE EMBODIMENTS

Figure 1A:
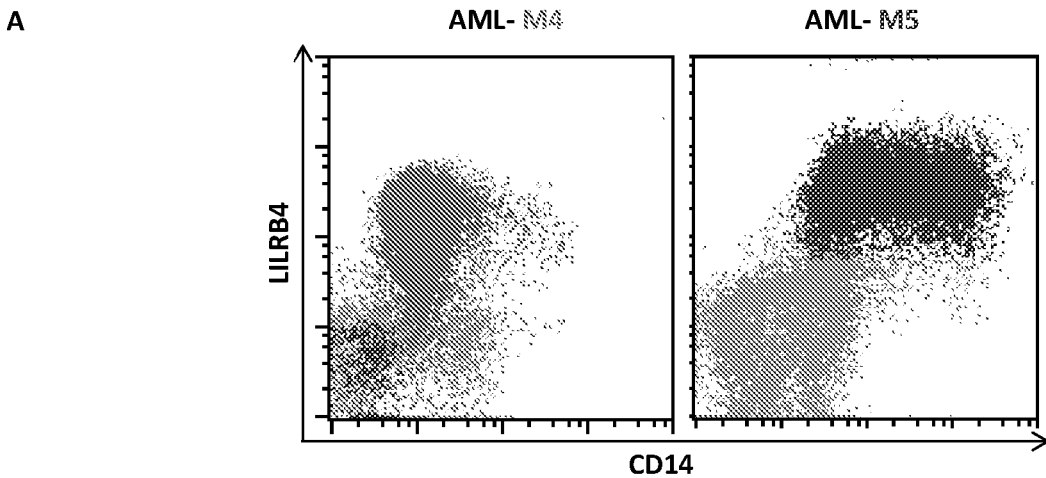

Acute myeloid leukemia (AML) has proven a difficult disease to treat, where nearly 40-60% of patients will die from relapsed or refractory disease. Conventional treatment with intensive multi-agent chemotherapy and stem cell transplant has failed to improve outcomes; therefore, novel therapeutic strategies are needed. Chimeric antigen receptor-T (CAR-T) cells directed against CD19 has proved successful in achieving and maintaining durable disease remission in Pre-B ALL; however, similar targets specifically expressed on AML leukemia cells and not on normal hematopoietic stem and progenitor cells (HSPC) have not been identified to support CAR-T treatment of AML.

Leukocyte immunoglobulin like receptor-B4 (LILRB4) is an ITIM-containing receptor, which displays restricted expression to cells of the monocytic lineage, beginning only at the pro-monocyte stage of development. The inventors have identified LILRB4 to be a tumor-associated antigen significantly upregulated in acute monocytic leukemia (FAB M4, M5) and, importantly, expressed on the leukemia stem cell population. Thus, the inventors sought to determine if LILRB4 is a good target for AML-directed CAR-T cell therapy, which could eradicate AML and its leukemia stem cells, while maintaining normal hematopoiesis.

As shown in the Examples below, the inventors generated an LILRB4-CAR, utilizing a single chain variable fragment (scFv) derived from a set of rabbit monoclonal antibodies that are subsequently humanized, with high affinity and specificity for LILRB4. This scFV was fused to either the CD28 or 4-1BB costimulatory domain, followed by CD3-ζ activation domain. This construct was expressed in primary human-T cells or the NKL cell line by lentiviral transduction. They demonstrate that LILRB4 CAR-T cells were able to specifically bind LILRB4, either on cell membrane or as LILRB4-Fc fusion protein in suspension.

Cytotoxicity was assessed by co-culture of LILRB4 CAR-T cells with leukemia cell line K562 stably expressing LILRB4, or THP-1 or MV4-11, either of which is monocytic AML cell line with endogenous LILRB4 expression. LILRB4 CAR-T cells displayed strong cytotoxic effect against all cell lines compared to control untransduced T cells, while sparing target cells negative for expression of LILRB4.

The efficacy of LILRB4 CAR-T cells was tested in vivo in an AML-mouse xenograft model. Immunocompromised NSG mice were injected with 0.5×10$^6$ MV4-11-Luciferase AML cells, followed by 1-2×10$^6$ LILRB4 CAR-T cells. Weekly bioluminescence imaging (BLI) was used to follow AML development. LILRB4 CAR-T (128-41BB) treated mice showed significantly decreased leukemia burden following treatment, compared to mice in control conditions (PBS-transduced or untransduced T cells). Additionally, CAR-T treated mice showed prolonged survival compared to mice in control conditions.

Current CAR-T cells being tested and developed for the treatment of AML have shown on-target/off-tumor toxicity toward normal HSPCs, leading to severe myelosuppression or myeloablation, as these target antigens are shared on both leukemia cells and normal stem cells. The inventors therefore assessed potential cytotoxicity of the LILRB4 CAR-T cell against normal CD34$^+$ umbilical cord blood (CD34$^+$-UCB) cells. LILRB4 was not expressed on CD34$^+$-UCB cells as determined by flow cytometry analysis. Following six-hour co-culture of CAR-T cells and CD34$^+$-UCB cells, a colony forming unit (CFU) assay was performed. Similar numbers of CFU-GM/GEMM (Granulocyte-Monocyte Colony Forming Unit) and BFU-E (Erythroid Burst Forming Unit) colonies were detected in cultures treated with control-T cells and those treated with LILRB4 CAR-T cell treated conditions. Colonies were then solubilized and analyzed by flow cytometry. No difference in CD34$^+$ or CD38$^+$ cell populations was observed under control-T cell and LILRB4 CAR-T cell treated conditions. Importantly, this demonstrates that the inventors demonstrate here that LILRB4 CAR-T cells have no in vitro toxicity toward normal human HSPCs, and therefore presents a safer alternative to current CAR-T cells for AML.

Thus, the inventors demonstrate, for the first time, the construction of a novel LILRB4 CAR-T cell which specifically targets the AML tumor associated antigen, LILRB4, leading to efficient leukemia cell killing in both in vitro and in vivo xenograft models. This work offers a new treatment strategy to improve outcomes for monocytic AML, with the potential for elimination of leukemic disease while minimizing the risk of on-target/off-tumor toxicity against normal HSPCs. These and other aspects of the disclosure are discussed in detail below.

I. Definitions

In this disclosure, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements and components comprising one unit and elements or components that comprise more than one unit unless specifically stated otherwise.

As used herein, the term "about," when used in conjunction with a percentage or other numerical amount, means plus or minus 10% of that percentage or other numerical amount. For example, the term "about 80%," would encompass 80% plus or minus 8%.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials define a term in a manner that contradicts the definition of that term in this application, this application controls.

Other objects, features, and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

As used herein, and unless otherwise indicated, the terms "disease", "disorder" or "condition" refer to a state of being or health status of a patient or subject capable of being treated with a compound, pharmaceutical composition, or method provided herein. In some embodiments, the disease is cancer (e.g. pancreatic cancer, colon cancer, gastric cancer, lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma, gastric cancer).

As used herein, and unless otherwise indicated, the terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In some embodiments, "treating" refers to the treatment of cancer.

As used herein, and unless otherwise indicated, the terms "prevent," "preventing," and "prevention" contemplate an action that occurs before a patient begins to suffer from a disorder that involves cancer that delays the onset of, and/or inhibits or reduces the severity of cancer.

As used herein, and unless otherwise indicated, the terms "manage," "managing," and "management" encompass preventing, delaying, or reducing the severity of a recurrence of a disorder such as cancer in a patient who has already suffered from such a disease, disorder or condition. The terms encompass modulating the threshold, development, and/or duration of the disorder that involves cancer or changing how a patient responds to the disorder that involves cancer.

As used herein, and unless otherwise specified, a "therapeutically effective amount" of a compound is an amount sufficient to provide any therapeutic benefit in the treatment or management of a disorder that involves electrically active cells, such as but not limited to neuronal dysfunction, a neuron mediated disorder, ocular disorder or cardiac disorder, or to delay or minimize one or more symptoms associated with a disorder that involves electrically active cells, such as but not limited to neuronal dysfunction, a neuron mediated disorder, ocular disorder or cardiac disorder. A therapeutically effective amount of a compound means an amount of the compound, alone or in combination with one or more other therapies and/or therapeutic agents that provide any therapeutic benefit in the treatment or management of a disorder that involves electrically active cells, such as but not limited to neuronal dysfunction, a neuron mediated disorder, ocular disorder or cardiac disorder.

As used herein, and unless otherwise specified, an "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of a "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing the severity or frequency of the symptom(s), or elimination of the symptom(s). The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, and unless otherwise specified, a "prophylactically effective amount" of a compound is an amount sufficient to prevent or delay the onset of cancer or one or more symptoms associated with cancer, or prevent or delay its recurrence. A prophylactically effective amount of a compound means an amount of the compound, alone or in combination with one or more other treatment and/or prophylactic agent that provides a prophylactic benefit in the prevention of a disorder such as cancer. The term "prophylactically effective amount" can encompass an amount that prevents a disorder such as cancer, improves overall prophylaxis, or enhances the prophylactic efficacy of another prophylactic agent. The "prophylactically effective amount" can be prescribed prior to, for example, the development of a disorder such as cancer.

As used herein, "patient" or "subject in need thereof" refers to a living organism suffering from or prone to a disease or condition that can be treated by administration of a composition or pharmaceutical composition as provided herein. Non-limiting examples include humans, primates, companion animals (dogs, cats, etc.), other mammals, such as but not limited to, bovines, rats, mice, monkeys, goat, sheep, cows, deer, as well as other non-mammalian animals. In some embodiments, a patient is human.

As used herein, the term "conservative substitution" generally refers to amino acid replacements that preserve the structure and functional properties of a protein or polypeptide. Such functionally equivalent (conservative substitution) peptide amino acid sequences include, but are not limited to, additions or substitutions of amino acid residues within the amino acid sequences encoded by a nucleotide sequence that result in a silent change, thus producing a functionally equivalent gene product. Conservative amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY, 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices, and materials similar or equivalent to those described herein can be used in the practice of this disclosure. The following definitions are provided to facilitate understanding of certain terms used frequently herein and are not meant to limit the scope of the present disclosure.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other functions sufficient to preserve or replicate its genomic DNA. A cell can be identified by well-known methods in the art including, for example, the presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example, mammalian, insect (e.g., *Spodoptera*) and human cells. Cells may be useful when they are naturally non-adherent or have been treated not to adhere to surfaces, for example by trypsinization.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single- and double-stranded DNA, single- and double-stranded RNA (including siRNA), and hybrid molecules having mixtures of single- and double-stranded DNA and RNA. Nucleic acid as used herein also refers to nucleic acids that have the same basic chemical structure as a naturally occurring nucleic acid. Such analogs have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogs include, without limitation, phosphorothioates, phosphoramidites, methyl phosphonates, chiral-methyl phosphonates, 2-O-methyl ribonucleotides, and peptide-nucleic acids (PNAs).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the disclosure or individual domains of the polypeptides of the disclosure), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present disclosure includes polypeptides that are substantially identical to any identified herein The word "expression" or "expressed" as used herein in reference to a gene means the transcriptional and/or translational product of that gene. The level of expression of a DNA molecule in a cell may be determined on the basis of either the amount of the corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 MOLECULAR CLONING: A LABORATORY MANUAL, 18.1-18.88. Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selective advantage to the transfected cell. Such a selective advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced into a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetization and electroporation. In some embodiments, the nucleic acid molecules are introduced into a cell using electroporation following standard procedures are well known in the art. For viral-based methods of transfection, any useful viral vector may be used in the methods described herein. Examples of viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) and Prochiantz (2007).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc. Antibodies may include antibodies that have been modified or mutated at one or more amino acid positions to improve or modulate a desired function of the antibody (e.g. glycosylation, expression, antigen recognition, effector functions, antigen binding, specificity, etc.).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high-performance liquid chromatography. A protein that is the predominant species present in a preparation is substantially purified.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer.

II. Acute Myeloid Leukemia

Acute myeloid leukemia (AML) is a cancer of the myeloid line of blood cells, characterized by the rapid growth of abnormal white blood cells that build up in the bone marrow and interfere with the production of normal blood cells. AML is the most common acute leukemia affecting adults, and its incidence increases with age. Although AML is a relatively rare disease, accounting for roughly 1.2% of cancer deaths in the United States, or 3.7 persons per 100,000 of the population, the number of cases is expected to increase as the population ages. AML also comprises approximately 15-20% of pediatric acute leukemia cases.

The symptoms of AML are caused by replacement of normal bone marrow with leukemic cells, which causes a drop in red blood cells, platelets, and normal white blood cells. These symptoms include fatigue, shortness of breath, easy bruising and bleeding, and increased risk of infection. Several risk factors and molecular and chromosomal abnormalities have been identified, but the specific cause is not clear. As an acute leukemia, AML progresses rapidly and is typically fatal within weeks or months if left untreated.

AML has several subtypes; treatment and prognosis vary among subtypes. AML is cured in 35-40% of people under 60 years old and 5-15% over 60 years old. Older people who are not able to withstand intensive chemotherapy have an average survival of 5-10 months.

AML is treated initially with chemotherapy aimed at inducing remission; people may go on to receive additional chemotherapy or a hematopoietic stem cell transplant. Recent research into the genetics of AML has resulted in the availability of tests that can predict which drug or drugs may work best for a particular person, as well as how long that person is likely to survive. The treatment and prognosis of AML differ from those of chronic myelogenous leukemia (CML) in part because the cellular differentiation is not the same; AML involves higher percentages of dedifferentiated and undifferentiated cells, including more blasts (myeloblasts, monoblasts, and megakaryoblasts).

Most signs and symptoms of AML are caused by the replacement of normal blood cells with leukemic cells. A lack of normal white blood cell production makes people more susceptible to infections; while the leukemic cells themselves are derived from white blood cell precursors, they have no infection-fighting capacity. A drop in red blood cell count (anemia) can cause fatigue, paleness, and shortness of breath, and severe or life threatening anemia may result as disease progresses. A lack of platelets can lead to easy bruising or bleeding with minor trauma and may lead to severe bleeding manifestations.

The early signs of AML are often vague and nonspecific, and may be similar to those of influenza or other common illnesses. Some generalized symptoms include fever, fatigue, weight loss or loss of appetite, shortness of breath, anemia, easy bruising or bleeding, petechiae (flat, pin-head sized spots under the skin caused by bleeding), bone and joint pain, and persistent or frequent infections.

Enlargement of the spleen may occur in AML, but it is typically mild and asymptomatic. Lymph node swelling is rare in AML, in contrast to acute lymphoblastic leukemia. The skin is involved about 10% of the time in the form of leukemia cutis. Rarely, Sweet's syndrome, a paraneoplastic inflammation of the skin, can occur with AML.

Some people with AML may experience swelling of the gums because of infiltration of leukemic cells into the gum tissue. Rarely, the first sign of leukemia may be the development of a solid leukemic mass or tumor outside of the bone marrow, called a chloroma. Occasionally, a person may show no symptoms, and the leukemia may be discovered incidentally during a routine blood test.

A number of risk factors for developing AML have been identified, including: other blood disorders, chemical exposures, ionizing radiation, and genetics.

The first clue to a diagnosis of AML is typically an abnormal result on a complete blood count. While an excess of abnormal white blood cells (leukocytosis) is a common finding with the leukemia, and leukemic blasts are sometimes seen, AML can also present with isolated decreases in platelets, red blood cells, or even with a low white blood cell count (leukopenia). While a presumptive diagnosis of AML can be made by examination of the peripheral blood smear when there are circulating leukemic blasts, a definitive diagnosis usually requires an adequate bone marrow aspiration and biopsy as well as ruling out pernicious anemia (Vitamin B12 deficiency), folic acid deficiency and copper deficiency.

Marrow or blood is examined under light microscopy, as well as flow cytometry, to diagnose the presence of leukemia, to differentiate AML from other types of leukemia (e.g., acute lymphoblastic leukemia—ALL), and to classify the subtype of disease. A sample of marrow or blood is typically also tested for chromosomal abnormalities by routine cytogenetics or fluorescent in situ hybridization. Genetic studies may also be performed to look for specific mutations in genes such as FLT3, nucleophosmin, and KIT, which may influence the outcome of the disease.

Cytochemical stains on blood and bone marrow smears are helpful in the distinction of AML from ALL, and in sub-classification of AML. The combination of a myeloperoxidase or Sudan black stain and a nonspecific esterase stain will provide the desired information in most cases. The myeloperoxidase or Sudan black reactions are most useful in establishing the identity of AML and distinguishing it from ALL. The nonspecific esterase stain is used to identify a monocytic component in AMLs and to distinguish a poorly differentiated monoblastic leukemia from ALL.

The diagnosis and classification of AML can be challenging, and should be performed by a qualified hematopathologist or hematologist. In straightforward cases, the presence of certain morphologic features (such as Auer rods) or specific flow cytometry results can distinguish AML from other leukemias; however, in the absence of such features, diagnosis may be more difficult.

The two most commonly used classification schemata for AML are the older French-American-British (FAB) system and the newer World Health Organization (WHO) system. According to the widely used WHO criteria, the diagnosis of AML is established by demonstrating involvement of more than 20% of the blood and/or bone marrow by leukemic myeloblasts, except in the three best prognosis forms of acute myeloid leukemia with recurrent genetic abnormalities (t(8;21), inv(16), and t(15;17)) in which the presence of the genetic abnormality is diagnostic irrespective of blast percent. The French-American-British (FAB) classification is a bit more stringent, requiring a blast percentage of at least 30% in bone marrow (BM) or peripheral blood (PB) for the diagnosis of AML. AML must be carefully differentiated from "preleukemic" conditions such as myelodysplastic or myeloproliferative syndromes, which are treated differently.

Because acute promyelocytic leukemia (APL) has the highest curability and requires a unique form of treatment, it is important to quickly establish or exclude the diagnosis of this subtype of leukemia. Fluorescent in situ hybridization performed on blood or bone marrow is often used for this purpose, as it readily identifies the chromosomal translocation [t(15;17)(q22;q12);] that characterizes APL. There is also a need to molecularly detect the presence of PML/RARA fusion protein, which is an oncogenic product of that translocation.

First-line treatment of AML consists primarily of chemotherapy, and is divided into two phases: induction and post-remission (or consolidation) therapy. The goal of induction therapy is to achieve a complete remission by reducing the number of leukemic cells to an undetectable level; the goal of consolidation therapy is to eliminate any residual undetectable disease and achieve a cure. Hematopoietic stem cell transplantation is usually considered if induction chemotherapy fails or after a person relapses, although transplantation is also sometimes used as front-line therapy for people with high-risk disease. Efforts to use tyrosine kinase inhibitors in AML continue.

All FAB subtypes except M3 are usually given induction chemotherapy with cytarabine (ara-C) and an anthracycline (most often daunorubicin). This induction chemotherapy regimen is known as "7+3" (or "3+7"), because the cytarabine is given as a continuous IV infusion for seven consecutive days while the anthracycline is given for three consecutive days as an IV push. Up to 70% of people with AML will achieve a remission with this protocol. Other alternative induction regimens, including high-dose cytarabine alone, FLAG-like regimens or investigational agents, may also be used. Because of the toxic effects of therapy, including myelosuppression and an increased risk of infection, induction chemotherapy may not be offered to the very elderly, and the options may include less intense chemotherapy or palliative care. Pediatric AML is treated similarly with a common regimen consisting of a backbone of cytarabine and anthracylcine containing chemotherapy in addition to etoposide.

The M3 subtype of AML, also known as acute promyelocytic leukemia (APL), is almost universally treated with the drug all-trans-retinoic acid (ATRA) in addition to induction chemotherapy, usually an anthracycline. Care must be taken to prevent disseminated intravascular coagulation (DIC), complicating the treatment of APL when the promyelocytes release the contents of their granules into the peripheral circulation. APL is eminently curable, with well-documented treatment protocols.

The goal of the induction phase is to reach a complete remission. Complete remission does not mean the disease has been cured; rather, it signifies no disease can be detected with available diagnostic methods. Complete remission is obtained in about 50%-75% of newly diagnosed adults, although this may vary based on the prognostic factors described above. The length of remission depends on the prognostic features of the original leukemia. In general, all remissions will fail without additional consolidation therapy.

Even after complete remission is achieved, leukemic cells likely remain in numbers too small to be detected with current diagnostic techniques. If no further postremission or consolidation therapy is given, almost all people with AML will eventually relapse. Therefore, more therapy is necessary to eliminate nondetectable disease and prevent relapse—that is, to achieve a cure.

The specific type of post-remission therapy is individualized based on a person's prognostic factors (see above) and general health. For good-prognosis leukemias (i.e., inv(16), t(8;21), and t(15;17)), people will typically undergo an additional three to five courses of intensive chemotherapy, known as consolidation chemotherapy. For people at high risk of relapse (e.g., those with high-risk cytogenetics, underlying MDS, or therapy-related AML), allogeneic stem cell transplantation is usually recommended if the person is able to tolerate a transplant and has a suitable donor. The best post-remission therapy for intermediate-risk AML (normal cytogenetics or cytogenetic changes not falling into good-risk or high-risk groups) is less clear and depends on the specific situation, including the age and overall health of the person, the person's values, and whether a suitable stem cell donor is available.

For people who are not eligible for a stem cell transplant, immunotherapy with a combination of histamine dihydrochloride (Ceplene) and interleukin 2 (Proleukin) after the completion of consolidation has been shown to reduce the absolute relapse risk by 14%, translating to a 50% increase in the likelihood of maintained remission.

For people with relapsed AML, the only proven potentially curative therapy is a hematopoietic stem cell transplant, if one has not already been performed. In 2000, the monoclonal antibody-linked cytotoxic agent gemtuzumab ozogamicin (Mylotarg®) was approved in the United States for people aged more than 60 years with relapsed AML who are not candidates for high-dose chemotherapy. This drug was voluntarily withdrawn from the market by its manufacturer, Pfizer in 2010 before returning to market again in 2017 with a different label (a lower recommended dose, a different schedule in combination with chemotherapy or on its own, and a new patient population). Since treatment options for relapsed AML are so limited, palliative care or enrollment in a clinical trial may be offered. For relapsed acute promyelocytic leukemia (APL), arsenic trioxide is approved by the US FDA. Like ATRA, arsenic trioxide does not work with other subtypes of AML.

III. Chimeric Antigen Receptors

"Chimeric antigen receptors" (CARs), as used herein, refer to engineered receptors that are capable of grafting a desired specificity to an antigen into immune effector cells, such as T cells and NK cells. Typically, a CAR protein comprises an extracellular domain that introduces the desired specificity, a transmembrane domain and an intracellular domain that transmits a signal to the immune effector cells when the immune effector cells bind to the antigen. In certain embodiments, the extracellular domain comprises a leader peptide, an antigen recognition region and a spacer region. In certain embodiments, the antigen recognition region is derived from an antibody that specifically binds to the antigen. In certain embodiments, the antigen recognition region is a single-chain variable fragment (scFv) derived from the antibody. In certain embodiments, the single-chain variable fragment (scFv) is derived from a humanized antibody (HuCAR scFv). In certain embodiment, the single-chain variable fragment comprises a heavy chain variable region fused to a light chain variable region through a flexible linker.

The term "leader peptide" as referred to herein is used according to its ordinary meaning in the art and refers to a peptide having a length of about 5-30 amino acids. A leader peptide is present at the N-terminus of newly synthesized proteins that form part of the secretory pathway. Proteins of the secretory pathway include, but are not limited to proteins that reside either inside certain organelles (the endoplasmic reticulum, Golgi or endosomes), are secreted from the cell, or are inserted into a cellular membrane. In some embodiments, the leader peptide forms part of the transmembrane domain of a protein.

In one aspect, the present disclosure provides a CAR protein that binds LILRB4 (LILRB4 CAR protein). LILRB4 is the antigen, and the chimeric antigen receptor (or CAR protein) is an antibody against LILRB4, or a binding fragment that recognizes LILRB4, in the context of other membrane and intracellular components. In some embodiments, the anti-LILRB4 antibody or LILRB4-binding fragment is humanized, and the CAR protein comprising such humanized antibody or fragment may be referred to as "LILRB4 HuCAR". In some embodiments, the LILRB4 CAR protein includes from the N-terminus to the C-terminus: a leader peptide, an anti-LILRB4 heavy chain variable domain, a linker domain, an anti-LILRB4 light chain variable domain, a CD8a hinge region, a CD8a transmembrane domain (or a CD28 transmembrane domain), a 4-1BB intracellular co-stimulatory signaling domain (or a CD28 intracellular co-stimulatory signaling domain, or a CD28 intracellular co-stimulatory signaling domain followed by a 4-1BB intracellular co-stimulatory signaling domain) and a CD3-ζ intracellular T cell signaling domain in one of two isoforms (CD3zIso1 or CD3zIso3).

In some embodiments, the protein includes from the N-terminus to the C-terminus: a CD8a leader peptide, a LILRB4 HuCAR scFv, a human CD8a hinge domain, a CD28 transmembrane domain and intracellular co-stimulatory signaling domain, and the zeta (ζ) chain of the human CD3 complex T-cell signaling domain.

In some embodiments, the protein includes from the N-terminus to the C-terminus: a CD8a leader peptide, a LILRB4 HuCAR scFv, a human CD8a hinge domain and transmembrane domain, a CD28 intracellular co-stimulatory signaling domain, and the zeta (ζ) chain of the human CD3 complex T-cell signaling domain.

In other embodiments, the protein includes from the N-terminus to the C-terminus: a CD8a leader peptide, a LILRB4 HuCAR scFv, a human CD8a hinge domain and transmembrane domain, a 4-1BB intracellular co-stimulatory signaling domain, and the zeta (ζ) chain of the human CD3 complex T-cell signaling domain.

In an alternative embodiment, the protein includes from the N-terminus to the C-terminus: a CD8a leader peptide, a LILRB4 HuCAR scFv, a human CD8a hinge domain and transmembrane domain, a CD28 intracellular co-stimulatory signaling domain, a 4-1BB intracellular co-stimulatory signaling domain, and the zeta (ζ) chain of the human CD3 complex T-cell signaling domain.

In another embodiment, the protein includes from the N-terminus to the C-terminus: a leader peptide, an anti-LILRB4 heavy chain variable domain, a linker domain, an anti-LILRB4 light chain variable domain, a human IgG1-CH2-CH3 domain, a spacer region, a CD28 transmembrane domain, a 4-1BB intracellular co-stimulatory signaling and the zeta (ζ) chain of the human CD3 complex T-cell signaling domain.

In some embodiments, the construct comprises the nucleic acid sequence shown within the vector pLVX- EF1alpha-IRES-ZsGreen from Clontech, or pSIN-EF1alpha-IRES-Puromycin or pSIN-EF1alpha (with IRES-Puromycin removed), and designed CAR-128-CD28 (SEQ ID NO: 21, SEQ ID NO: 40), CAR-128-41BB (SEQ ID NO: 22), CAR-8-CD28 (SEQ ID NO: 23, SEQ ID NO: 41), CAR-8-41BB (SEQ ID NO: 31), CAR-128-CD28-41BB (SEQ ID NO: 32), CAR-8-CD28-41BB (SEQ ID NO: 33) (see Table 2).

In some embodiments, the nucleic acid encodes the antibody heavy chain variable domain and the antibody light chain variable domain from an antibody that binds LILRB4.

In another aspect, an expression vector including a nucleic acid provided herein including embodiments thereof is provided. In another aspect, a T lymphocyte including the expression vector provided herein including embodiments thereof is provided. In another aspect, a mammalian cell including the expression vector provided herein including embodiments thereof is provided. In another aspect, a recombinant protein is provided. The recombinant protein includes (i) an antibody region including a central cavity formed by a heavy chain variable (VH) region and a light chain variable (VL) region, wherein the central cavity forms a peptide binding site including framework region amino acid residues; and (ii) a transmembrane domain.

In another aspect, a recombinant protein is provided. The recombinant protein includes a first portion including an antibody heavy chain variable domain and a second portion including an antibody light chain variable domain and an antibody light chain constant domain, wherein the first portion further includes a transmembrane domain, and wherein the antibody heavy chain variable domain, the antibody light chain variable domain and the antibody light chain constant domain together form an antibody region.

In another aspect, a recombinant protein is provided. The recombinant protein includes a first portion including an antibody heavy chain variable domain and a second portion including an antibody light chain variable domain, wherein the first portion further includes a transmembrane domain, and wherein the antibody heavy chain variable domain and the antibody light chain variable domain together form an antibody region.

In another aspect, a recombinant protein is provided. The recombinant protein includes a first portion including an antibody heavy chain variable domain and an antibody heavy chain constant domain, and a second portion including an antibody light chain variable domain, wherein the first portion further includes a transmembrane domain, and wherein the antibody heavy chain variable domain, the antibody heavy chain constant domain and the antibody light chain variable domain together form an antibody region.

In another aspect, a recombinant protein is provided. The recombinant protein includes a first portion including an antibody heavy chain variable domain and a second portion including an antibody light chain variable domain and an antibody light chain constant domain, wherein the second portion further includes a transmembrane domain, and wherein the antibody heavy chain variable domain, the antibody light chain variable domain and the antibody light chain constant domain together form an antibody region.

In another aspect, a recombinant protein is provided. The recombinant protein includes a first portion including an antibody heavy chain variable domain and a second portion including an antibody light chain variable domain, wherein the second portion further includes a transmembrane domain, and wherein the antibody heavy chain variable domain and the antibody light chain variable domain together form an antibody region.

In another aspect, a mammalian cell including the recombinant protein provided herein including embodiments thereof is provided, wherein the transmembrane domain is within the cell membrane of the mammalian cell.

In some embodiments, the transmembrane domain is a CD8α transmembrane domain. The term "CD8α transmembrane domain" as provided herein includes any of the recombinant or naturally-occurring forms of the transmembrane domain of CD8a. In some aspects, the variants or homologs have at least 90%, 95%, 96%, 97%, 98%, 99% or 100% amino acid sequence identity across the whole sequence or a portion of the sequence compared to a naturally occurring CD8α transmembrane domain polypeptide. In some embodiments, the CD8α transmembrane domain has the polypeptide sequence of IYIWAPLAGTCGVLLLSLVIT (SEQ ID NO: 34). In some embodiments, the CD8α transmembrane domain is the protein encoded by the nucleic acid sequence of ATCTACATCTGGGCTCCACTGGCAG-GAACCTGTGGCGTGCTGCTGCTGTCCCTGG TCATCACA (SEQ ID NO: 35).

In some embodiments, the transmembrane domain is a CD28 transmembrane domain. The term "CD28 transmembrane domain" as provided herein includes any of the recombinant or naturally-occurring forms of the transmembrane domain of CD28, or variants or homologs thereof that maintain CD28 transmembrane domain activity. In some aspects, the variants or homologs have at least 90%, 95%, 96%, 97%, 98%, 99% or 100% amino acid sequence identity across the whole sequence or a portion of the sequence compared to a naturally occurring CD28 transmembrane domain polypeptide. In some embodiments, the CD28 transmembrane domain has the polypeptide sequence of FWVLVVVGGVLACYSLLVTVAFIIFWV (SEQ ID NO: 36). In some embodiments, the CD28 transmembrane domain is the protein encoded by the nucleic acid sequence of TTTTGGGTGCTGGTGGTGGTTGGTG-GAGTCCTGGCTTGCTATAGCTTGCTAGTAA CAGTGGCCTTTATTATTTTCTGGGTG (SEQ ID NO: 37).

In some embodiments, the intracellular T cell signaling domain is a CD3-ζ intracellular T cell signaling domain. In some embodiments, the intracellular T cell signaling domain includes the signaling domain of the zeta (ζ) chain of the human CD3 complex. In some embodiments, the intracellular T cell signaling domain is a CD3-ζ intracellular T cell signaling domain. In some embodiments, the intracellular T cell signaling domain is the protein CD3zIso1 with the amino acid sequence of RVKFSRSADAPAYQQGQNQLY-NELNLGRRREEYDVLDKRRGRDPEMGGKPQRRKNP QEGLYNELQKDKMAEAYSEIGMKGERRRGKGHDG-LYQGLSTATKDTYDALHMQA LPPR (SEQ ID No: 42). In some embodiments, the intracellular T cell signaling domain is the protein CD3zIso3 with the amino acid sequence of RVKFSRSADAPAYQQGQNQLYNELNLGR-REEYDVLDKRRGRDPEMGGKPRRKNPQ EGLY-NELQKDKMAEAYSEIGMKGERRRGKGHDGLYQGL-STATKDTYDALHMQAL PPR (SEQ ID No: 43), encoded by the nucleic acid sequence of AGAGT-GAAGTTCAGCAGGAGCGCA-GACGCCCCCGCGTACCAGCAGGGCCAGAA CCAGCTCTATAACGAGCT-CAATCTAGGACGAAGAGAGGAGTAC-GATGTTTTGGA CAAGAGACGTGGCCGGGACCCT-GAGATGGGGGGAAAGCCGAGAAGGAAGAACC CTCAGGAAGGCCTGTACAATGAACTGCAGAAAGA-TAAGATGGCGGAGGCCTACA GTGAGATTGGGAT- GAAAGGCGAGCGCCGGAGGGGCAAGGGGCAC-
GATGGCCTT
TACCAGGGTCTCAGTACAGCCACCAAGGACACC-
TACGACGCCCTTCACATGCAG
GCCCTGCCCCCTCGCTAA (SEQ ID NO: 29).

In some embodiments, the isolated nucleic acid provided
herein includes an intracellular co-stimulatory signaling
sequence encoding an intracellular co-stimulatory signaling
domain. An "intracellular co-stimulatory signaling domain"
as provided herein includes amino acid sequences capable of
providing co-stimulatory signaling in response to binding of
an antigen to the antibody region provided herein including
embodiments thereof. In some embodiments, the signaling
of the co-stimulatory signaling domain results in the pro-
duction of cytokines and proliferation of the T cell express-
ing the same. In some embodiments, the intracellular co-
stimulatory signaling domain is a CD28 intracellular
co-stimulatory signaling domain, a 4-1BB intracellular co-
stimulatory signaling domain. In some embodiments, the
intracellular co-stimulatory signaling domain includes a
CD28 intracellular co-stimulatory signaling domain, a
4-1BB intracellular co-stimulatory signaling domain, an
ICOS intracellular co-stimulatory signaling domain, an
OX-40 intracellular co-stimulatory signaling domain or any
combination thereof. In some embodiments, the CD28 co-
stimulating domain has the polypeptide sequence of
RSKRSRLLHSDYMNMTPRRPGPTRKHYQPYAPPRD-
FAAYRS (SEQ ID NO: 38). In some embodiments, the
CD28 intracellular co-stimulatory signaling domain is the
protein encoded by the nucleic acid sequence of
AGGAGTAAGAGGAGCAGGCTCCTGCACAGTGAC-
TACATGAACATGACTCCCCGC CGCCCCGGGCC-
CACCCGCAAGCATTACCAGCCCTATGCCCCAC-
CACGCGACTTCG CAGCCTATCGCTCC (SEQ ID NO:
27). In some embodiments, the 4-1BB intracellular co-
stimulatory signaling domain has the polypeptide sequence
of KRGRKKLLY-
IFKQPFMRPVQTTQEEDGCSCRFPEEEEGGCEL (SEQ
ID NO: 39). In some embodiments, the 4-1BB intracellular
co-stimulatory signaling domain is the protein encoded by
the nucleic acid sequence of
AAACGGGGCAGAAAGAAACTCCTGTATATATT-
CAAACAACCATTTATGAGACCA GTACAAACTACT-
CAAGAGGAAGATGGCTGTAGCTGCCGAT-
TTCCAGAAGAAGAA GAAGGAGGATGTGAACTG
(SEQ ID NO: 28).

In some embodiments, the isolated nucleic acid provided
herein includes a spacer sequence encoding a spacer region.
A "spacer region" as provided herein is a polypeptide
connecting the antibody region with the transmembrane
domain, or connecting various components of the antibody
region. In some embodiments, the spacer region is between
the antibody region and the transmembrane domain. In some
embodiments, the spacer region connects the heavy chain
variable region with the transmembrane domain. In some
embodiments, the spacer region connects the heavy chain
constant region with the transmembrane domain. In some
embodiments, the spacer region connects the light chain
variable region with the transmembrane domain. In some
embodiments, the spacer region connects the light chain
constant region with the transmembrane domain. In some
embodiments, the binding affinity of the antibody region to
an antigen is increased compared to the absence of the
spacer region. In some embodiments, the steric hindrance
between an antibody region and an antigen is decreased in
the presence of the spacer region.

In some embodiments, the spacer region includes a hinge
region. In some embodiments, the hinge region is a CD8α
hinge region. In some embodiments, the hinge region is a
CD28 hinge region.

In some embodiments, the spacer region includes a Fc
region. Examples of spacer regions contemplated for the
compositions and methods provided herein include without
limitation, immunoglobulin molecules or fragments thereof
(e.g., IgG1, IgG2, IgG3, IgG4) and immunoglobulin mol-
ecules or fragments thereof (e.g., IgG1, IgG2, IgG3, IgG4)
including mutations affecting Fc receptor binding. In some
embodiments, the spacer region is a fragment of an IgG
(e.g., IgG4), wherein said fragment includes a deletion of the
CH2 domain. The spacer region may be a peptide linker. In
some embodiments, the nucleic acid does not include a
spacer sequence encoding a spacer region.

In some embodiments, the spacer region connects various
components of the antibody region. In some embodiments,
the spacer region connects the heavy chain variable region
with the light chain variable region.

In some embodiments, the isolated nucleic acid provided
herein includes a linker sequence encoding a linker domain.
In some embodiment, the linker domain is inserted between
the VH and VL of the scFv. In some embodiments, the linker
domain is between the transmembrane domain and the
intracellular T cell signaling domain. In some embodiments,
the linker domain is between the intracellular T cell signal-
ing domain and the intracellular co-stimulatory signaling
domain. In some embodiments, the linker domain comprises
the sequence GGGGSGGGGSGGGGS (SEQ ID NO: 25).

In some embodiments, the isolated nucleic acid provided
herein does not include a linker sequence encoding a linker
domain.

In some embodiments, the nucleic acid includes (i) a
heavy chain sequence encoding a heavy chain domain of the
protein, the heavy chain domain includes a variable heavy
chain domain and the transmembrane domain; and (ii) a
light chain sequence encoding a light chain domain of the
protein, the light chain domain includes a variable light
chain domain, wherein the variable heavy chain domain and
the variable light chain domain together form at least a
portion of the antibody region.

In some embodiments, the nucleic acid includes (i) a
heavy chain sequence encoding a heavy chain domain of the
protein, the heavy chain domain includes a variable heavy
chain domain; and (ii) a light chain sequence encoding a
light chain domain of the protein, the light chain domain
includes a variable light chain domain and a transmembrane
domain, wherein the variable heavy chain domain and the
variable light chain domain together form at least a portion
of the antibody region.

A "heavy chain sequence" as provided herein refers to the
nucleic acid sequence encoding for a heavy chain domain
provided herein. A heavy chain domain provided herein may
include heavy chain variable (VH) region and/or a heavy
chain constant region (CH). A "light chain sequence" as
provided herein refers to the nucleic acid sequence encoding
for a light chain domain provided herein. A light chain
domain provided herein may include a light chain variable
(VL) region and/or a light chain constant region (CL). The
term "heavy chain domain" as referred to herein is used
according to its ordinary meaning in the art and refers to a
polypeptide including a heavy chain variable (VH) region
and a heavy chain constant region (CH). The term "light
chain domain" as referred to herein is used according to its
ordinary meaning in the art and refers to a polypeptide
including a light chain variable (VL) region and a light chain constant region (CL). In some embodiments, the antibody heavy chain variable domain and the antibody light chain variable domain are humanized.

In some embodiments, the protein or antibody region provided herein including embodiments thereof competes for antigen binding with, specifically binds to the same antigen or epitope as, and/or contains one, more, or all CDRs (or CDRs comprising at least at or about 75, 80, 85, 90, 91, 92, 93, 94, 95, 96, 97, 98, or 99% identity to the CDRs), e.g., including a heavy chain CDR 1, 2, and/or 3 and/or a light chain CDR1, 2, and/or 3, of antibody that bind LILRB4.

In some embodiments, the nucleic acid encodes the antibody heavy chain variable domain and the antibody light chain variable domain from an antibody that binds LILRB4. In some embodiments, the nucleic acid encoding the antibody heavy chain variable domain is identified by SEQ ID NO: 8 or SEQ ID NO: 18 (see Table 1). In some embodiments, the nucleic acid encoding the antibody light chain variable domain is identified by SEQ ID NO: 10 or SEQ ID NO: 20 (see Table 1).

In some embodiments, the protein includes an intracellular co-stimulatory signaling domain and a CD3-ζ intracellular T cell signaling domain. In some embodiments, the protein includes from the amino terminus to the carboxyl terminus: a heavy chain variable domain, a light chain variable domain, a transmembrane domain, an intracellular co-stimulatory signaling domain and a CD3-ζ intracellular T cell signaling domain.

In some embodiments, the protein includes an intracellular co-stimulatory signaling domain and a CD3-ζ intracellular T cell signaling domain. In some embodiments, the protein includes from the amino terminus to the carboxyl terminus: a light chain variable domain, a heavy chain variable domain, a transmembrane domain, an intracellular co-stimulatory signaling domain and a CD3-ζ intracellular T cell signaling domain.

In some embodiments, the recombinant protein includes a first portion including an antibody heavy chain variable domain and a second portion including an antibody light chain variable domain. In some embodiments, the first portion includes an intracellular co-stimulatory signaling domain and a CD3-ζ intracellular T cell signaling domain. In some embodiments, the first portion includes from the amino terminus to the carboxyl terminus: a heavy chain variable domain, a transmembrane domain, an intracellular co-stimulatory signaling domain and a CD3-ζ intracellular T cell signaling domain.

In some embodiments, the recombinant protein includes a first portion including an antibody heavy chain variable domain and a heavy chain constant domain, and a second portion including an antibody light chain variable domain. In some embodiments, the first portion includes an intracellular co-stimulatory signaling domain and a CD3-ζ intracellular T cell signaling domain. In some embodiments, the first portion includes from the amino terminus to the carboxyl terminus: the heavy chain variable domain, a heavy chain constant domain, a transmembrane domain, an intracellular co-stimulatory signaling domain and a CD3-ζ intracellular T cell signaling domain.

In some embodiments, the protein includes a CD3-ζ intracellular T cell signaling domain and intracellular co-stimulatory signaling domain. In some embodiments, the protein includes from the amino terminus to the carboxyl terminus: a heavy chain variable domain, a light chain variable domain, a transmembrane domain, a CD3-ζ intracellular T cell signaling domain and an intracellular co-stimulatory signaling domain.

In some embodiments, the recombinant protein includes a first portion including an antibody heavy chain variable domain and a second portion including an antibody light chain variable domain. In some embodiments, the first portion includes a CD3-ζ intracellular T cell signaling domain and intracellular co-stimulatory signaling domain. In some embodiments, the first portion includes from the amino terminus to the carboxyl terminus: a heavy chain variable domain, a transmembrane domain, a CD3-ζ intracellular T cell signaling domain and an intracellular co-stimulatory signaling domain.

In some embodiments, the recombinant protein includes a first portion including an antibody heavy chain variable domain and a heavy chain constant domain, and a second portion including an antibody light chain variable domain. In some embodiments, the first portion includes a CD3-ζ intracellular T cell signaling domain and intracellular co-stimulatory signaling domain. In some embodiments, the first portion includes from the amino terminus to the carboxyl terminus: a heavy chain variable domain, a heavy chain constant domain, a transmembrane domain, a CD3-ζ intracellular T cell signaling domain and an intracellular co-stimulatory signaling domain.

In some embodiments, the isolated nucleic acid encodes a protein from the N-terminus to the C-terminus: a leader peptide, an anti-LILRB4 heavy chain variable domain, a linker domain, an anti-LILRB4 light chain variable domain, a human IgG1-CH2-CH3 domain, a spacer region, a CD28 transmembrane domain, a 4-1BB intracellular co-stimulatory signaling domain and a CD3-ζ intracellular T cell signaling domain.

In some embodiments, the isolated nucleic acid encodes a protein from the N-terminus to the C-terminus: a leader peptide, an anti-LILRB4 heavy chain variable domain, a linker domain, an anti-LILRB4 light chain variable domain, a spacer region, a CD28 transmembrane domain, a 4-1BB intracellular co-stimulatory signaling domain and a CD3-ζ intracellular T cell signaling domain.

In some embodiments, the isolated nucleic acid encodes a protein from the N-terminus to the C-terminus: a leader peptide, an anti-LILRB4 heavy chain variable domain, a linker domain, an anti-LILRB4 light chain variable domain, a spacer region, a CD28 transmembrane and co-stimulatory domain, and a CD3-ζ intracellular T cell signaling domain.

In some embodiments, the isolated nucleic acid encodes a protein from the N-terminus to the C-terminus: a leader peptide, an anti-LILRB4 heavy chain variable domain, a linker domain, an anti-LILRB4 light chain variable domain, a spacer region, a CD8α transmembrane domain (or a CD28 transmembrane domain), a 4-1BB intracellular co-stimulatory signaling domain (or a CD28 intracellular co-stimulatory signaling domain) and a CD3-ζ intracellular T cell signaling domain.

In some embodiments, the protein includes from the N-terminus to the C-terminus: a leader peptide encoded by the nucleic acid of ATGGCCT-TACCAGTGACCGCCTTGCTCCTGCCGCTGGCCTTG-CTGCTCCACGCCG CCAGGCCG (SEQ ID NO: 24), an anti-LILRB4 heavy chain variable domain encoded by the nucleic acid of SEQ ID NO: 8 or SEQ ID NO: 18 (see Table 1), a linker domain encoded by the nucleic acid of GGTG-GAGGCGGTTCAGGTGGCGGCGGTTCGGGCGGTGG-CGGCTCT (SEQ ID NO: 30), an anti-LILRB4 light chain variable domain encoded by the nucleic acid of SEQ ID NO: 10 or SEQ ID NO: 20 (see Table 1), a hinge region encoded by the nucleic acid of ACCACGACGCCAGCGCCGCGACCAC- CAACACCGGCGCCCACCATCGCGTCGCAG
CCCCTGTCCCTGCGCCCAGAGGCGTGCCGGCCAG-
CGGCGGGGGGCGCAGTGCAC
ACGAGGGGGCTGGACTTCGCCTGTGAT (SEQ ID NO: 26), a CD28 intracellular co-stimulatory signaling domain encoded by the nucleic acid of SEQ ID NO: 27; a 4-1BB intracellular co-stimulatory signaling domain encoded by the nucleic acid of SEQ ID NO: 28 and a CD3-ζ intracellular T cell signaling domain encoded by the nucleic acid of SEQ ID NO: 29.

In some embodiments, an isolated nucleic acid molecule provided comprises SEQ ID NO: 24 which encodes a leader peptide, SEQ ID NO: 8 or SEQ ID NO: 18 (see Table 1) which encodes an anti-LILRB4 heavy chain variable domain, SEQ ID NO: 30 which encodes a linker domain, SEQ ID NO: 10 or SEQ ID NO: 20 (see Table 1) which encodes an anti-LILRB4 light chain variable domain, SEQ ID NO: 26 which encodes a hinge region, SEQ ID NO: 27 which encodes a CD28 intracellular co-stimulatory signaling domain, SEQ ID NO: 28 which encodes a 4-1BB intracellular co-stimulatory signaling domain, and SEQ ID NO: 29 which encodes a CD3-ζ intracellular T cell signaling domain.

In certain embodiments, the LILRB4 CAR protein provided herein demonstrates a high affinity to LILRB4. In certain embodiments, the CAR protein provided herein has a binding affinity to LILRB4 ($EC_{50}$ as measured by ELISA) of less than 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM or 0.05 nM. For the purposes of this application, ELISA $EC_{50}$ values may be determined as follows. LILRB-4 extracellular domain protein (with 6 HIS tag at the C-terminus) was produced recombinantly in HEK293 cells and coated onto a high binding 96-well clear plate (Corning-Costar, Fisher Scientific) at 1 μg/ml concentration (100 μl/well) at 4° C. for 14 to 16 hours. The coated plates were washed with PBS, pH 7.4, briefly and blocked with 200 μl/well of 5% non-fat milk in PBS for 2 hour at 37° C. Serial dilutions of the testing monoclonal antibodies (IgGs or scFvs fragments), starting from 10 μg/ml and 3-fold titration down for 12 steps, were added to the 96-well plate for binding by incubating 45 minutes at 37° C. with a cover on the assay plate. Then the plates were washed with PBS containing Tween 20 (0.05% concentration) for 3 times and PBS one time. Secondary antibody of anti-human or anti-rabbit, or other species IgG specific antibodies with HRP conjugate (Jackson ImmunoResearch) was added for incubation at room temperature for 1 hour per manufacturer's suggested dilution. Detection was conducted by adding HRP substrate, TMB (ThermoFisher) for 10 minutes, and stopped by adding 50 μl/well of 2N 142504. The plates were read for absorbance at 450 nm using a plate reader (SpectraMax M4, Molecular Devices). Data were collected and graphed using a 4-parameter fitting curve with GraphPad Prism 7 software for $EC_{50}$ calculation.

In another aspect, a T lymphocyte including the recombinant protein provided herein including embodiments thereof is provided, wherein the transmembrane domain is within the cell membrane of the T lymphocyte.

In another aspect, a method of treating cancer is provided. The method includes administering to a subject in need thereof an effective amount of a mammalian cell provided herein including embodiments thereof, wherein the antibody region is an anti-cancer antibody region. In another aspect, a method of treating cancer is provided. The method includes administering to a subject in need thereof an effective amount of the T-lymphocyte provided herein including embodiments thereof, wherein the antibody region is an anti-cancer antibody region. In another aspect, a method of reprogramming a T lymphocyte is provided. The method includes contacting a T lymphocyte with the expression vector provided herein including embodiments thereof. In another aspect, a method of detecting a cancer is provided. The method includes (i) administering to a cancer patient an effective amount of a T lymphocyte including the recombinant protein provided herein including embodiments thereof and a compound including a peptidyl moiety capable of binding to the peptide binding site, wherein the compound further includes a detectable label, and wherein the antibody region is an anti-cancer antibody region. The method includes (ii) allowing the compound to bind to the peptide binding site thereby forming a recombinant protein-compound complex. And (iii) the recombinant protein-compound complex is detected within the cancer patient thereby detecting the cancer.

IV. Host Cells

Certain embodiments of the present disclosure concern immune cells which express a chimeric antigen receptor (CAR). The immune cells may be T cells (e.g., regulatory T cells, CD4+ T cells, CD8+ T cells, or gamma-delta T cells), Natural Killer (NK) cells, invariant NK cells, or NKT cells. Also provided herein are methods of producing and engineering the immune cells as well as methods of using and administering the cells for adoptive cell therapy, in which case the cells may be autologous or allogeneic. Thus, the immune cells may be used as immunotherapy, such as to target cancer cells.

The immune cells may be isolated from subjects, particularly human subjects. The immune cells can be obtained from a subject of interest, such as a subject suspected of having a particular disease or condition, a subject suspected of having a predisposition to a particular disease or condition, a subject who is undergoing therapy for a particular disease or condition, a subject who is a healthy volunteer or healthy donor, or from blood bank. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood. In some aspects, immune cells isolated from cord blood have enhanced immunomodulation capacity, such as measured by CD4- or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood.

When the population of immune cells is obtained from a donor distinct from the subject, the donor is preferably allogeneic, provided the cells obtained are subject-compatible in that they can be introduced into the subject. Allogeneic donor cells may or may not be human-leukocyte-antigen (HLA)-compatible. To be rendered subject-compatible, allogeneic cells can be treated to reduce immunogenicity.

A. T Cells

In some embodiments, the immune cells are T cells. Several basic approaches for the derivation, activation and expansion of functional anti-tumor effector cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

In some embodiments, the T cells are derived from the blood, bone marrow, lymph, umbilical cord, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4$^+$ cells, CD8$^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4$^+$ and/or CD8$^+$ T cells) are naive T (T$_N$) cells, effector T cells (T$_{EFF}$), memory T cells and sub-types thereof, such as stem cell memory T (TSC$_M$), central memory T (TC$_M$), effector memory T (T$_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ T cells are further enriched for or depleted of naive, central memory, effector memory, and/or central memory stem cells, such as by positive or negative selection based on surface antigens associated with the respective subpopulation. In some embodiments, enrichment for central memory T (T$_{CM}$) cells is carried out to increase efficacy, such as to improve long-term survival, expansion, and/or engraftment following administration, which in some aspects is particularly robust in such subpopulations. See Terakura et al. (2012); Wang et al. (2012).

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about 2×10$^6$ lymphocytes), e.g., from about 5 to about 21 days, preferably from about 10 to about 14 days. For example, the cells may be cultured from 5 days, 5.5 days, or 5.8 days to 21 days, 21.5 days, or 21.8 days, such as from 10 days, 10.5 days, or 10.8 days to 14 days, 14.5 days, or 14.8 days.

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as a human leukocyte antigen A2 (HLA-A2) binding peptide, in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

The autologous T-cells can be modified to express a T-cell growth factor that promotes the growth and activation of the autologous T-cells. Suitable T-cell growth factors include, for example, interleukin (IL)-2, IL-7, IL-15, and IL-12. Suitable methods of modification are known in the art. See, for instance, Sambrook et al., MOLECULAR CLONING: A LABORATORY MANUAL, $3^{rd}$ ed., Cold Spring Harbor Press, Cold Spring Harbor, N.Y. 2001; and Ausubel et al., CURRENT PROTOCOLS IN MOLECULAR BIOLOGY, Greene Publishing Associates and John Wiley & Sons, N Y, 1994. In particular aspects, modified autologous T-cells express the T-cell growth factor at high levels. T-cell growth factor coding sequences, such as that of IL-12, are readily available in the art, as are promoters, the operable linkage of which to a T-cell growth factor coding sequence promote high-level expression.

B. NK Cells

In some embodiments, the immune cells are natural killer (NK) cells. Natural killer (NK) cells are a subpopulation of lymphocytes that have spontaneous cytotoxicity against a variety of tumor cells, virus-infected cells, and some normal cells in the bone marrow and thymus. NK cells are critical effectors of the early innate immune response toward transformed and virus-infected cells. NK cells constitute about 10% of the lymphocytes in human peripheral blood. When lymphocytes are cultured in the presence of interleukin 2 (IL-2), strong cytotoxic reactivity develops. NK cells are effector cells known as large granular lymphocytes because of their larger size and the presence of characteristic azurophilic granules in their cytoplasm (Herberman, 1986). NK cells differentiate and mature in the bone marrow, lymph nodes, spleen, tonsils, and thymus. NK cells can be detected by specific surface markers, such as CD16, CD56, and CD8 in humans. NK cells do not express T-cell antigen receptors, the pan T marker CD3, or surface immunoglobulin B cell receptors.

Stimulation of NK cells is achieved through a cross-talk of signals derived from cell surface activating and inhibitory receptors. The activation status of NK cells is regulated by a balance of intracellular signals received from an array of germ-line-encoded activating and inhibitory receptors (Campbell, 2006). When NK cells encounter an abnormal cell (e.g., tumor or virus-infected cell) and activating signals predominate, the NK cells can rapidly induce apoptosis of the target cell through directed secretion of cytolytic granules containing perforin and granzymes or engagement of death domain-containing receptors. Activated NK cells can also secrete type I cytokines, such as interferon-γ, tumor necrosis factor-α and granulocyte-macrophage colony-stimulating factor (GM-CSF), which activate both innate and adaptive immune cells as well as other cytokines and. Production of these soluble factors by NK cells in early innate immune responses significantly influences the recruitment and function of other hematopoietic cells. Also, through physical contacts and production of cytokines, NK cells are central players in a regulatory crosstalk network with dendritic cells and neutrophils to promote or restrain immune responses.

In certain embodiments, NK cells are derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art. Particularly, umbilical CB is used to derive NK cells. In certain aspects, the NK cells are isolated and expanded by the previously described method of ex vivo expansion of NK cells (Spanholtz et al., 2011; Shah et al., 2013). In this method, CB mononuclear cells are isolated by ficoll density gradient centrifugation and cultured in a bioreactor with IL-2 and artificial antigen presenting cells (aAPCs). After 7 days, the cell culture is depleted of any cells expressing CD3 and re-cultured for an additional 7 days. The cells are again CD3-depleted and characterized to determine the percentage of CD56$^+$/CD3$^-$ cells or NK cells. In other methods, umbilical CB is used to derive NK cells by the isolation of CD34$^+$ cells and differentiation into CD56$^+$/CD3$^-$ cells by culturing in medium contain SCF, IL-7, IL-15, and IL-2.

C. Engineering of Host Cells

The immune cells (e.g., autologous or allogeneic T cells (e.g., regulatory T cells, CD4+ T cells, CD8+ T cells, or gamma-delta T cells), NK cells, invariant NK cells, or NKT cells can be genetically engineered to express antigen receptors such as engineered TCRs and/or chimeric antigen receptors (CARs). For example, the host cells (e.g, autologous or allogeneic T-cells) are modified to express a T cell receptor (TCR) having antigenic specificity for a cancer antigen. In particular embodiments, NK cells are engineered to express a TCR. The NK cells may be further engineered to express a CAR. Multiple CARs and/or TCRs, such as to different antigens, may be added to a single cell type, such as T cells or NK cells.

Suitable methods of modification are known in the art. See, for instance, Sambrook and Ausubel, supra. For example, the cells may be transduced to express a T cell receptor (TCR) having antigenic specificity for a cancer antigen using transduction techniques described in Heemskerk et al. (2008) and Johnson et al. (2009).

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

V. Methods of Use

A. Treatments

In some embodiments, the present disclosure provides methods for immunotherapy comprising administering an effective amount of the immune cells of the present disclosure. In one embodiments, a medical disease or disorder is treated by transfer of an immune cell population that elicits an immune response. In certain embodiments of the present disclosure, cancer or infection is treated by transfer of an immune cell population that elicits an immune response. Provided herein are methods for treating or delaying progression of cancer in an individual comprising administering to the individual an effective amount an antigen-specific cell therapy. The present methods may be applied for the treatment of immune disorders, solid cancers, hematologic cancers, and viral infections.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma;

teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; hodgkin's; paragranuloma; malignant lymphoma, small lymphocytic; malignant lymphoma, large cell, diffuse; malignant lymphoma, follicular; mycosis fungoides; other specified non-Hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); chronic myeloblastic leukemia (CML); and blastic plasmacytoid dendritic cell neoplasm (BPDCN).

Particular embodiments concern methods of treatment of leukemia. Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically split into its acute and chronic forms.

In certain embodiments of the present disclosure, immune cells are delivered to an individual in need thereof, such as an individual that has cancer. The cells then enhance the individual's immune system to attack the respective cancer cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

In some embodiments, the subject can be administered nonmyeloablative lymphodepleting chemotherapy prior to the immune cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously.

Likewise, any suitable dose of cyclophosphamide and flu-darabine can be administered. In particular aspects, around 60 mg/kg of cyclophosphamide is administered for two days after which around 25 mg/m$^2$ fludarabine is administered for five days.

In certain embodiments, a growth factor that promotes the growth and activation of the immune cells is administered to the subject either concomitantly with the immune cells or subsequently to the immune cells. The immune cell growth factor can be any suitable growth factor that promotes the growth and activation of the immune cells. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of immune cells can be administered by a number of routes, including parenteral administration, for example, intravenous, intraperitoneal, intramuscular, intrasternal, or intraarticular injection, or infusion.

The immune cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circum-stances. The therapeutically effective number of immune cells will be dependent on the subject being treated, the severity and type of the affliction, and the manner of administration. In some embodiments, doses that could be used in the treatment of human subjects range from at least 3.8×10$^4$, at least 3.8×10$^5$, at least 3.8×10$^6$, at least 3.8×10$^7$, at least 3.8×10$^8$, at least 3.8×10$^9$, or at least 3.8×10$^{10}$ immune cells/m$^2$. In a certain embodiment, the dose used in the treatment of human subjects ranges from about 3.8×10$^9$ to about 3.8×10$^{10}$ immune cells/m$^2$. In additional embodi-ments, a therapeutically effective number of immune cells can vary from about 5×10$^6$ cells per kg body weight to about 7.5×10$^8$ cells per kg body weight, such as about 2×10$^7$ cells to about 5×10$^8$ cells per kg body weight, or about 5×10$^7$ cells to about 2×10$^8$ cells per kg body weight. The exact number of immune cells is readily determined by one of skill in the art based on the age, weight, sex, and physiological condi-tion of the subject. Effective doses can be extrapolated from dose-response curves derived from in vitro or animal model test systems.

B. Pharmaceutical Compositions

Also provided herein are pharmaceutical compositions and formulations comprising immune cells (e.g., T cells or NK cells) and a pharmaceutically acceptable carrier.

Pharmaceutical compositions and formulations as described herein can be prepared by mixing the active ingredients (such as an antibody or a polypeptide) having the desired degree of purity with one or more optional pharma-ceutically acceptable carriers (Remington's Pharmaceutical Sciences 22$^{nd}$ edition, 2012), in the form of lyophilized formulations or aqueous solutions. Pharmaceutically accept-able carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 resi-dues) polypeptides; proteins, such as serum albumin, gela-tin, or immunoglobulins; hydrophilic polymers such as polyvinylpyrrolidone; amino acids such as glycine, gluta-mine, asparagine, histidine, arginine, or lysine; monosac-charides, disaccharides, and other carbohydrates including glucose, mannose, or dextrins; chelating agents such as EDTA; sugars such as sucrose, mannitol, trehalose or sor-bitol; salt-forming counter-ions such as sodium; metal com-plexes (e.g. Zn— protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycopro-teins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional gly-cosaminoglycanases such as chondroitinases.

C. Combination Therapies

In certain embodiments, the compositions and methods of the present embodiments involve an immune cell population in combination with at least one additional therapy. The additional therapy may be radiation therapy, surgery (e.g., lumpectomy and a mastectomy), chemotherapy, gene therapy, DNA therapy, viral therapy, RNA therapy, immu-notherapy, bone marrow transplantation, nanotherapy, monoclonal antibody therapy, or a combination of the fore-going. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side—effect limiting agents (e.g., agents intended to lessen the occurrence and/or sever-ity of side effects of treatment, such as anti-nausea agents, etc.). In some embodiments, the additional therapy is radia-tion therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreven-tative agent. The additional therapy may be one or more of the chemotherapeutic agents known in the art.

An immune cell therapy may be administered before, during, after, or in various combinations relative to an additional cancer therapy, such as immune checkpoint therapy. The administrations may be in intervals ranging from concurrently to minutes to days to weeks. In some embodiments where the immune cell therapy is provided to a patient separately from an additional therapeutic agent, one would generally ensure that a significant period of time did not expire between the time of each delivery, such that the two compounds would still be able to exert an advanta-geously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an immune cell therapy is "A" and an anti-cancer therapy is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/B/A | A/B/B/A | B/B/A/A |
| B/A/B/A | B/A/A/B | A/A/A/B | B/A/A/A | A/B/A/A | A/A/B/A |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example.

The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer,* 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Gen-bank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respec-tively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a human-ized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as treme-limumab; formerly ticilimumab), U.S. Pat. No. 6,207,156; Hurwitz et al. (1998) *Proc Natl* Acad Sci USA 95(17): 10067-10071; Camacho et al. (2004) J Clin Oncology 22(145): Abstract No. 2505 (antibody CP-675206); and Mokyr et al. (1998) *Cancer Res* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017, 114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody com-prises the heavy and light chain CDRs or VRs of ipilim-umab. Accordingly, in one embodiment, the antibody com-prises the CDR1, CDR2, and CDR3 domains of the VH region of ipilimumab, and the CDR1, CDR2 and CDR3 domains of the VL region of ipilimumab. In another embodi-ment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilim-umab).

Other molecules for modulating CTLA-4 include CTLA-4 ligands and receptors such as described in U.S. Pat. Nos. 5,844,905, 5,885,796 and International Patent Appli-cation Nos. WO1995001994 and WO1998042752; all incor-porated herein by reference, and immunoadhesins such as described in U.S. Pat. No. 8,329,867, incorporated herein by reference.

4. Surgery

Approximately 60% of persons with cancer will undergo surgery of some type, which includes preventative, diagnos-tic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radio-therapy, hormonal therapy, gene therapy, immunotherapy, and/or alternative therapies. Tumor resection refers to physi-cal removal of at least part of a tumor. In addition to tumor resection, treatment by surgery includes laser surgery, cryo-surgery, electrosurgery, and microscopically-controlled sur-gery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodi-ments to improve the therapeutic efficacy of treatment. These additional agents include agents that affect the upregulation of cell surface receptors and GAP junctions, cytostatic and differentiation agents, inhibitors of cell adhe-sion, agents that increase the sensitivity of the hyperprolif-erative cells to apoptotic inducers, or other biological agents. Increases in intercellular signaling by elevating the number of GAP junctions would increase the anti-hyperproliferative effects on the neighboring hyperproliferative cell popula-tion. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodi-ments. Examples of cell adhesion inhibitors are focal adhe-sion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

VI. Articles of Manufacture or Kits

An article of manufacture or a kit is provided comprising immune cells is also provided herein. The article of manu-facture or kit can further comprise a package insert com-prising instructions for using the immune cells to treat or delay progression of cancer in an individual or to enhance immune function of an individual having cancer. Any of the antigen-specific immune cells described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastel-loy). In some embodiments, the container holds the formu-lation and the label on, or associated with, the container may indicate directions for use. The article of manufacture or kit may further include other materials desirable from a com-mercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent).

Suitable containers for the one or more agent include, for example, bottles, vials, bags and syringes.

VII. Examples

The following Examples section provides further details regarding examples of various embodiments. It should be appreciated by those of skill in the art that the techniques disclosed in the examples that follow represent techniques and/or compositions discovered by the inventors to function well. However, those of skill in the art should, in light of the present disclosure, appreciate that many changes can be made in the specific embodiments which are disclosed and still obtain a like or similar result without departing from the spirit and scope of the disclosure. These examples are illustrations of the methods and systems described herein and are not intended to limit the scope of the disclosure. Non-limiting examples of such include, but are not limited to those presented below.

Example 1—Methods

Cells and cell lines. K562, THP-1, MV4-11, MOLM13, OPM2, KMS26, RS4-11, KOPN8 and RCH-ACV cell lines were maintained in RPMI 1640 supplemented with 10% heat-inactivated FBS (Sigma Aldrich)+1% penicillin and streptomycin. Primary human T-cells from healthy donors (CD3$^+$, frozen) were purchased from All Cells. T-cells were maintained in Immunocult—XF T cell expansion media (Stemcell) supplemented with 300 u/ml of recombinant human-IL2. NKL cell line was maintained in RPMI-1640 medium supplemented with 10% heat-inactivated FBS (Sigma Aldrich)+1% penicillin and of streptomycin and 150 unit/ml human IL2 (Peprotech).

Lentivirus production. The indicated lentivirus construct was mixed with psPAX2 and pMD2.G (Addgene) at a ratio of 4:3:1 and transfected into 293T cells using Polyjet transfection reagent (Signagen). Virus-containing supernatant was collected 48-72 hrs post-transfection and concentrated over 20% sucrose cushion by ultracentrifugation at 25 k RPM for 90 min. The concentrated virus was resuspended in 500 µl of T cell medium (Immunocult with 100-300 U/ml human IL-2) with rotation for 2-4 hr.

CAR-T cell transduction. At day 0, 1×10$^6$ T cells were thawed in 1.5 ml T cell medium, upright in a 25-ml flask, stimulated with anti-CD3/CD28 magnetic beads or Tetrameric antibody according to manufacturer's instruction. On day 1, 500 µl of concentrated lentivirus was added to T cells in upright flask. At days 2-3, cell culture was monitored until the medium color changes to orange. Medium was added to a total volume of 4 ml, after which the flask was laid flat. At day 4, the virus containing medium and beads were removed and the cells were resuspended at ~1×10$^6$ cells/ml in fresh T cell medium. For pSIN-Puro CAR-T construct, at days 5-8, Puromycin was added at 0.5 µg/ml for 48 hr. Dead cells were removed by separation over Ficoll (centrifugation at 1 g, with no brake). This was followed by 1 µg/ml Puromycin selection for 24 hrs, followed by dead cell removal. The percentage of CART-LILRB4 was determined by flow cytometry-based LILRB4 binding assay. At days 9-21, T cells were activated with anti-CD3/CD28 beads for 3 days, followed by replacing with fresh medium to expand the culture. For pLVX-GFP CAR-T construct, at days 5-7, ~5×10$^6$ GFP$^+$ cells were sorted for further expansion. If fewer GFP$^+$ cells were sorted, an expansion in upright flask would be conducted. Then, T cells were activated with anti-CD3/CD28 beads for 3 days, followed by replacing with fresh medium to expand the culture until day 21. Alternate method of transduction: On day 0, 2×10$^6$ T-cells were thawed and activated with anti-CD3/CD28 magnetic beads for 24-48 hours. Retronectin (Takara) coated plates were prepared per manufacturers's instruction. Concentrated lentivirus was bound to Retronectin (Retronectin bound virus [RBV]) by plate centrifuguation per manufacturer's direction. Following this, activated T-cells were added to RBV plates and cultured for total 7-10 days in T-cell media with 100 U/ml recombinant human IL2, maintaining cell density ~1×10$^6$ cells/ml. Magnetic beads were removed and media changed on day 5 of culture. The percentage of CART-LILRB4 was determined by flow cytometry-based LILRB4 binding assay. Cells were then viably frozen for downstream use.

NK cell transduction. NKL were resuspended in viral supernatants of pLVX-GFP CAR-T construct (1×10$^6$ cells/ml) with 8 µg/ml polybrene, centrifuged at 1800 rpm for 120 min and incubated for another 4 hrs. Then viral supernatants were replaced by RPMI-1640 medium supplemented with 10% heat-inactivated FBS (Sigma Aldrich)+1% penicillin and of streptomycin and 150 unit/ml human IL-2 (Peprotech). GFP$^+$ cells were sorted as CAR NKL cells. For primary CAR-NK cells, CAR construct were cloned into retrovirus backbone XZ201 and transfected into phenix-ampho 297T cells. The retrovirus supernatant were collected 48 hrs and 72 hrs after transfect and bounded to retronectin coated plate. Primary NK cells were isolated from Umbilical Cord Blood (UCB) by depleing CD3$^+$ cell and CD14$^+$ cells using autoMACS. Then the NK cells were cocultured with K562-4-1BBL feeder cells (K562 cells transfected with the cDNA of TNFSF9 gene by lentivirus) in RPMI-1640 medium supplemented with 10% heat-inactivated FBS (Sigma Aldrich)+1% penicillin and of streptomycin and 150 U/ml human IL-2 (Peprotech). 5 days later, the expanded NK cells were added to Retronectin Bound Virus [RBV] plates and cultured for another 5 to 9 days. During the culture of NK cells, the culture medium with IL2 were changed every two days.

T cell flow-based killing assay. T-cells (CAR-T or Control) were co-cultured with DDAO-SE-labeled target AML cells for 4-6 hours in RPMI in 96 well U-bottom plates at the indicated E:T ratios. Following this, each sample was mixed with PI (1:1000 total volume) and flow cytometry counting beads were added (~10K/sample). Cytotoxicity was calculated as: Living MV4-11 Cells: DDAOSE (+), PI (−); MV411=MV4-11 Cell count/# of beads (Co-culture WITHOUT T-cells); X=Living Target Cell cell count/# of Beads (Co-culture WITH T-cells); % Cytotoxicity=(MV411-X)/MV411*100.

NK cell flow-based killing assay. Flow-based killing assays were performed by co-culcuturing untransformed NKL cells or CAR NK cells with carboxyfluorescein diacetate succinimidyl ester (CFSE)-labeled leukemia cells in U— bottom 96-well plates for 4-6 hrs. Following this, each sample was mixed with PI and analyzed by FACS Caliburl (BD bioscience). Cell lysis was calculated as the percentage of PI positive leukemia cells among total leukemia cells. Spontaneous cell death (no effector cells) was subtracted from total killing (in the presence of effector cells).

Cytokine production. 5×10$^4$ untransformed NKL cells or CAR NK cells were co-cultured with 5×10$^4$ target cells in U-bottom 96-well plates for 10 h. Release of IFN-γ was detected in the culture supernatants by ELISA kit (biolegend) following the manual provided by the vender.

Human AML xenograft. For CAR-T experiments, 6-8 week-old NSG mice were sub-lethally irradiated (200cGy).

One day after, each mouse was given with $5\times10^5$ human leukemia cells resuspended in 200 µl PBS via tail-vein injection. Four days later, $2\times10^6$ CAR-T cells resuspended in 200 µl PBS were injected into each mouse via tail-vein injection. Weight, peripheral blood, and BLI were monitored and analyzed weekly. For survival curve experiments, the death of mice was recorded when the moribund animals were euthanized.

For CAR-NK experiments, 6-8 week-old NSG mice were sub-lethally irradiated with 200cGy X-ray. One day later (defined as day 0), each mouse was given $3\times10^5$ MV4-11-luci resuspended in 200 µl PBS via tail-vein injection. To study the functions of CAR-NK cell in blocking leukemia engraftment, $5\times10^6$ untransformed NKL or CAR-NKL cells were transplanted into each mouse via tail-vein injection on day 0, followed by 4 additional injections of $5\times10^6$ untransformed NKL or CAR-NKL cells every 3 days. To study the functions of CAR-NK cell in decreasing leukemia burden, $5\times10^6$ untransformed NKL or CAR-NKL cells were transplanted into each mouse via tail-vein injection on day 7, followed by 3 additional injections of $5\times10^6$ untransformed NKL or CAR-NKL cells every 3 days. Human IL2 (10000 IU) was administration to each mouse via I.P. injection together when NKL cells were injected each time. Weight, peripheral blood, and BLI were monitored weekly.

CFU Assay. Human cord blood ($1\times10^3$) CD34$^+$ cells were co-cultured with $1\times10^4$ indicated types of T cells or NKL cells for 4 hrs then resuspended in MethoCult Optimum (STEMCELL Technologies) for 10 days followed by CFUs counting. The colonies were then solubilized in RPMI overnight and a portion of cells were used for flow cytometry analysis.

Example 2—Results

Figure 1B:
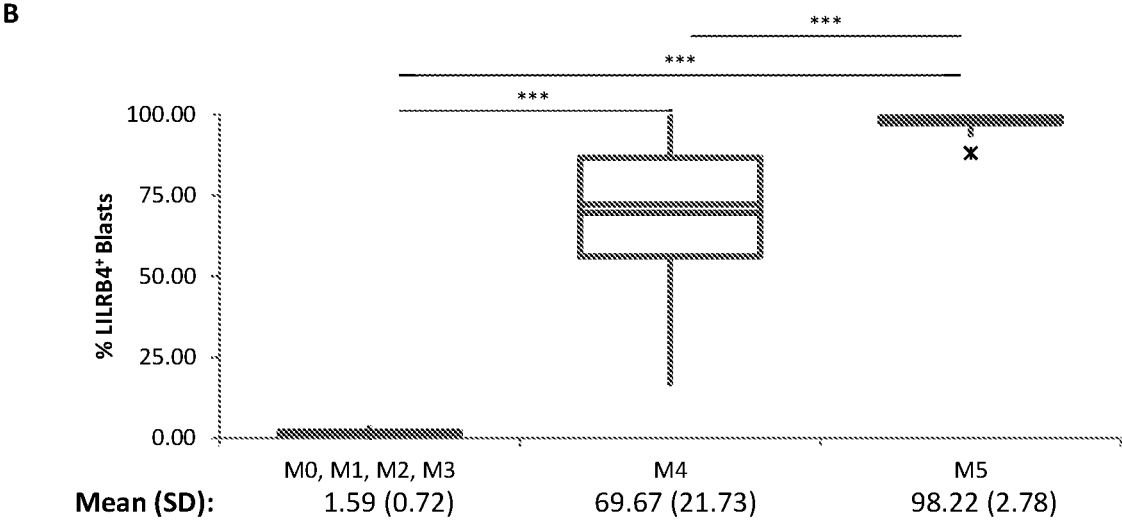
Figure 1C:
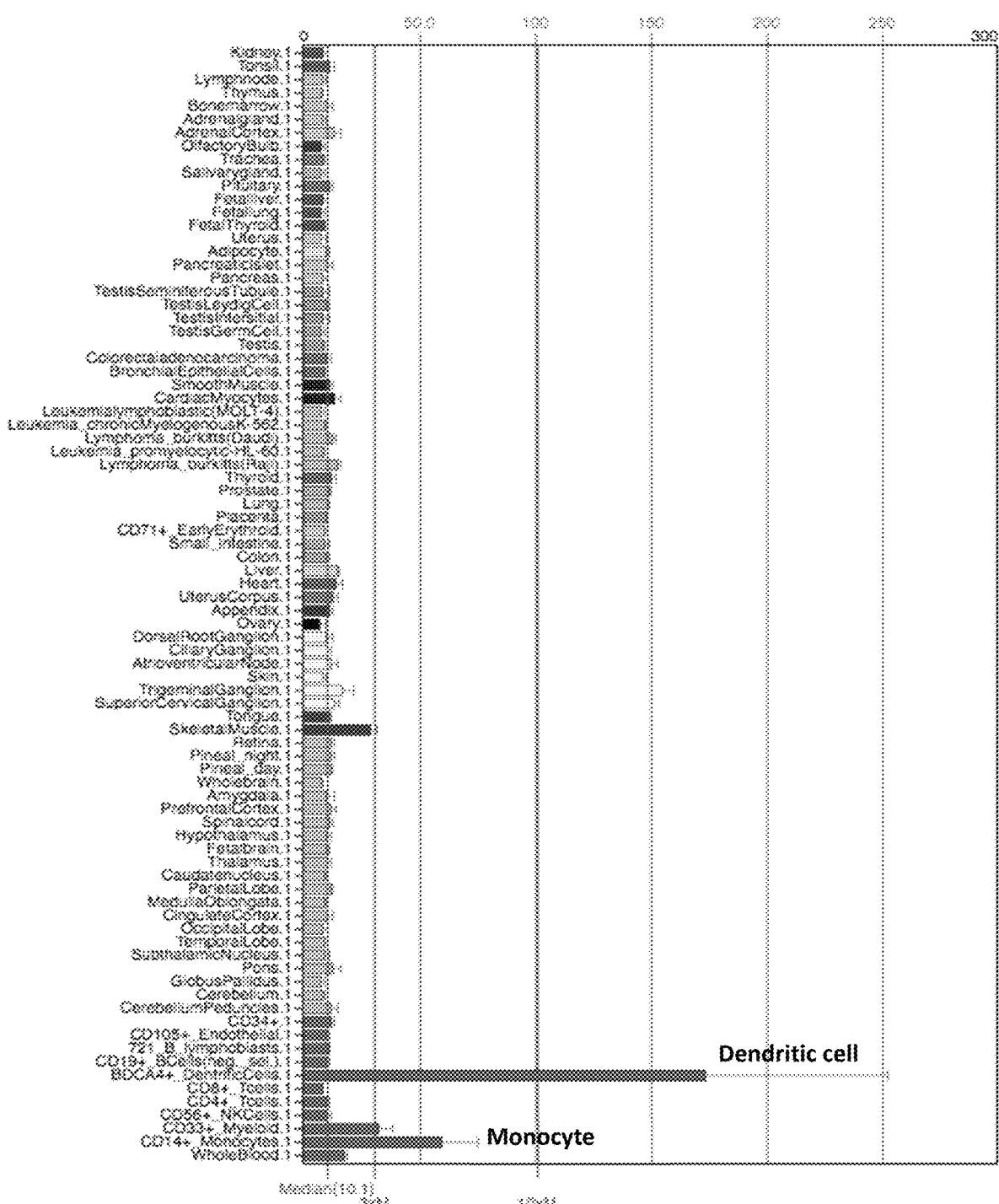
Figure 1D:
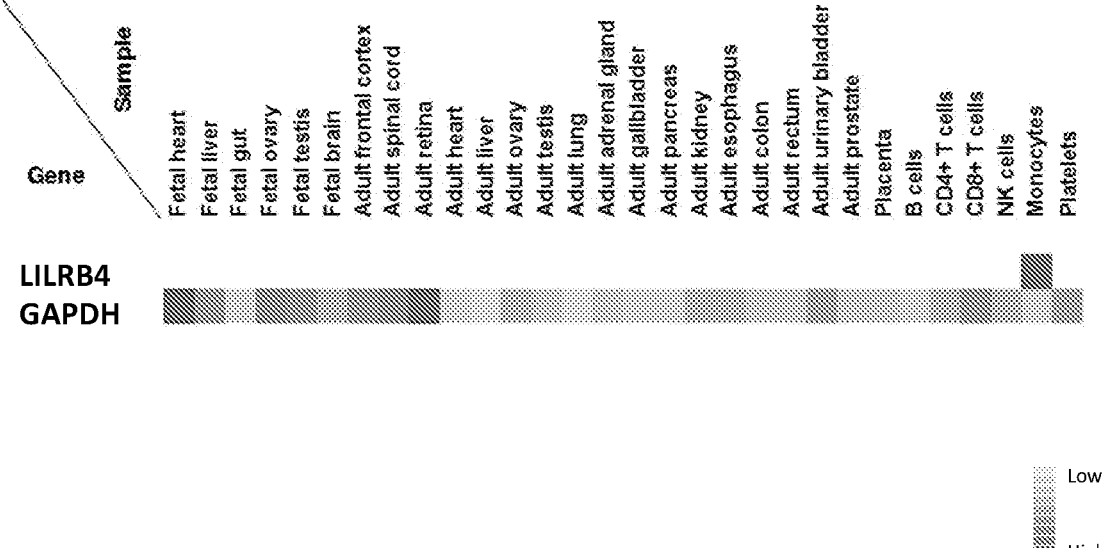
Figure 1E:
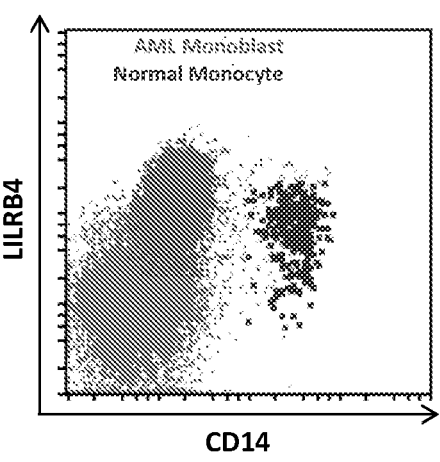
Figure 1F:
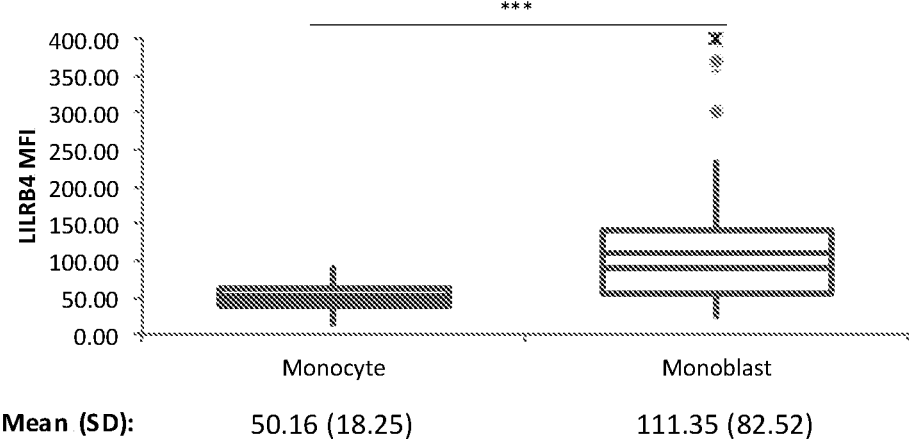
Figure 1G:
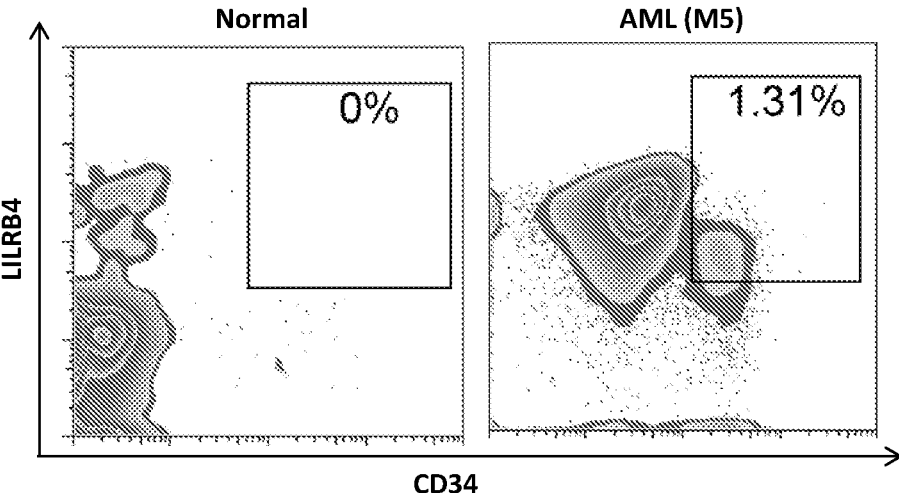

Recently, the inventors and others have shown that several LILRBs and a related ITIM-containing receptor, LAIR1, have tumor-promoting functions in various hematopoietic and solid cancer cells (Zheng et al., 2012; Kang et al., 2015; Kang et al., 2016; Chen et al., 2015). They systematically analysed the surface expression of LILRBs on 105 AML patient samples from the University of Texas Southwestern Medical Center (UTSW). LILRB4 was only detected on monocytic AML cells (FAB M4, M5) but not on other AML subtypes (FIG. 1A-B). Of note, LILRB4 on human monocytic AML cells is more sensitive and specific than that of the mature monocytic AML cell marker, CD14 (FIG. 1A). Importantly, LILRB4 levels were higher on monocytic AML cells compared to those on normal monocytes (FIG. 1E-F). Concordantly, the inventors observed the expression pattern of LILRB4 can be expressed on CD34$^+$ AML progenitors that may enrich for AML stem cell activity (FIG. 1G, right panel). Importantly, in normal human samples, LILRB4 is only expressed on normal monocytic cells and immune-suppressive tolerogenic dendritic cells but does not show expression on other cells including hematopoietic stem cells (HSC) (FIG. 1C for mRNA levels, FIG. 1D for surface protein levels, FIG. 1G, left panel). In cancer patients, LILRB4 is also expressed on tumor protective immune cells, such as tolerogenic dendritic cells, myeloid derived suppressor cells, and tumor associated macrophages (Kang et al., 2016). These results demonstrate that LILRB4, as a marker of monocytic AML, may represent an ideal target for treating this subtype of AML.

Figure 3A:
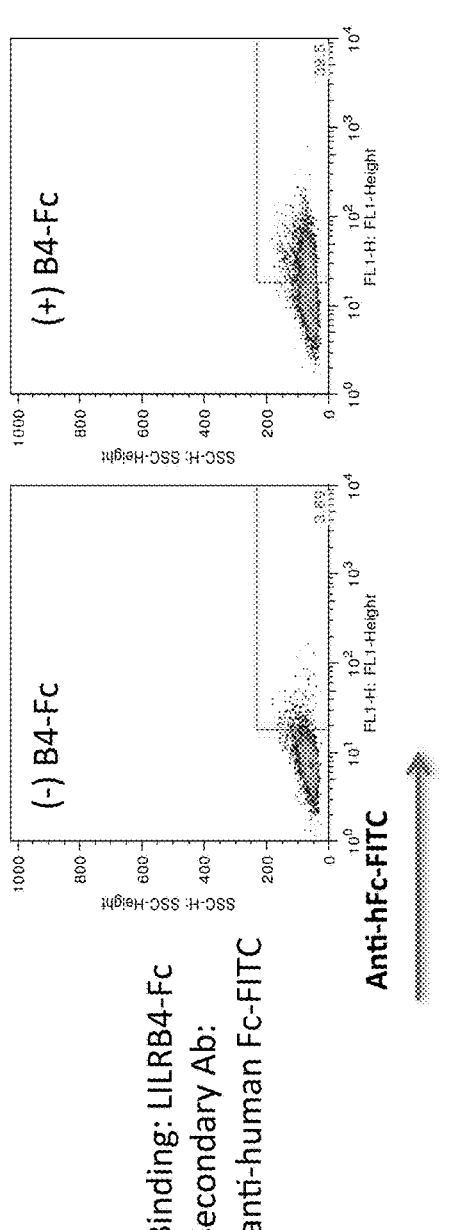
FIGS. 3A-B. Efficient generation of LILRB4 CAR-T cells. Human primary T-cells were transduced with lentivirus encoding LILRB4 CAR (scFv Hu128).
Figure 3B:
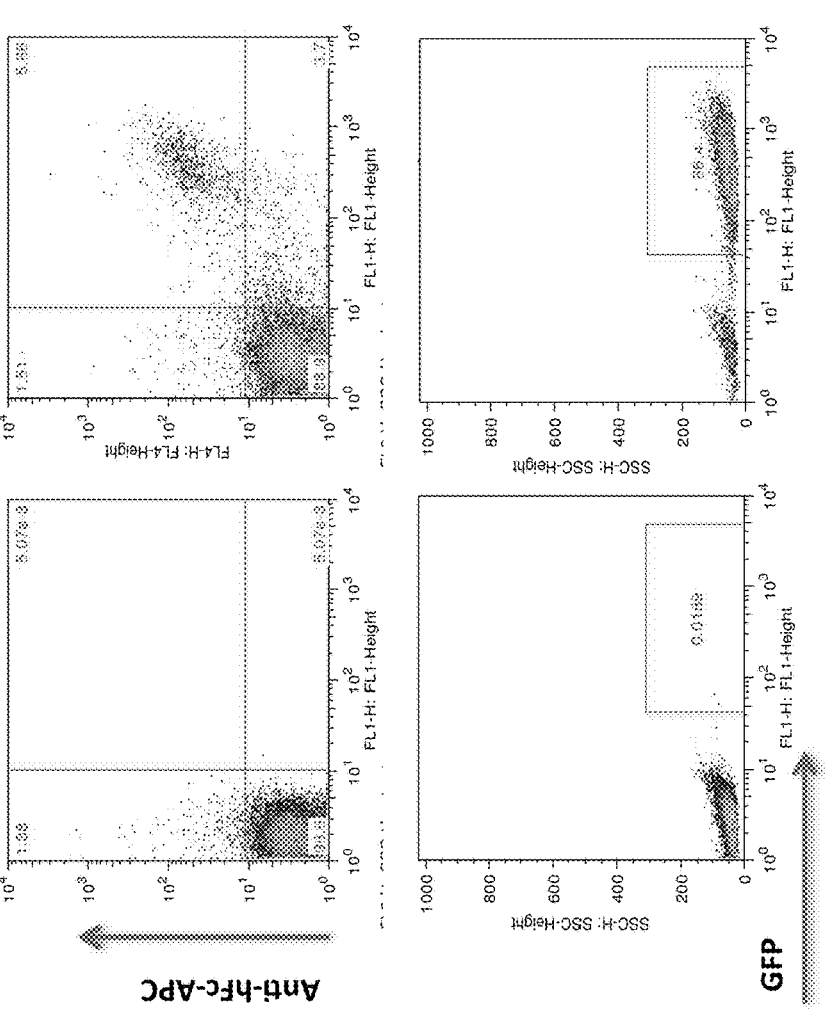

The inventors developed several humanized anti-LILRB4 antibodies that have been demonstrated to decrease disease burden and prolong survival in various xenograft mouse models of AML. Based on this, the inventors generated several variations of a novel LILRB4 CAR-T cell (FIG. 2). The antigen recognition domain—single chain variable fragment (scFv) was derived from anti-LILRB4 antibodies: #128-3 (humanized ab) and #8 (humanized ab). This was cloned the CD8α hinge and transmembrane domain, followed by either a CD28 or 4-1BB co-stimulatory domain, both terminating with the CD3-ζ activation domain. Some CAR constructs were codon-optimized for expression in human cells (Genescript). Primary human T cells were able to be efficiently transduced by lentivirus encoding LILRB4 CAR (FIGS. 3A-B). These LILRB4 CAR-T cells also show specific binding to target protein LILRB4 (FIGS. 3A-B). Importantly, these results demonstrate these cells efficiently lysed LILRB4$^+$ target AML cells in co-culture experiment (FIGS. 4A-C) and decreased leukemia burden in AML xenograft experiments (FIGS. 5A-D). In contrast, control-T cells did not have specific cytotoxic activity (FIGS. 4A-C, FIGS. 5A-D). Significantly, LILRB4 CAR-T cells do not show toxicity against normal human cord blood CD34$^+$ HSCs in a CFU assay (FIG. 6).

Figure 7A:
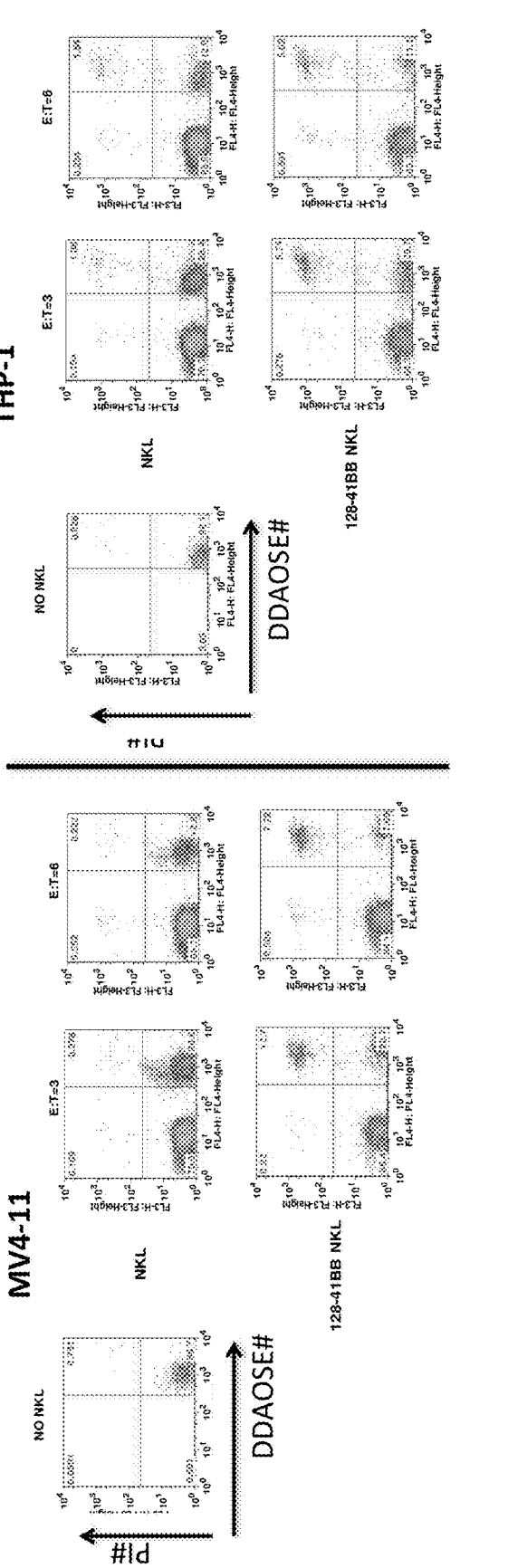

Natural killer (NK) cells represent an important part of innate immunity. Unlike T cells, NK cells can initiate anti-tumor cytotoxicity without prior sensitization and may potentially have fewer complications due to cytokine release syndrome, and on-target/off-tumor effects (Hermanson and Kaufman, 2015). Because of shared signaling activation mechanisms in T-cells and NK-cells, the CAR construct containing CD3-ζ activation domain can also activate NK cells (Schonfeld et al., 2015). The inventors showed that the introduction of the LILRB4 CAR into the human NKL cell line to generate LILRB4 CAR-NKL cells, can specifically target monocytic AML cells both in vitro (FIGS. 7A-D, FIGS. 8A-B) and in vivo (FIGS. 9A-10D, FIGS. 10A-D). The inventors also showed that the introduction of the LILRB4 CAR into the human UCB NK cells to generate LILRB4 CAR-UCBNK cells, can specifically target monocytic AML cells (FIG. 7E). These LILRB4 CAR-NK cells may provide an alternative universal "off-the shelf" CAR product with safe and controllable properties.

LILRB4 CAR-T and CAR-NKL cells may effectively target monocytic AML, and may be useful in some cases LILRB4$^+$ CLL, multiple myeloma, Hodgkin's Lymphoma, and blastic plasmacytoid dendritic cell neoplasm (BPDCN), while having minimal toxicity against normal cells. LILRB4 CAR may also eliminate myeloid derived suppressor cells (MDSCs), tumor associated macrophages (TAMs), and tolerogenic dendritic cells in solid cancer. Moreover, as monocytic lineage APCs are a major source of IL-6 in CRS seen during CAR-T cell therapy (Barrett et al., 2016), LILRB4 CAR may potentially reduce the risk of this life-threatening adverse effect by targeting IL-6 producing monocytic APCs while eliminating monocytic AML.

TABLE 1

Heavy and Light Variable Domains

| | Heavy Chain Sequence (VH) | | | Light Chain Sequence (VL) | | |
|---|---|---|---|---|---|---|
| | CDR1 | CDR2 | CDR3 | CDR1 | CDR2 | CDR3 |
| | | Amino acid sequence<br>Nucleic acid sequence | | | Amino acid sequence<br>Nucleic acid sequence | |
| 128 | GIDFSNHYY<br>(SEQ ID NO: 1)<br>EVQLLESGGGLVQPGGSLRLSCAASGIDFSNHYYIYWVRQA<br>PGKGLEWIGCIFSGDSASTYYASWAKGRFTISRDNSKNTLYL<br>QMNSLRAEDTAVYYCARGMSTNDWASDLWGQGTLVTVSS<br>(SEQ ID NO: 7)<br>GAGGTGCAGCTGCTGGAGAGCGGAGGAGGCCTGGTGCA<br>GCCTGGAGGATCCCTGAGGCTGTCCTGTGCCGCCTCCGGC<br>ATCGACTTCTCCAACCACTACTACATCTACTGGGTGAGGCA<br>GGCTCCCGGCAAGGGACTGGAGTGGATCGGCTGTATCTTC<br>TCCGGCGACTCCGCCTCCACCTACTACGCCTCCTGGGCCAA<br>GGGCAGGTTTACCATCTCCCGGGACAACTCCAAGAACACC<br>CTGTACCTGCAGATGAACTCCCTGAGGGCCGAGGACACCG<br>CTGTGTACTACTGCGCCAGGGGCATGTCCACCAACGACTG<br>GGCTTCCGATCTGTGGGGCCAGGGCACACTGGTGACCGT<br>GTCCAGC (SEQ ID NO: 8) | IFSGDSAST<br>(SEQ ID NO: 2) | ARGMSTNDWASD<br>L (SEQ ID NO: 3) | ESINSIY (SEQ ID<br>NO: 4)<br>DIQMTQSPSSLSASVGDRVTITCQASESINSIYLAWYQQK<br>PGKAPKLLIYRASTLASGVPSRFSGSGSGTDFTLTISSLQPE<br>DFATYYCQQSYDWGDVENTFGGGTKVEIK (SEQ ID NO:<br>9)<br>GACATCCAGATGACCCAGTCCCCTTCCTCCCTGTCCGCT<br>TCCGTGGGCGATAGGGTGACCATCACCTGCCAGGCCTC<br>CGAGTCCATCAACAGCATCTACCTGGCCTGGTACCAGC<br>AGAAGCCCGGCAAGGCCCCCAAGCTGCTGATCTATCGG<br>GCTTCCACACTGGCCTCCGGAGTGCCTTCCAGGTTTTC<br>CGGCTCCGGCTCCGGCACCGACTTCACCCTGACCATCT<br>CCAGCCTGCAGCCCGAGGACTTCGCCACCTACTACTGC<br>CAGCAGTCCTACGACTGGGGCGACGTGGAGAACACCT<br>TTGGCGGCGGCACCAAGGTGGAGATCAAG (SEQ ID<br>NO: 10) | RAS (SEQ ID<br>NO: 5) | QQSYDWGDVE<br>NT (SEQ ID NO: 6) |
| 8 | GFSLISYD (SEQ<br>ID NO: 11)<br>EVQLLESGGGLVQPGGSLRLSCAASGFSLISYDMYWVRQAP<br>GKGLEYIGIIYSDGYTFYATGAKGRFTISRDNSKNTLYLQMNSL<br>RAEDTAVYYCATNAFALWGRGTLVTVSS (SEQ ID NO: 17)<br>GAGGTGCAGCTGCTGGAATCCGGAGGAGGACTGGTGCA<br>GCCTGGCGGATCCCTGAGGCTGTCCTGCGCTGCTTCCGGC<br>TTCTCCCTGATCAGCTACGACATGTACTGGGTGAGGCAGG<br>CTCCTGGCAAGGGCCTGGAGTACATCGGCATCATCTACTCC<br>GACGGCTACACCTTCTACGCCACCGGCGCCAAGGGCAGG<br>TTCACCATCTCCAGGGACAACTCCAAGAACACCCTGTACCT<br>GCAGATGAACTCCCTGAGGGCCGAGGACACCGCCGTGTA<br>CTACTGCGCCACCAACGCCTTCGCTCTGTGGGGCAGGGGC<br>ACACTGGTGACCGTCTCCTCC (SEQ ID NO: 18) | IYSDGYT (SEQ<br>ID NO: 12) | ATNAFAL (SEQ ID<br>NO: 13) | QNVYNNNW<br>(SEQ ID NO: 14)<br>AIQLTQSPSSLSASVGDRVTITCQSSQNVYNNNWLVWLQ<br>QKPGKAPKRLIYTASSLASGVPSRFSGSGSGTDFTLTISSLQ<br>PEDFATYYCAGGYSGPIYTEGGGTKVEIK (SEQ ID NO: 19)<br>GCCATCCAGCTGACCCAGTCCCCTTCCTCCCTGTCCGCT<br>TCCGTGGGCGACAGGGTGACCATCACCTGCCAGTCCTC<br>CCAGAACGTGTACAACAACAACTGGCTGGTCTGGCTGC<br>AGCAGAAGCCCGGCAAGGCCCCTAAGAGGCTGATCTA<br>CACCGCTTCCTCCCTGGCTTCCGGAGTGCCCTCCAGGT<br>TTTCCGGCTCCGGCTCCGGCACCGATTTCACCCTGACC<br>ATCTCCTCCCTGCAGCCCGAGGACTTCGCCACCTACTAC<br>TGCGCCGGCGGCTACTCCGGCCCTATCTACACCTTCGGC<br>GGCGGCACCAAGGTGGAGATCAAG (SEQ ID NO: 20) | TAS (SEQ ID<br>NO: 15) | AGGYSGPIYT<br>(SEQ ID NO: 16) |

TABLE 2

CAR Constructs

| CAR Protein Name | Partial Construct Configuration (N term.–C Term.) |
|---|---|
| CAR-128-CD28 (SEQ ID NO: 21) | CD8a H, CD8a TM, CD28 cyto, CD3zIso1 |
| CAR-128-41BB (SEQ ID NO: 22) | CD8a H, CD8a TM, 41BB cyto, CD3zIso1 |
| CAR-8-CD28 (SEQ ID NO: 23) | CD8a H, CD8a TM, CD28 cyto, CD3zIso1 |
| CAR-8-41BB (SEQ ID NO: 31) | CD8a H, CD8a TM, 41BB cyto, CD3zIso1 |
| CAR-128-CD28-41BB (SEQ ID NO: 32) | CD8a H, CD8a TM, CD28 cyto, 41BB cyto, CD3zIso1 |
| CAR-8-CD28-41BB (SEQ ID NO: 33) | CD8a H, CD8a TM, CD28 cyto, 41BB cyto, CD3zIso1 |
| CAR-128-CD28 (SEQ ID NO: 40) | CD8a H, CD28 TM, CD28 cyto, CD3zIso3 |
| CAR-8-CD28 (SEQ ID NO: 41) | CD8a H, CD28 TM, CD28 cyto, CD3zIso3 |
| CD3zIso1 (SEQ ID: 42) | RVKFSRSADAPAYQQGQNQLYNELNLGRR<br>EEYDVLDKRRGRDPEMGGKPQRRKNPQE<br>GLYNELQKDKMAEAYSEIGMKGERRRGKG<br>HDGLYQGLSTATKDTYDALHMQALPPR |
| CD3zIso3 (SEQ ID: 43) | RVKFSRSADAPAYQQGQNQLYNELNLGRR<br>EEYDVLDKRRGRDPEMGGKPRRKNPQE<br>GLYNELQKDKMAEAYSEIGMKGERRRGKG<br>HDGLYQGLSTATKDTYDALHMQALPPR |

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VIII. References

The following references, to the extent that they provide exemplary procedural or other details supplementary to those set forth herein, are specifically incorporated herein by reference.

Zheng et al., (2012) Inhibitory receptors bind ANGPTLs and support blood stem cells and leukaemia development. Nature, 485, 656-660.

Kang et al., (2015) The ITIM-containing receptor LAIR1 is essential for acute myeloid leukaemia development. Nat Cell Biol, 17, 665-677.

Barrett et al. (2016) Interleukin 6 Is Not Made By Chimeric Antigen Receptor T Cells and Does Not Impact Their Function. Blood, 128, 654.

Kang et al., (2016) Inhibitory leukocyte immunoglobulin-like receptors: Immune checkpoint proteins and tumor sustaining factors. Cell Cycle, 15, 25-40.

Chen et al., (2015) Signalling thresholds and negative B-cell selection in acute lymphoblastic leukaemia. Nature, 521, 357-361.

Hermanson, D. L. and Kaufman, D. S. (2015) Utilizing chimeric antigen receptors to direct natural killer cell activity. Front Immunol, 6, 195.

Schonfeld et al. (2015) Selective inhibition of tumor growth by clonal NK cells expressing an ErbB2/HER2-specific chimeric antigen receptor. Mol Ther, 23, 330-338.

U.S. Patent Publication No. US20050260186

U.S. Patent Publication No. US20060104968

U.S. Patent Publication No. US20140294898

U.S. Patent Publication No. US2014022021

U.S. Patent Publication No. US20110008369

Lieberman, Pharmaceutical Dosage Forms (vols. 1-3, 1992)

Lloyd, The Art, Science and Technology of Pharmaceutical Compounding (1999)

Pickar, Dosage Calculations (1999)

Remington: The Science and Practice of Pharmacy, 20th Edition, 2003, Gennaro, Ed., Lippincott, Williams & Wilkins.

Heemskerk et al., Hum Gene Ther. 19:496-510 (2008).

Johnson et al., Blood 114:535-46 (2009).

Terakura et al. (2012) Blood. 1:72-82.

Wang et al. (2012) J Immunother. 35(9):689-701.

Ford et al. (2001) Gene Therapy 8:1-4.

Prochiantz (2007) Nat. Methods 4:119-20.

Singleton et al., DICTIONARY OF MICROBIOLOGY AND MOLECULAR BIOLOGY, 2nd ed., J. Wiley & Sons (New York, N.Y. 1994).

Sambrook et al., MOLECULAR CLONING, A LABORATORY MANUAL, Cold Springs Harbor Press (Cold Springs Harbor, N Y 1989).

Ausubel et al., CURRENT PROTOCOLS IN MOLECULAR BIOLOGY, Greene Publishing Associates and John Wiley & Sons, N Y, 1994.

Hurwitz et al. (1998) Proc Natl Acad Sci USA 95(17): 10067-10071.

Camacho et al. (2004) J Clin Oncology 22(145): Abstract No. 2505.

Mokyr et al. (1998) Cancer Res 58:5301-5304.

Pardoll, (2012b) Nat Rev Cancer, 12(4): 252-64.

Spanholtz et al., (2011) PLoS One, 6(6): e20740.

Shah et al., (2013) PLoS One, 8:e776781.

Hui and Hashimoto, (1998) Infection Immun., 66(11): 5329-5336.

Christodoulides et al., (1998) Microbiology, 144(Pt 11): 3027-3037.

Bukowski et al., (1998) Clinical Cancer Res., 4(10):2337-2347.

Davidson et al., (1998) J. Immunother 21(5):389-398.

Hellstrand et al., (1998) Acta Oncologica, 37(4):347-353.

Qin et al., (1998) Proc. Natl. Acad. Sci. USA, 95(24): 14411-14416.

Austin-Ward and Villaseca, (1998) Revista Medica de Chile, 126(7):838-845.

Hollander, (201) Front. Immun., 3:3.

Hanibuchi et al., (1998) Int. J. Cancer, 78(4):480-485.

John et al., (2018) Mol. Ther., 26(10):2487-2495.

U.S. Pat. No. 5,824,311

U.S. Pat. No. 5,844,905

U.S. Pat. No. 5,885,796

U.S. Pat. No. 5,801,005

U.S. Pat. No. 5,739,169

U.S. Pat. No. 5,830,880

U.S. Pat. No. 5,846,945

U.S. Pat. No. 6,207,156

U.S. Pat. No. 8,735,553

U.S. Pat. No. 8,354,509

U.S. Pat. No. 8,008,449

U.S. Pat. No. 8,017,114

U.S. Pat. No. 8,119,129

U.S. Pat. No. 8,329,867

WO2009/114335

WO2009/101611

WO2010/027827

WO2011/066342

WO2015016718

WO 01/14424

WO 98/42752

WO 00/37504

WO2001014424

WO2000037504

WO 01/14424

WO1995001994

WO1998042752

What is claimed is:

1. An isolated chimeric antigen receptor (CAR) protein, wherein the CAR protein binds human leukocyte immunoglobulin like receptor 4 (LILRB4) and comprises an extracellular domain comprising a single-chain variable fragment comprising (i) a VH comprising the amino acid sequence of SEQ ID NO: 7 and a VL comprising the amino acid sequence of SEQ ID NO: 9, or (ii) a VH comprising the amino acid sequence of SEQ ID NO: 17 and a VL comprising the amino acid sequence of SEQ ID NO: 19, a CD8α hinge and CD8α transmembrane domain, a CD28 or 4-1BB co-stimulatory domain, and a CD3-ζ activation domain.

2. The CAR protein of claim 1, comprising an amino acid sequence at least 95% identical to SEQ ID NOS: 21-23, 31-33, or 40-41.

3. The CAR protein of claim 1, comprising an amino acid sequence identical to SEQ ID NOS: 21-23, 31-33, or 40-41.

4. An isolated polynucleotide molecule encoding a CAR protein according to claim 1.

5. The polynucleotide molecule of claim 4, further comprising a promoter active in eukaryotic cells.

6. The polynucleotide molecule of claim 4, further defined as an expression vector.

7. An isolated engineered cell comprising a polynucleotide molecule encoding a chimeric antigen receptor (CAR) that binds human leukocyte immunoglobulin like receptor 4 (LILRB4) and comprises an extracellular domain comprising a single chain variable fragment comprising (i) a VH comprising the amino acid sequence SEQ ID NO: 7 and a VL comprising the amino acid sequence of SEQ ID NO: 9, or (ii) a VH comprising the amino acid sequence of SEQ ID NO: 17 and a VL comprising the amino acid sequence of SEQ ID NO: 17, a CD8α hinge and CD8α transmembrane domain a CD28 or 4-1BB co-stimulatory domain, and a CD3-ζ activation domain.

8. The cell of claim 7, wherein the cell is a T cell.

9. The cell of claim 7, wherein the cell is an NK Cell.

10. The cell of claim 7, further comprising a transposase.

11. A method of inhibiting or reducing the severity of acute myeloid leukemia (AML) in a human subject in need thereof comprising administering to the subject an effective amount of a cell therapy comprising one or more cells in accordance with claim 7.

12. The method of claim 11, further comprising administering to said human subject a second cancer therapy.

13. The method of claim 12, wherein said second cancer therapy is chemotherapy, immunotherapy, radiotherapy, hormone therapy or surgery.

14. The method of claim 12, wherein said second cancer therapy is administered at the same time as the cell therapy.

15. The method of claim 12, wherein said second cancer therapy is administered before or after the cell therapy.

16. The method of claim 11, wherein said cell therapy is administered local to cancer site, region to a cancer site, or systemically.

* * * * *